(12) United States Patent
Saunders et al.

(10) Patent No.: US 8,523,930 B2
(45) Date of Patent: Sep. 3, 2013

(54) METHODS AND DEVICES FOR COOLING SPINAL TISSUE

(75) Inventors: Todd Sheppard Saunders, Boston, MA (US); Jared Samuel Fry, Boston, MA (US)

(73) Assignee: Neuraxis, LLC, Traverse City, MI (US)

( * ) Notice: Subject to any disclaimer, the term of this patent is extended or adjusted under 35 U.S.C. 154(b) by 370 days.

(21) Appl. No.: 13/107,210

(22) Filed: May 13, 2011

(65) Prior Publication Data

US 2011/0282418 A1    Nov. 17, 2011

Related U.S. Application Data

(60) Provisional application No. 61/395,585, filed on May 14, 2010, provisional application No. 61/456,794, filed on Nov. 12, 2010.

(51) Int. Cl.
*A61F 7/00* (2006.01)
*A61F 2/44* (2006.01)

(52) U.S. Cl.
USPC .................. 607/105; 607/113; 623/17.11

(58) Field of Classification Search
USPC ............. 607/96, 105, 113; 606/20–26; 623/16.11–23.63
See application file for complete search history.

(56) References Cited

U.S. PATENT DOCUMENTS

| 4,745,922 A | 5/1988 | Taylor |
| 4,784,126 A | 11/1988 | Hourahane |
| 5,108,390 A | 4/1992 | Potocky et al. |
| 5,196,015 A | 3/1993 | Neubardt |
| 5,433,739 A | 7/1995 | Sluijter et al. |
| 5,474,558 A | 12/1995 | Neubardt |
| 5,531,776 A | 7/1996 | Ward et al. |
| 5,571,147 A | 11/1996 | Sluijter et al. |
| 5,616,143 A | 4/1997 | Schlapfer et al. |
| 5,899,898 A | 5/1999 | Arless et al. |

(Continued)

FOREIGN PATENT DOCUMENTS

| SU | 1727802 | 4/1992 |
| WO | 2009103758 A2 | 8/2009 |

OTHER PUBLICATIONS

[No Author Listed] Thermally Conductive Polymers—CoolPoly Thermally Conductive Plastics. Cool Polymers. 2013. http://www.coolpolymers.com/. 1 page. Last Accessed Feb. 20, 2013.

(Continued)

*Primary Examiner* — Linda Dvorak
*Assistant Examiner* — Adam Avigan
(74) *Attorney, Agent, or Firm* — Nutter McClennen & Fish LLP

(57) ABSTRACT

Methods, systems, and devices are disclosed for cooling tissue, and in particular for applying therapeutic hypothermia to the spinal canal, tissue disposed within the spinal canal, and nerve roots extending from the spinal canal. Bone screws, intervertebral implants, stabilization rods, spinous process spacers, and other devices are described which define a chamber through which a chilled fluid, expandable gas, or other coolant means can be circulated, delivered, or activated to cool adjacent tissue. The degree of cooling can be regulated using a controller, which can be configured to increase or decrease the cooling effect based on any of a variety of measured or predicted physiological or thermodynamic properties. Methods are disclosed for implanting cooling instruments and for carrying out various treatment regimens that involve cooling tissue using such instruments.

41 Claims, 22 Drawing Sheets

(56) References Cited

U.S. PATENT DOCUMENTS

| | | | |
|---|---|---|---|
| 6,343,644 B1 | 2/2002 | Huang et al. | |
| 6,613,044 B2 | 9/2003 | Carl | |
| 6,629,975 B1 | 10/2003 | Kilpela et al. | |
| 6,749,605 B2 | 6/2004 | Ashley et al. | |
| 6,796,985 B2 | 9/2004 | Bolger et al. | |
| 7,044,946 B2 | 5/2006 | Nahon et al. | |
| 7,144,394 B2 | 12/2006 | Carl | |
| 7,220,951 B2 | 5/2007 | Truckai et al. | |
| 7,241,297 B2 | 7/2007 | Shaolian et al. | |
| 7,449,019 B2 | 11/2008 | Uchida et al. | |
| 7,645,282 B2 | 1/2010 | Huxel et al. | |
| 7,651,496 B2 | 1/2010 | Keegan et al. | |
| 7,722,620 B2 | 5/2010 | Truckai et al. | |
| 8,348,952 B2 | 1/2013 | Sanders et al. | |
| 2002/0095144 A1* | 7/2002 | Carl | 606/21 |
| 2003/0018331 A1 | 1/2003 | Dycus et al. | |
| 2003/0216721 A1 | 11/2003 | Diederich et al. | |
| 2005/0149007 A1 | 7/2005 | Carl | |
| 2006/0015160 A1 | 1/2006 | Larnard | |
| 2006/0241576 A1 | 10/2006 | Diederich et al. | |
| 2007/0050002 A1 | 3/2007 | Elefteriades | |
| 2007/0162007 A1 | 7/2007 | Shoham | |
| 2007/0191831 A1 | 8/2007 | Sanders et al. | |
| 2007/0225781 A1 | 9/2007 | Saadat et al. | |
| 2007/0233148 A1 | 10/2007 | Truckai et al. | |
| 2007/0233226 A1 | 10/2007 | Kochamba et al. | |
| 2007/0233249 A1 | 10/2007 | Shadduck | |
| 2007/0260232 A1 | 11/2007 | Carl | |
| 2007/0260250 A1 | 11/2007 | Wisnewski et al. | |
| 2008/0065062 A1 | 3/2008 | Leung et al. | |
| 2008/0065083 A1 | 3/2008 | Truckai et al. | |
| 2008/0154373 A1* | 6/2008 | Protopsaltis et al. | 623/17.12 |
| 2008/0249532 A1 | 10/2008 | Schoutens et al. | |
| 2008/0269761 A1 | 10/2008 | Truckai et al. | |
| 2008/0294222 A1 | 11/2008 | Schechter | |
| 2009/0036893 A1 | 2/2009 | Kartalian et al. | |
| 2011/0066216 A1 | 3/2011 | Ting et al. | |
| 2012/0221059 A1 | 8/2012 | Mollman et al. | |

OTHER PUBLICATIONS

[No Author Listed] Gap Pad Products—Thermal Materials, Thermal Solutions. The Bergquist Company. 2013. http://www.bergquistcompany.com/thermal_materials/gap-pad.htm. 2 pages. Last Accessed Feb. 20, 2013.

[No Author Listed] BioMedical. Tullurex. 2013. http://www.tellurex.com/markets/biomedical.php. 2 pages. Last Accessed Feb. 20, 2013.

International Search Report and Written Opinion, PCT/US2011/036436, dated Feb. 9, 2012 (11 Pages).

* cited by examiner

METHODS AND DEVICES FOR COOLING SPINAL TISSUE

CROSS-REFERENCE TO RELATED APPLICATIONS

This application claims the benefit of priority of U.S. Provisional Patent Application No. 61/395,585, filed on May 14, 2010, the entire contents of which are incorporated herein by reference. This application also claims the benefit of priority of U.S. Provisional Patent Application No. 61/456,794, filed on Nov. 12, 2010, the entire contents of which are incorporated herein by reference.

FIELD

The present invention relates to methods and devices for cooling tissue. More particularly, the present invention relates to methods and devices for cooling spinal tissue (e.g., spinal neuraxis tissue).

BACKGROUND

According to the National Spinal Cord Injury Statistical Center, there are more than 259,000 people living with a spinal cord injury in the United States. Traumatic spinal cord injury afflicts around 15,000 people in the United States each year. Approximately 12,000 survive the cord injury with a neurological deficit, which is commonly a severe, disabling physical impairment and mental burden. Long-term care for cord injuries costs an estimated $9.7 billion annually in the United States.

Application of certain degrees of hypothermia to a patient's spine and spinal cord after a spinal cord injury can lead to benefits, such as a reduction of the metabolic demand of spinal cord cells, reduction of edema, added tolerance to hypoxia/ischemia, and ultimately a reduction in spinal cord tissue damage or cell death. Realizing these benefits could mean the difference between quadriplegia and being able to use one's arms. The use of a cooling effect for these purposes can be referred to as therapeutic hypothermia.

Besides traumatic spinal cord injury, the spinal cord can be injured due to surgical procedures such as abdominal aneurysm repair, wherein blood flow to the spinal cord is reduced. This lack of blood flow, also known as ischemia, can cause cellular damage to the spinal cord. Local cooling of the spinal cord can decrease the incidence of spinal cord injury in abdominal aneurysm surgery. Nerve roots or any member of the central nervous system in the spine can also become damaged from trauma and/or surgical insult, and can cause neurologic deficits and/or significant patient pain. It will be appreciated that the spinal cord and nerves can become injured through any number of means.

Existing methods for cooling the spine involve systemic cooling of the entire body. Such treatments carry a number of disadvantages. For one thing, systemic cooling techniques lack the ability to specifically target the injured tissue and, as a result, other unrelated tissue can be damaged or destroyed by the cooling. Systemic cooling can also cause a wide variety of side effects. In addition, the degree to which the body can be cooled systemically is very limited, and it is difficult to precisely control the degree to which the body is cooled in systemic approaches. Body temperature changes using systemic techniques also tend to occur very slowly, which can undesirably delay administration of a cooling effect to the injured tissue. Accordingly, a need exists for improved methods, systems, and devices for cooling tissue.

SUMMARY

Methods, systems, and devices are disclosed herein that generally involve cooling tissue (e.g., localized cooling of tissue), and in particular for applying therapeutic hypothermia to the spinal canal, tissue disposed within the spinal canal, and nerve roots extending from the spinal canal. Bone screws, intervertebral implants, stabilization rods, spinous process spacers, and other devices are disclosed which define a chamber through which a chilled fluid, expandable gas, or other coolant means can be circulated, delivered, or activated to cool adjacent tissue. The degree of cooling can be regulated using a controller, which can be configured to increase or decrease the cooling effect based on any of a variety of measured or predicted physiological or thermodynamic properties. Methods are disclosed for implanting cooling instruments and for carrying out various treatment regimens that involve cooling tissue using such instruments.

In one aspect of the invention, a method for cooling tissue is provided that includes delivering an implant through a tissue opening and into a bony structure of a vertebra such that the implant is fixedly engaged with the vertebra, and applying a cooling effect to the bony structure from the implant to cool tissue in a spinal canal adjacent to the vertebra.

The implant can be configured to be used as a fixation device. In one embodiment, the implant is a bone screw and delivering the implant comprises implanting the bone screw into a pedicle of the vertebra. The method can also include coupling a spinal stabilization rod to the implant. Delivering the implant can include threading the implant into the bony structure of the vertebra. The bony structure can be a posterior arch of the vertebra, a lamina of the vertebra, and/or a pedicle of the vertebra.

The method can also include closing the tissue opening with the implant remaining in the bony structure of the vertebra. The implant can be positioned in proximity to a wall of the pedicle adjacent to a spinal canal such that applying the cooling effect cools the spinal canal. The method can also include delivering a second implant into a contralateral side of the vertebra.

Applying the cooling effect can include delivering a pressurized gas to a chamber formed within the implant and/or delivering a cooled liquid to a chamber formed within the implant. The method can also include withdrawing the cooled liquid from the chamber through an exhaust conduit and/or dynamically controlling the cooling effect to increase and decrease the cooling effect, for example by increasing or decreasing a rate of fluid flow through the implant based on one or more measured physiological characteristics and/or by increasing or decreasing a temperature of fluid supplied to the implant based on one or more measured physiological characteristics. The method can also include, prior to or during said controlling, measuring the one or more measured physiological characteristics using a sensor.

The implant can include an insert and a bone screw and delivering the implant can include inserting the bone screw into a bone hole and then delivering the insert into an opening in the bone screw. In one embodiment, applying the cooling effect reduces a temperature of a portion of a spinal cord adjacent to the vertebra by at least about 2 degrees Celsius. The method can also include separating the at least one conduit from the implant, for example by deflating a coupling balloon.

In another aspect of the invention, an apparatus for cooling a spinal canal is provided that includes a biocompatible bone screw having proximal and distal ends and a chamber therein. The bone screw can be configured for placement within a vertebra. A delivery conduit can be coupled to the bone screw and in fluid communication with the chamber such that the delivery conduit is configured to supply a cooling medium to the chamber. An exhaust conduit can also be coupled to the bone screw and in fluid communication with the chamber.

A cannulated tunnel can extend through an entire length of the bone screw such that the cannulated tunnel is in fluid isolation relative to the chamber. The bone screw can include a body portion, a neck portion proximal to the body portion, and a head portion proximal to the neck portion. The head portion can include a driving interface and the delivery conduit and exhaust conduit can be configured to be selectively coupled to the driving interface.

The bone screw can also include a rod receiving head and the apparatus can include a spinal rod configured to be selectively coupled to the rod receiving head. The spinal rod can include an aperture through which the delivery conduit and the exhaust conduit can be routed from the bone screw to a skin surface of a patient when the spinal rod and the bone screw are implanted in a spine of the patient. The delivery conduit and the exhaust conduit can be coupled to the neck portion of the bone screw, which can be curved or bent such that the head portion is offset from a longitudinal axis of the body portion.

An expansion nozzle can be disposed at a distal end of the delivery conduit, in a central portion of the bone screw, and/or in a portion of the bone screw configured to be positioned adjacent to a patient's spinal canal when the bone screw is implanted in a pedicle of the patient. The delivery conduit can terminate at a location adjacent to the distal end of the bone screw and the exhaust conduit can terminate at a location adjacent to the proximal end of the bone screw.

In one embodiment, the chamber can include a fluid lumen having a first end coupled to the delivery conduit and a second end coupled to the exhaust conduit. The fluid lumen can be coiled and/or snaked.

A Peltier device can be disposed within the chamber and a controller can be configured to adjust an amount of current supplied to the Peltier device. The delivery conduit can include an electrical lead for supplying current to the Peltier device and the exhaust conduit can be configured to remove heat generated by the Peltier device from the chamber.

The chamber can be formed in a removable insert such that the insert is selectively positionable within an interior of the bone screw. At least one sensor can be configured to generate an output indicative of at least one of a physiological condition and a temperature of the bone screw, and a controller can be configured to adjust at least one of a rate at which a cooling medium is provided to the delivery conduit and a temperature of the cooling medium based on the output of the sensor.

The apparatus can also include a coupling balloon having at least an inflated configuration in which the balloon forms an interference fit to couple the delivery conduit and the exhaust conduit to the bone screw and a deflated configuration in which the delivery conduit and the exhaust conduit are separable from the bone screw. Application of a cooling medium to the delivery conduit can be effective to maintain the balloon in the inflated configuration and evacuation of a cooling medium from the delivery conduit can be effective to transition the balloon from the inflated configuration to the deflated configuration.

In another aspect of the invention, a method for cooling tissue is provided that includes implanting a disc replacement member in a disc space between a first vertebra and a second vertebra such that the disc replacement member stabilizes the first and second vertebrae, and cooling the disc replacement member to cool tissue in a spinal canal adjacent to the disc space.

The disc replacement member can be effective to maintain a height of the disc space, and the method can include securing the disc replacement member to at least one of the first and second vertebrae so as to resist movement of the disc replacement member relative to the first and second vertebrae. Cooling the disc replacement member can include delivering a pressurized gas to a chamber formed within the disc replacement member and/or delivering a cooled fluid to a chamber formed within the disc replacement member. The method can also include withdrawing the cooled fluid from the chamber through an exhaust conduit and/or dynamically controlling the cooling of the disc replacement member such that a degree of cooling can be increased and decreased, for example by increasing or decreasing at least one of a rate of fluid flow through the disc replacement member and a temperature of fluid supplied to the disc replacement member based on one or more measured characteristics. The one or more measured characteristics can include at least one of a physiological characteristic and a temperature of the disc replacement member. The method can include, prior to or during said controlling, measuring the one or more measured characteristics using a temperature sensor.

In one embodiment, cooling the disc replacement member can reduce a temperature of the tissue by at least about 2 degrees Celsius. The method can also include closing a tissue opening through which the disc replacement member was implanted with the disc replacement member remaining in the disc space and/or separating the at least one conduit from the disc replacement member, for example by deflating a coupling balloon.

In another embodiment of the invention, an apparatus for cooling a spinal canal is provided that includes an implant having a posterior end and an anterior end and defining a chamber therein. The implant can be configured for placement within a disc space between adjacent vertebrae. A delivery conduit can be coupled to the implant and can be in fluid communication with the chamber, and the delivery conduit can be configured to supply a cooling medium to the chamber. An exhaust conduit can also be coupled to the implant and in fluid communication with the chamber.

The implant can include fenestrations packed with a bone growth promoting substance and/or can include surface features for fixedly engaging the adjacent vertebrae. An expansion nozzle can be disposed at a distal end of the delivery conduit. The delivery conduit can terminate at a location adjacent to the posterior end of the implant and the exhaust conduit can terminate at a location adjacent to the anterior end of the implant.

The chamber can include a fluid lumen having a first end coupled to the delivery conduit and a second end coupled to the exhaust conduit. The fluid lumen can be coiled and/or snaked. A Peltier device can be disposed within the chamber and a controller can be configured to adjust an amount of current supplied to the Peltier device. The delivery conduit can include an electrical lead for supplying current to the Peltier device and the exhaust conduit can be configured to remove heat generated by the Peltier device from the chamber.

A coolant source can be configured to provide the cooling medium to the delivery conduit. The apparatus can also include a controller configured to adjust at least one of a rate at which the cooling medium is provided to the delivery conduit and a temperature of the cooling medium. At least one sensor can be configured to generate an output indicative of at least one of a physiological condition and a temperature of the implant, and the controller can be configured to adjust the rate at which the cooling medium is provided to the delivery conduit based on the output of the sensor.

The apparatus can also include a coupling balloon having at least an inflated configuration in which the balloon forms an interference fit to couple the delivery conduit and the exhaust conduit to the implant and a deflated configuration in which the delivery conduit and the exhaust conduit are separable from the implant. Application of the cooling medium to the delivery conduit can be effective to maintain the balloon in the inflated configuration and evacuation of the cooling medium from the delivery conduit can be effective to transition the balloon from the inflated configuration to the deflated configuration. The implant can have a cross section that is at least one of elliptical, toroidal, T-shaped, and rectangular.

At least one dividing wall can extend into the chamber and can be configured to direct the cooling medium through the chamber. The delivery conduit can be coupled to the chamber on a first side of the dividing wall and the exhaust conduit can be coupled to the chamber on a second side of the dividing wall. At least a portion of a posterior surface of the implant can have an increased thermal conductivity relative to the remainder of the implant.

In another aspect of the invention, a spinal fixation apparatus is provided that includes a biocompatible spinal fixation rod having a proximal end and a distal end and defining a chamber therein, the rod being configured for securement to a patient's spine by at least one bone anchor. A delivery conduit can be coupled to the rod and in fluid communication with the chamber such that the delivery conduit is configured to supply a cooling medium to the chamber. An exhaust conduit can also be coupled to the rod and in fluid communication with the chamber.

In another aspect of the invention, a spinous process spacer is provided that includes an implant sized and configured for placement between a first spinous process of a first vertebra and a second spinous process of a second vertebra adjacent to the first vertebra such that the implant stabilizes the first and second vertebrae. The implant can have a chamber defined therein. A delivery conduit can be coupled to the implant and in fluid communication with the chamber. The delivery conduit can be configured to supply a cooling medium to the chamber. An exhaust conduit can also be coupled to the implant and in fluid communication with the chamber.

In another aspect of the invention, a method for cooling tissue is provided that includes inserting a cooling instrument into a cannulation of a bone screw implanted in a pedicle of a vertebra and applying a cooling effect to the vertebra from the cooling instrument to cool tissue in a spinal canal adjacent to the vertebra.

In one embodiment, a method for cooling tissue includes creating a hole in a pedicle of a vertebra and inserting an instrument into the pedicle. A cooling effect can be applied from the cooling instrument such that the cooling effect is applied to at least the wall of the pedicle adjacent to the spinal canal.

In another embodiment, an apparatus for cooling tissue is provided that includes an elongated member for being implanted into a bony structure of a vertebra. A cooling instrument can be insertable into the elongated member such that the cooling instrument is removable. The elongated member can be a load bearing anchor for surgical stabilization of the spine.

In another embodiment, a method for cooling tissue includes placing a cooling instrument in the intervertebral space and applying a cooling effect from the cooling instrument. At least a portion of the cooling instrument can remain in the intervertebral space after cooling has ceased and can be secured against a vertebral body.

In another embodiment, a method for cooling tissue includes placing a cooling instrument in the intervertebral space, bearing and/or applying a load from the vertebral bodies upon at least a portion of the cooling instrument, and applying a cooling effect from the cooling instrument.

In another embodiment, a method for cooling tissue includes placing an intervertebral spacer in the intervertebral space and applying a cooling effect from the spacer. Applying the cooling effect can include introducing a cooling fluid into at least a portion of the intervertebral spacer. A load can be applied to the intervertebral spacer and the spacer can be allowed to fuse into its surrounding bone.

In another embodiment, an apparatus for cooling tissue is provided that includes an intervertebral spacer adapted to maintain a height between adjacent vertebral bodies, a coolant source, a control unit, and a conduit that interfaces the coolant source with the intervertebral spacer and is able to deliver coolant from the coolant source to the intervertebral spacer. The control unit can be adapted to control the amount of coolant delivered.

The present invention further provides methods, systems, and devices as claimed.

BRIEF DESCRIPTION OF THE DRAWINGS

The invention will be more fully understood from the following detailed description taken in conjunction with the accompanying drawings, in which.

DETAILED DESCRIPTION

Figure 1A:
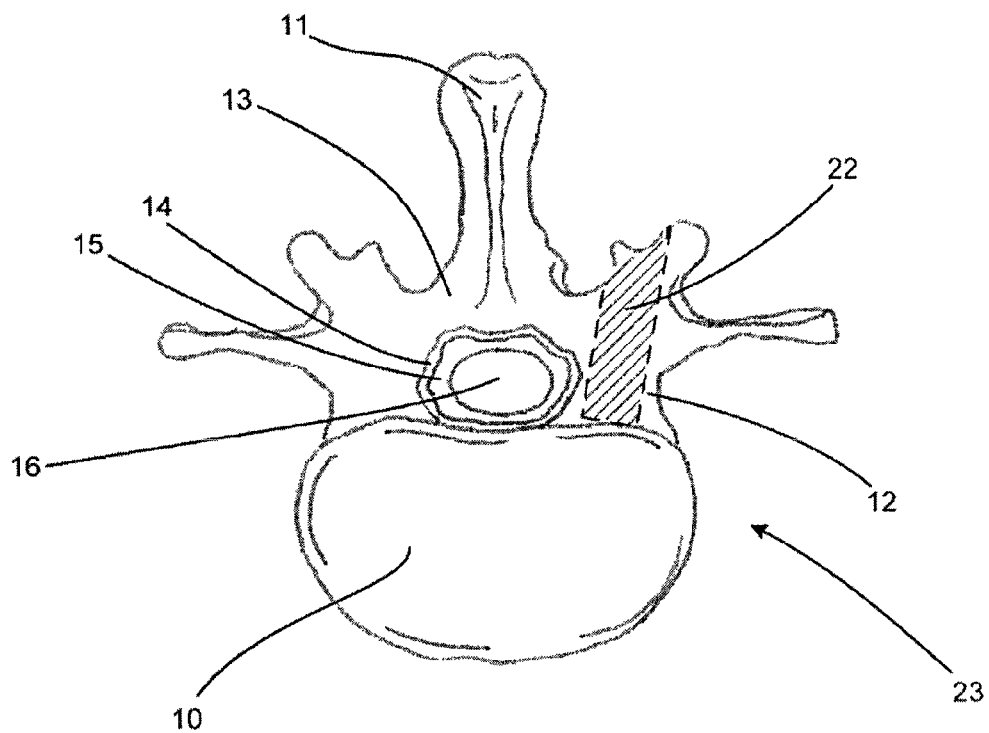
FIG. 1A is a transverse sectional view of a vertebra, the vertebra including a trans-pedicular hole for receiving a cooling instrument.

Certain exemplary embodiments will now be described to provide an overall understanding of the principles of the structure, function, manufacture, and use of the methods, systems, and devices disclosed herein. One or more examples of these embodiments are illustrated in the accompanying drawings. Those skilled in the art will understand that the methods, systems, and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In the description that follows, reference is made primarily to cooling tissue in and around the spinal canal, including the spinal cord, but it will be appreciated that the methods, systems, and devices disclosed herein can also be used to cool tissue in virtually any part of a human or animal body, including organs, joints (e.g., hips, knees, elbows, shoulders), the brain, the heart, etc. It will also be appreciated that the term "spinal tissue" as used herein can include the spinal cord itself, as well as nerves and nerve roots extending therefrom through spaces in the spinal column, together the "spinal neuraxis," as well as other portions of the central nervous system.

Hypothermia Delivery—Temperature & Time

The methods, systems, and devices described herein generally involve applying localized therapeutic hypothermia and, in some cases, cooling the tissue in and around the spinal cord. Various hypothermic instrumentations are described to deliver a cooling effect to the spinal canal, and to the spinal cord itself. "Therapeutic hypothermia" as used herein refers to the reduction of tissue temperature below a patient's normal body temperature, typically about 37 degrees C. Therapeutic hypothermia can also include reduction of tissue temperature below a patient's body temperature when treatment is initiated, which may not be the patient's normal body temperature (e.g., when the patient presents with a fever or in an already-hypothermic state, for example due to previous or ongoing systemic hypothermia treatment).

The degree of hypothermia applied can vary upon a number of factors. Target therapeutic temperatures can range from just below 0 degrees C. to just below normothermia. Tissue exposure to temperatures below 0 degrees C. can lead to cellular damage, however the bones of the spinal column are relatively resilient to such low temperatures and therefore target therapeutic temperatures can be below 0 degrees C. in some embodiments.

In an exemplary embodiment, the target tissue is cooled to within a range of about 0 degrees C. to about 37 degrees C. The target tissue can also be cooled to within a range of about 5 degrees C. to about 36 degrees C., more preferably about 15 degrees C. to about 36 degrees C., more preferably about 25 degrees C. to about 36 degrees C., more preferably about 25 degrees C. to about 35 degrees C., and more preferably about 30 degrees C. to about 34 degrees C. In certain embodiments, the target tissue can be cooled to about 36 degrees C., about 35 degrees C., about 34 degrees C., about 33 degrees C., about 32 degrees C., about 31 degrees C., or about 30 degrees C. In other aspects, the target tissue can be cooled to about 1 degree C. below normothermia, about 2 degrees C. below normothermia, about 5 degrees C. below normothermia, about 10 degrees C. below normothermia, or about 20 degrees C. below normothermia.

Degrees of hypothermia are sometimes described in terms of "mild" hypothermia (e.g., 0-5 degrees C. below normothermia), "moderate" hypothermia (e.g., 5-9 degrees C. below normothermia), "severe" hypothermia (e.g., 9-17 degrees C. below normothermia), and "profound" hypothermia (e.g., more than 17 degrees C. below normothermia). The methods disclosed herein can include cooling of tissue to within any of these ranges, and the systems and devices disclosed herein can be configured to achieve such cooling. Various treatment protocols can also be used in which the tissue temperature is cycled, pulsed, swept, ramped, and/or stepped through these or other ranges. For example, in one treatment method, the tissue temperature can be quickly lowered to a target temperature and then slowly ramped back up to normothermia when it is desired to cease treatment. By way of further example, the tissue temperature can be slowly stepped down to a first target temperature, oscillated between the first target temperature and a second target temperature, and then eventually stepped back up to normothermia.

The duration of exposure of the target tissue to the cooling effect can range from minutes to days depending on a variety of factors, including the patient's condition, the treatment of the patient's other injuries, the prospective treatment protocol for the patient, and monitored or detectable physiological responses, or lack thereof, to the cooling. Therapeutic hypothermia can be applied in a single procedure or multiple times. In either case, a multiplicity of different temperatures can be applied. Preferably, when discussing target temperatures, it is intended to mean the desired therapeutic temperature of the targeted tissue. Alternatively, target temperature at times can also refer to the temperature of the cooling instrument or the cooling chamber or element of the cooling instrument. It will be appreciated that it can be necessary in some instances to cool the cooling instrument to below the target tissue temperature in order for the target tissue to reach the target tissue temperature.

The methods described herein can include cooling the spinal canal tissue and the spinal cord for variable lengths of time and/or at different temperatures. In addition, cooling can occur in multiple doses, where each dose can differ from the others in exposure time and/or temperature. The determination of the exposure time(s) and temperature(s) can be predetermined based on known effective times and temperatures or can be determined based on the condition of the patient and/or when the treatment is applied relative to when the injury occurred. A wide variety of physiological effects, both local and systemic, can arise from the cooling of the target tissue (e.g., spinal canal tissue and the spinal cord) below normal body temperature. Exposure time, doses, and target temperature can be varied during the procedure based on monitored physiological parameters or characteristics as well as parameters of the cooling devices or systems.

These parameters include, but are not limited to, neurological findings, blood pressure, target-tissue temperature, specific tissue temperature (proximate to target tissue), core (rectal) body temperature, venous blood temperature near or exiting target tissue, pulmonary conditions, cardiac conditions, sensory evoked potentials (SEPs, including somatosensory evoked potentials), motor-evoked potentials (MEPs), intrathecal pressure, perfusion pressure, levels of blood oxygen & glucose, ATP concentrations, markers of excitotoxicity, vasogenic edema, apoptosis, inflammation, and enzymatic responses. The target temperature, doses, and exposure time can be selected by initial measurements of these physiological parameters and then modified based upon real-time measurement of these parameters. Effectively, the cooling regimen, in terms of temperatures, exposure times, and doses, can be controlled by measured physiological characteristics of the patient and the cooling devices and systems.

For example, a cooling effect can be applied initially at a predetermined target temperature based on the type and severity of injury incurred, including for example the vertebral level of injury. The cooling effect can be increased, and as such, the target temperature can be reduced, if after a predetermined period of time, the motor-evoked potential responses of the patient appear unremarkable. In one embodiment, if the difference between the arterial blood pressure and the cerebral spinal fluid pressure reduces below a predetermined threshold, the application of the therapeutic hypothermia can be stopped. It should be understood that there are any number of protocols that can be followed in the application of therapeutic hypothermia based on clinical, laboratory, and monitoring markers.

In one embodiment, therapeutic hypothermia is initiated as soon as possible following a spinal injury, e.g., less than 8 hours after the injury. Therapeutic hypothermia can be maintained up to 72 hours, up to 120 hours, or more. It can be desirable to deliver therapeutic hypothermia for a much shorter duration as well, including as little as a fraction of an hour (e.g., 5 minutes, 15 minutes, 30 minutes, or 45 minutes).

The use of therapeutic hypothermia on the spinal cord and the spinal canal can yield a variety of beneficial effects. Such effects can include the reduction of nervous tissue metabolic demand, excitotoxic markers, apoptosis, free-radicals, and inflammation. It should be noted that some of the mechanisms of action associated with therapeutic hypothermia are not fully understood, but experience with its application in a variety of clinical situations suggests a mitigating effect in spinal cord damage from trauma, vascular insult, or surgical insult.

Transosseous Cooling

In some of the methods and devices described herein, a cooling effect is applied transosseously, or literally through bone. In particular, tissue can be cooled by implanting a cooling instrument into adjacent or nearby bone. Bone has properties that make it an advantageous cooling platform. Boney structures are readily locatable due to their greater density and rigidity than so-called soft tissues. Furthermore, their geometries are readily mapped radiographically, are relatively consistent between patients, and have easily locatable features or landmarks. Accordingly, particular surrounding or soft tissues are relatively consistently located in a known proximity to these bone structures and landmarks. In particular, vertebral pedicles and lamina lie in close proximity to the contents of the spinal canal, including the spinal cord and nerve roots.

These attributes allow specific surrounding soft tissue to be reliably targeted by using adjacently located bone structures and landmarks of the bone structures as a platform and avenue to put instruments near the specific soft tissue. Using bony structures and their landmarks as a means for targeting nearby or adjacent tissues helps avoid a need to directly target the tissue wishing to be treated, leaving the tissue undisturbed.

An advantageous aspect of a transosseous approach for providing a cooling effect to nearby soft tissue is the fact that bone is rigid, allowing for an instrument to be securely anchored into the bone, where the bone is not subject to deformation because of bodily movement or because of the instrument's presence. The rigid nature of the bone also allows instrument placement within boney margins, thus preventing the implanted instrument itself from disturbing the tissues outside of the bone. In practice, the wall of the bone may be slightly breached as a result of an effort to engage the instrument with the cortical bone, which has better structural properties.

A transosseous approach for providing a cooling effect to nearby soft tissue allows for the implantation of cooling instrumentation without disturbing the soft tissue itself. That is, by using a bone approach and cooling across the bone wall to the nearby tissue, the targeted nearby tissue isn't physically touched, displaced, or incised by the cooling instrument itself or by the surgical steps needed to implant the cooling instrument. Certain tissues, such as spinal cord tissue, are delicate and sensitive to disturbances, and such disturbances could cause permanent injury to the tissues. As such, it can be undesirable to implant cooling instruments in these tissues or in nearby soft tissues due to risks of causing injury to the tissues. Bone is very resilient to such disturbances, and typically does not realize a great loss in function or strength and is typically not susceptible to long term injury from such disturbances. It is therefore desirable to insert or implant a cooling instrument into a bony structure and cool nearby soft tissue transosseously, or across the bone wall, thus allowing for reliable cooling access to soft tissue without physically disturbing the soft tissue itself.

In an exemplary embodiment, the soft tissue that is targeted to be cooled is the spinal cord, other spinal canal tissue, and/or nerve root tissue, and the bony structures which act as the cooling platform are parts of a vertebra, including the elements of the posterior arch such as the pedicles, the lamina, and the spinous process. A transosseous approach for providing cooling across pedicle and/or lamina bone to the adjacent spinal canal contents targets the spinal cord without its actual contact, displacement, or penetration. This can be a critical consideration since the spinal cord's tolerance for such intrusions is likely minimal.

Transosseous Approach

In one embodiment, a posterior percutaneous approach is used in which a tissue opening is formed to access the vertebral elements of a patient. It will be appreciated that the tissue opening can also be formed in connection with an open surgical approach. Through the tissue opening, a hole is created in a bony structure of a vertebra (e.g., at least one pedicle of the vertebra). In many cases, this hole is generated using a drill. In other cases, the hole is generated using a self-drilling screw. Still in other cases, the hole is generated using an awl or a pedicle probe. It will be appreciated that any method for creating a hole is possible. A cooling instrument can be passed through the tissue opening and inserted into the hole such that the cooling instrument is positioned where it is able to cool the walls of the pedicle, and as such cool the tissue on the other side of the walls of the pedicle. The hole created in the pedicle can be created specifically for this procedure, or as part of a separate procedure, such as spinal stabilization. Furthermore, the hole created in the pedicle can be created immediately prior to inserting the cooling instrument, as part of the insertion of the cooling instrument, or can be created far in advance to inserting the cooling instrument. The hole can also be formed by the cooling instrument itself. In other embodiments, the hole can be created in other parts of the vertebra, for example in a more lateral portion (as in the case of the use of a lateral mass screw), or in other parts of the posterior arch of the vertebra, such as the lamina or the spinous process.

In one embodiment, the cooling instrument can be a biocompatible bone screw or can have features similar thereto, such as a threaded exterior surface. Such a surface allows the screw to be inserted into the bone to resist pull-out. A threaded configuration of the cooling instrument can also allow the cooling instrument to be load bearing, and as such, an acceptable component of any subsequent spinal stabilization structure, including those using pedicle screws. A stabilization structure or procedure can include, but is not limited to, a motion-limiting, a motion-preserving, and/or a fixation structure or procedure.

Figure 1B:
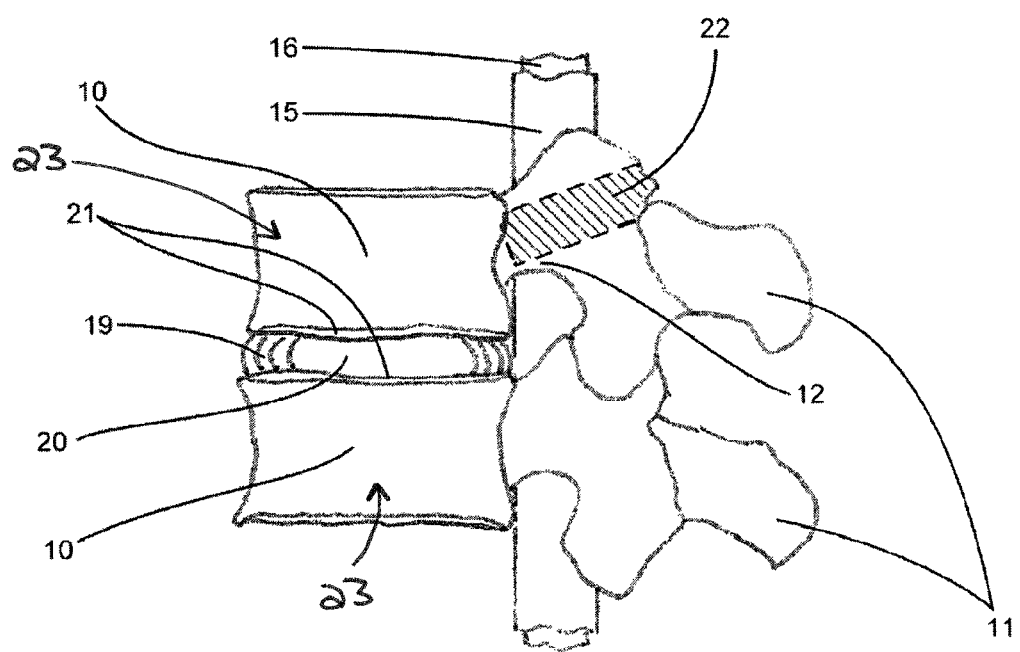
FIG. 1B is a lateral view of two vertebrae, one of which includes a hole for receiving a cooling instrument.

FIGS. 1A and 1B depict a hole 22 into which a cooling instrument can be implanted. In FIG. 1A, a transverse section of an exemplary vertebra 23 is shown, including the vertebral body 10, the pedicles 12, the laminae 13, the spinous process 11, the spinal canal 14, and the spinal canal contents 15, including the spinal cord 16. The spinal canal contents 15 include, for example, epidural space, dura mater, subdural space, arachnoid space, subarachnoid space, intrathecal space, cerebral spinal fluid, pia mater, spinal arteries and veins, vasocorona, vertebral venous plexus, nerve roots, ligaments, and fatty tissue. The tissues surrounding the vertebra, including ligaments, fat, organs, and muscle, are not shown in FIGS. 1A and 1B. It will be appreciated that there is symmetry as well as repetitive elements to a vertebra and referral to an element of the vertebra can be taken to mean any one of symmetric or multiple elements. For example, when referring to a pedicle, it can be intended to mean any one of the two, or both, pedicles of the vertebra.

The hole 22 can be created in a pedicle 12 of the vertebra, and it can extend in various orientations, such as axially into the pedicle 12 (e.g., along a longitudinal axis of the pedicle extending substantially in a posterior-anterior direction). It will be appreciated that the hole 22 can be created off-axis of the pedicle 12, in a trajectory of an alternative angle to the axis, offset from the axis, or on an alternative axis of the pedicle 12. It will also be appreciated that the depth of the hole 22 can extend through the entire length of the pedicle 12, a portion of the length, or extend beyond the length of the pedicle 12 into the vertebral body 10. In one aspect, the hole 22 is created such that a thin wall of pedicle bone is left remaining between the outer wall of the pedicle 12 adjacent to the spinal canal 14 and the inner wall of the hole 22. Having a thin wall of bone here can increase the efficiency in conducting heat away from the spinal canal contents 15 and the spinal cord 16 and providing a cooling effect to the spinal canal contents 15 and the spinal cord 16.

FIG. 1B shows a lateral view of the vertebra of FIG. 1A and an adjacent, inferior vertebra, positioned as they would be in a human patient. Also shown is the intervertebral disc, which generally includes an annulus fibrosis 19 and a nucleus pulposis 20, as well as the vertebral end-plates 21 which cap the superior and inferior sides of the disc. FIG. 1B also provides a lateral perspective on the trajectory of the hole 22. In the illustrated embodiment, the hole 22 is angled slightly in an inferior direction as it extends anteriorly from a posterior surface of the pedicle.

Figure 2:
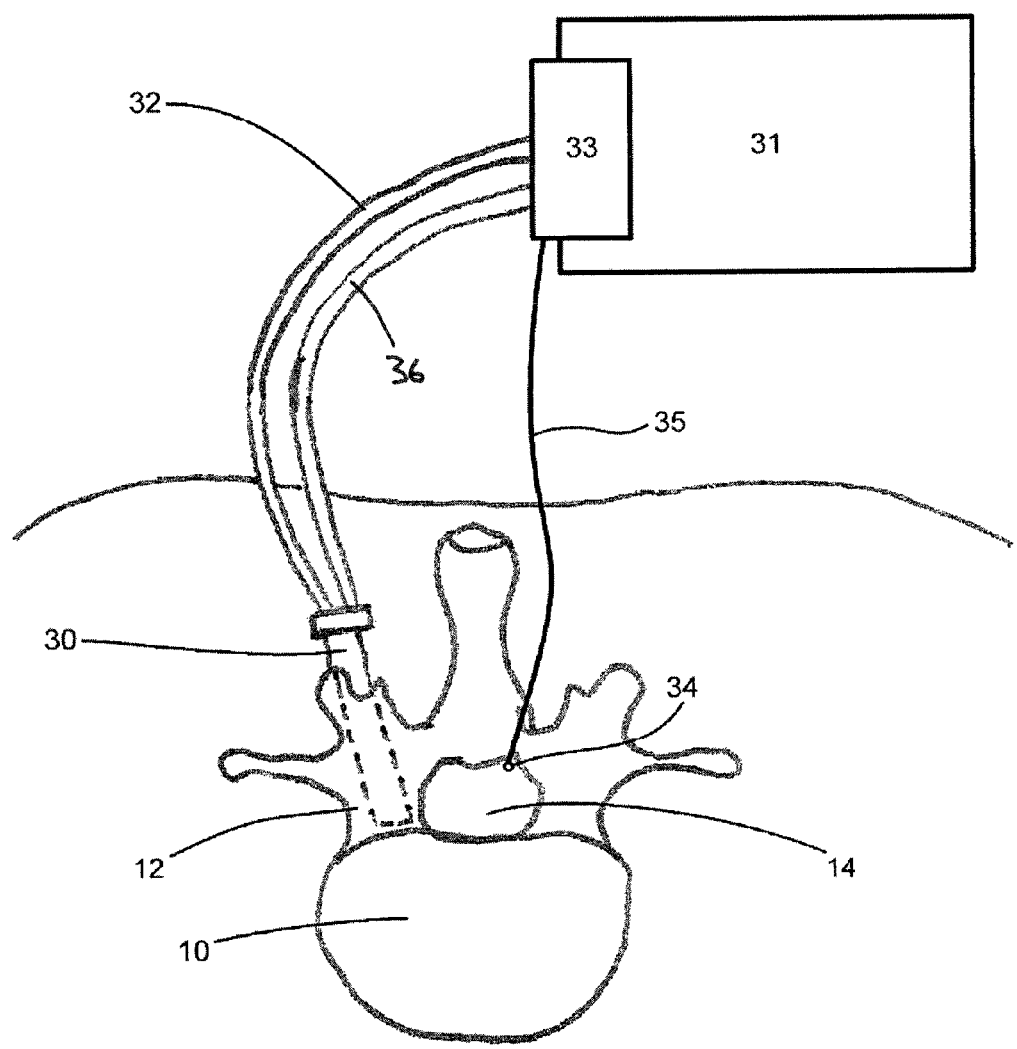
FIG. 2 is a schematic diagram of a cooling instrument disposed in the vertebra of FIG. 1 and coupled to a coolant source and a controller.

In FIG. 2, a cooling instrument 30 (which is also referred to herein as an "implant") is shown inserted into the hole in the pedicle 12. The cooling instrument 30 can be passed through the aforementioned tissue opening and placed within the hole 22 or it can be used to form the hole 22. For example, the hole 22 can be created by the insertion of the cooling instrument 30, such as in the case where the cooling instrument 30 is in the form of a self-drilling bone screw. The cooling instrument 30 can share the same outer diameter as the inner diameter of the hole 22, or the hole 22 can be slightly smaller than the diameter of the cooling instrument 30 to ensure a tight fit. The hole 22 can also have a larger diameter than the cooling instrument 30, in which case the gap between the hole 22 and the cooling instrument 30 can be filled with a thermally conductive substance or other material. In other implementations, a cannulated screw can be inserted into the hole 22 and the cooling instrument 30 can be inserted into the cannulation of the screw, whereby the cannulated screw acts to fill the gap.

Placing the cooling instrument 30 in the hole 22 is effective to position the cooling instrument 30 in close proximity to the spinal canal 14 and the contents 15 thereof, including the spinal cord 16. Furthermore, such an approach prevents the cooling instrument 30 from disturbing the spinal canal contents 15 due to the fact that the cooling instrument 30 is held by the rigid bounds of bone, close but not in contact with the canal contents 15.

Coolant Means and Source

The cooling instrument 30 can provide a cooling effect using any of a number of different coolant means or combinations thereof. For example, the coolant means can include the expansion of gas within the cooling instrument 30 or the circulating of a chilled fluid through the cooling instrument 30. The term "fluid," as used herein, refers to any flowable material or collection of materials, including liquids, gasses, and combinations thereof. In one embodiment, the cooling instrument 30 receives a compressed gas which by expansion acts as a coolant in the cooling instrument 30. The expansion of the gas causes the gas and the cooling instrument 30 around it to experience a rapid decrease in temperature. Typical gases for such an application include Nitrous Oxide and Carbon Dioxide, but it will be appreciated that there are a wide variety of gases that can be used, including gasses which, in compressed form, will be liquid. In other embodiments, the cooling instrument 30 receives a chilled liquid as the coolant means which flows through cavities or channels of the cooling instrument, effectively decreasing the temperature of the cooling instrument. Typical chilled liquids include saline solutions, water, liquid nitrogen, and ethyl alcohol. It will be appreciated that any number of fluids can be used as the coolant means, and that there are advantages to using biologically safe fluids. In still other embodiments, the cooling instrument 30 can contain a thermoelectric device, such as a Peltier device, which when a voltage or current is applied, at least a portion of the device experiences a reduction in temperature. The cooling instrument 30 can also house an endothermic chemical reaction which results in the reduction of temperature of the contents of the cooling instrument 30 and of the cooling instrument 30 itself. In other embodiments, the cooling instrument 30 is pre-chilled prior to insertion into the hole 22. It will be appreciated by those skilled in the art that there are a variety of means by which the cooling instrument 30 can be cooled.

The coolant means can be provided from an external (e.g., extracorporeal) coolant source 31. In implementations in which the coolant means is an expanding gas, the coolant source 31 can be a tank of compressed gas which is released into the cooling instrument 30 through a coolant delivery conduit 32. Once the compressed gas is in the cooling instrument 30, it can be expanded through an expansion nozzle 41 into an expansion chamber 42 in the cooling instrument 30, causing a rapid decrease in temperature. Alternatively, or in addition, the coolant source 31 can include a compressor that compresses the gas. In some implementations, the delivery of the coolant means from the tank of compressed gas is regulated with a control unit 33 to limit the amount of gas and the pressure at which it enters the cooling instrument 30 via the coolant delivery conduit 32. The control unit 33 can be an adjustable valve on the tank, which can be manually controlled, mechanically controlled, or automatically controlled by a computing device. In implementations in which the coolant source 31 includes a compressor, the control unit 33 can control the degree to which the compressor compresses the gas, or the pressure of the gas presented down the conduit 32. The regulation of the release of the gas can be managed manually or automatically, in either case, based on established protocols, conditions of the patient, and/or detectable physiological characteristics of the patient or characteristics of the cooling instrument. An additional conduit 36 can also be provided to exhaust expanded gas from the expansion chamber 42 of the cooling instrument 30. The exhaust conduit 36 can exhaust the gas into the atmosphere, to a collection tank, or to a compressor which in turn re-compresses the gas for reuse. The delivery conduit 32 and the exhaust conduit 36 are generally circular in cross-section, and can be formed from any of a variety of medical-grade, implantable, tubing materials known in the art. The conduits 32, 36 can be flexible or rigid, or can include rigid portions and flexible portions.

In implementations in which the coolant means is a chilled fluid, the coolant source 31 can be or can include a chiller or other apparatus for cooling and pumping fluid, and the coolant delivery conduit 32 can be a tube for delivering the chilled fluid to the cooling instrument 30. In this case, the exhaust conduit can be used to return or exhaust the chilled fluid from the cooling instrument 30 back to the coolant source 31, to a collection tank, or to a drain. In such an implementation, the control unit 33 can control the volume rate of chilled fluid flow, the pressure of the chilled fluid delivery lines, and/or the temperature of the chilled fluid. It will be appreciated that components of the fluid delivery and circulation system can be positioned on the exhaust side of the system rather than the source side (e.g. a pumping mechanism that pulls the chilled fluid through the instrument 30, the delivery conduit 32, and the exhaust conduit 36 rather than pushing it through).

In implementations in which the coolant means is a Peltier device embedded in the cooling instrument 30, the coolant source 31 can include a power supply that powers the Peltier device, and the coolant delivery conduit 32 can include electrical lines that supply electrical current from the power supply to the Peltier device. The delivery and exhaust conduits 32, 36 can also be used to remove heat generated by the Peltier device from the cooling instrument 30.

Delivery of the coolant means can be regulated to achieve a predetermined cooling effect, such as a specific temperature at a specific location. Delivery of the coolant means can also be regulated such that a specific volume of coolant of the coolant means is delivered, for example in the cases where the coolant means includes a chilled liquid or expandable gas. Delivery of the coolant means can also be regulated based on changes or lack of changes in physiological characteristics. For example, the regulation of the coolant means, and thus the intensity of cooling, can be determined by quantitative and qualitative sensory or motor-evoked potential (SEP, MEP) observations. In this example, the coolant means is provided at a certain level until the patient's SEP/MEP results begin to degrade, improve, or otherwise change, at which point the regulation of the coolant means can begin to reduce or increase the delivery of the coolant means. It will be appreciated that any number of physiological characteristics can be used to regulate the intensity of the coolant means, including but not limited to: blood pressure, target-tissue temperature, specific tissue temperature (proximate to target tissue), rectal body temperature, venous blood temperature near or exiting target tissue, pulmonary conditions, cardiac conditions, sensory evoked potentials (SEPs, including somatosensory evoked potentials), motor-evoked potentials (MEPs), intrathecal pressure, perfusion pressure, levels of blood oxygen & glucose, ATP concentrations, and effectors of excitotoxicity, vasogenic edema, apoptosis, inflammation, and enzymatic responses. A real-time qualitative or quantitative determination can be made based on any of the listed physiological characteristics as to how the coolant means should be regulated.

A sensor 34 can also be implanted in the cooling instrument 30 or in or around the patient. The sensor 34 can be a temperature sensor embedded in or on the cooling instrument 30 to sense the temperature the instrument exhibits, where this sensed temperature can then be used to control the delivery of the coolant means to the cooling instrument 30. The sensor 34 can be connected to the control unit 33 via one or more sensor wires 35 to provide a feedback loop of information to help determine how much coolant means and/or what temperature coolant means to deliver to the cooling instrument 30. Alternatively, or in addition, the sensor 34 can be connected via sensor wires 35 to a display, meter, dial, or other indicator providing some form of output data from the sensor 34 that can allow one to manually regulate the delivery of the coolant means. The sensor 34 can also be connectable wirelessly and a wireless link can be used instead of the sensor wires 35. In one implementation, the sensor 34 is a temperature measuring sensor, such as a thermistor or thermocouple, embedded into the cooling instrument 30 and providing temperature data of the cooling instrument 30, which is used to either manually or automatically regulate the delivery of the coolant means. Alternatively, the sensor 34 can be a temperature sensor embedded in the intrathecal space of the spinal canal contents 15 to measure temperature of cerebral spinal fluid.

It will be appreciated that more than one sensor 34, more than one sensor type, and more than one sensor placement location can be used simultaneously and that the data gathered from the multiple sensors 34 can be used independently or in combination to determine how the delivery of the coolant means is regulated. Other types of relevant sensors that can be used include pressure sensors, chemical sensors, electrical sensors, magnetic sensors, and optical sensors. Other types of sensing, such as remote sensing, can be used that do not require the sensor itself to be placed within the patient—ultrasound, including Doppler measurements, and functional MRI, all can be used to sense physiological characteristics that can be used to control or regulate the delivery of the coolant means. In one aspect, the information measured by a sensor or sensors can be used to continually adjust the regulation of the delivery of the coolant means in real time or almost real time. Alternatively, or in addition, the sensed information can be used for safety monitoring. The advantages of using a sensor or sensors, along with sensor wires or other communication means, will be appreciated though their use may not be necessary.

Cooling Instruments

Figure 3A:
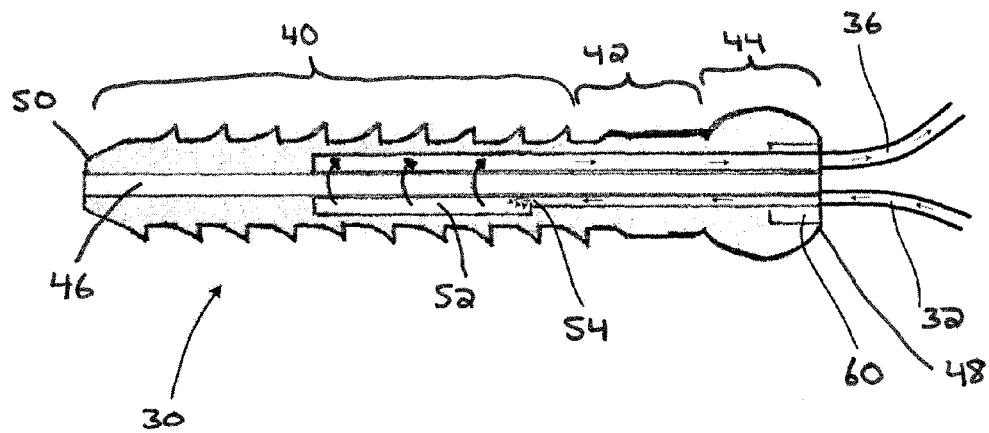
FIG. 3A is a longitudinal cross-sectional view of one embodiment of a spinal screw cooling instrument.

FIG. 3A depicts a cross-section of one implementation of a cooling instrument 30. In FIG. 3A, the cooling instrument 30 is an elongate member, such as a cylindrical rod or bone screw, having a body portion 40, a neck portion 42, and a head portion 44. The body portion 40, and optionally the neck portion 42, can have a threaded exterior surface. The cooling instrument 30 can thus be screwed or threaded into the hole 22, and as such, be securely anchored into hole 22 and to the vertebra 23. Such anchoring prevents the cooling instrument 30 from shifting or moving in or from the hole 22 prior, during, or after any cooling or other procedure unless specifically intended by the surgical staff. On its exterior, the cooling instrument 30 can resemble any of a variety typical surgical screws common in the marketplace. The cooling instrument 30 can have a conical or tapered distal tip to allow for easier alignment and insertion of the cooling instrument 30 into the hole 22. The cooling instrument 30 can also be self-tapping or self-drilling. In the case where the cooling instrument 30 is self-drilling, it can be used to create the hole 22 in the bone. Alternatively, the cooling instrument 30 can be a smooth elongated member or rod without threads, or can be ribbed. The cooling instrument 30 can utilize other means to anchor itself in the hole 22 once inserted, such as threads, ribs, retractable elements, barbs, etc. Though it is advantageous for the cooling instrument 30 to be anchored into the hole 22, it is not necessary.

In the illustrated embodiment, the cooling instrument 30 includes a proximal end 48 and a distal end 50 and can define a chamber 52 therein. The chamber 52 can house at least a portion of the elements, volumes, nozzles, and fluid lumens, channels, or paths, etc. needed to support the coolant means. In implementations in which the coolant means includes expanding gas, the cooling instrument 30 can include an expansion nozzle 54 through which gas that has entered the cooling instrument 30 via the coolant delivery conduit 32 expands. The gas is expanded into the chamber 52, from which it can be exhausted from the cooling instrument 30 via the exhaust conduit 36. The expanded gas can be exhausted into the environment, into a chamber or tank, or into a compressor which re-compresses it. The flow of the gas is depicted in FIG. 3A by means of the arrows contained within the elements of the figure. In particular, the arrows show that the gas expands around expansion chamber 52, which in this implementation, surrounds the cannulation channel 46 concentrically. Although it may appear that the expansion chamber 52 is separated by the cannulation channel 46, it should be understood that the two depicted sides of the expansion chamber 52 are connected as a single expansion chamber 52 that surrounds the cannulation channel 46. It should also be appreciated that the illustrated cannulation channel 46 is in fluid isolation relative to the chamber 52.

The expansion nozzle 54 can be disposed at a distal end of the delivery conduit 32 and/or in any of a variety of positions along the cooling instrument 30, for example at its proximal end 48, its distal end 50, or any point therebetween. In one embodiment, the expansion nozzle 54 is disposed adjacent to a central portion of the cooling instrument 30, about half way between the proximal and distal ends 48, 50 thereof. The expansion nozzle 54 can also be disposed in a portion of the cooling instrument 30 configured to be positioned adjacent to a patient's spinal canal when the cooling instrument 30 is implanted in a vertebra of the patient (e.g., in a pedicle of the patient).

In implementations in which the coolant means is a chilled fluid, the fluid can be passed through the chamber 52 of the cooling instrument 30 to deliver a cooling effect thereto and to surrounding tissue. In one embodiment, the chamber 52 can be in the form of a fluid lumen having a first end coupled to the delivery conduit 32 and a second end coupled to the exhaust conduit 36. The chamber/fluid lumen 52 can optionally be coiled, snaked, or formed in some other tortuous, surface-area maximizing shape such that heat exchange to/from fluid that is directed through the chamber 52 can be optimized. The fluid can also simply enter the chamber 52 through the delivery conduit 32, reverse direction, and exit the cooling instrument 30 through the exhaust conduit 36.

In implementations in which the coolant means is a Peltier device, the Peltier device can be embedded inside cooling instrument 30 and electrical lines can be connected to the Peltier device internal to the cooling instrument 30. These electrical lines can extend from the cooling instrument 30 to a power source and optionally a regulator of the cooling effect, which can regulate the voltage or current on the electrical lines. In one embodiment, the power source and/or regulator can be disposed on or in the cooling instrument 30 or in another implantable unit.

The cooling instrument 30 can be cannulated, having a cannulation channel 46 extending along a central longitudinal axis of the cooling instrument 30 and extending all the way through an entire length of the cooling instrument 30. The cannulation channel 46 can allow the cooling instrument 30 to be inserted along an insertion aid such as a guide-wire, optionally in a minimally-invasive manner. The guide wire can be removed once the cooling instrument 30 has been inserted. It can be advantageous for the cannulation channel 40 to be axial and centered down the length of the cooling instrument 30, but this is not necessary. In other implementations, the cooling instrument 30 can only be partially cannulated for receiving the cooling means, or it need not be cannulated. Alternatively, or in addition, the cooling instrument 30 can have a groove in the longitudinal direction on its outer surface to be used in conjunction with an insertion aid that guides the cooling instrument 30 into the hole 22.

Figure 3B:
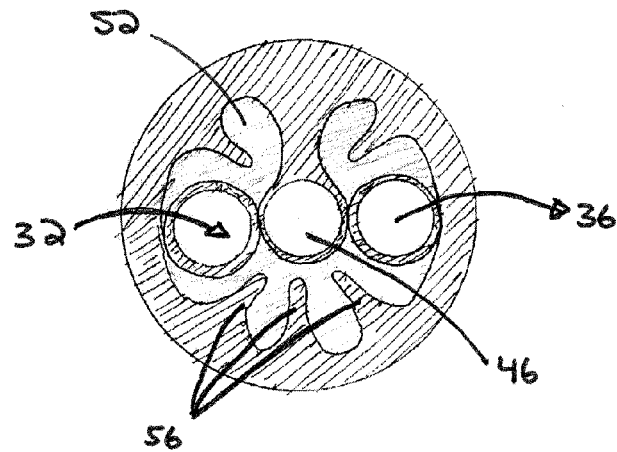
FIG. 3B is a lateral cross-sectional view of the spinal screw cooling instrument of FIG. 3A.

As shown in FIG. 3B, the cooling instrument 30 can optionally include a plurality of thermal fins 56 formed within the chamber 52. In the illustrated embodiment, the thermal fins 56 extend radially inward towards the cannulation channel 46 from an outer wall of the chamber 52. In use, an expanded gas or chilled fluid can circulate around and across thermal fins 56, which can improve the thermal conduction from the coolant means to the cooling instrument 30, and thus to the target tissue. The thermal fins 56 can also improve the mechanical strength of the cooling instrument 30. It will be appreciated that the thermal fins 56 can be oriented in a variety of directions, can be spiraling, and can take on a variety of shapes and sizes.

In some cases, it can be desirable to leave the cooling instrument 30 implanted in the patient for a longer period than the cooling process is conducted, and furthermore it can be desirable to completely close the patient's surgical wound after the delivery of the cooling effect is complete. To allow such uses, the delivery conduit 32, exhaust conduit 36, and/or sensor wire(s) 35 can be detachable from the cooling instrument 30, each individually, or all together. In one implementation, these conduits and/or wire(s) can be coupled to the cooling instrument 30 via a screw connection, and as such these conduits and/or wire(s) can be detached by unscrewing them. In other implementations, these conduits and/or wire(s) can be coupled to the cooling instrument 30 via a mechanical latch, screw, bolt, pin, or other piece of fastening hardware, and detaching these conduits and/or wires can require removing the hardware and/or an unfastening step. In other implementations, the coupling can be through a type of an interference-fit, transition fit, or clearance fit (including, but not limited to, a press fit and a ball-plunger fit), and pulling on the conduit and/or wire(s) with a sufficient force can cause detachment. For the delivery conduit 32 and the exhaust conduit 36, it is advantageous that the conduits be coupled to the cooling instrument 30 in such a way that the delivery of the cooling effect is not subject to leaks at the location of the coupling. To prevent such leaks, gaskets or other forms of seals can be used at the location where the conduits 32, 36 couple to the cooling instrument 30 and its inner lumen(s) or chamber(s).

Figure 3C:
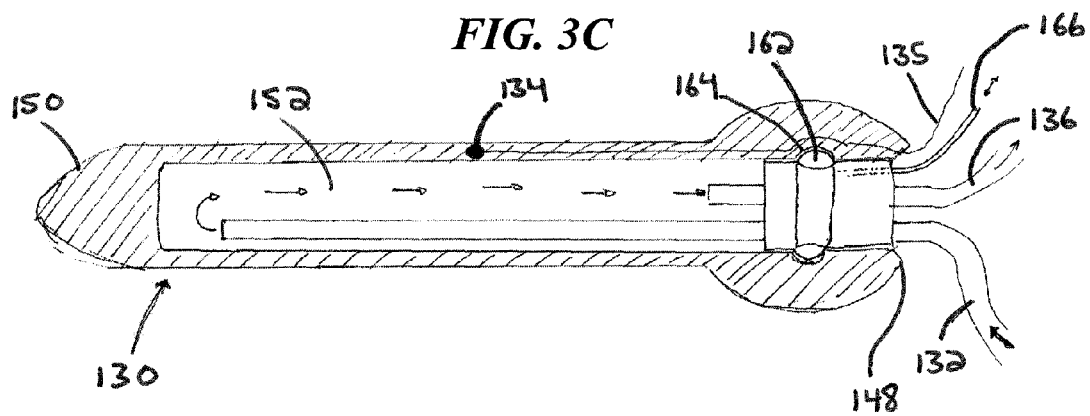
FIG. 3C is a longitudinal cross-sectional view of another embodiment of a spinal screw cooling instrument.

FIG. 3C illustrates an alternative embodiment of a cooling instrument 130 in which the delivery conduit 132 and the exhaust conduit 136 are coupled to the cooling instrument 130 and sealed via an inflatable cuff or coupling balloon 162. This inflatable cuff, when inflated, can create a seal with the cooling instrument 130 (e.g., with a corresponding annular recess 164 formed in a sidewall of the chamber 152 or in a sidewall of a cannulation channel). The inflatable cuff 162 can be deflated to release the seal as well as to unlock the conduits 132, 136 from their coupling with the cooling instrument 130 for detachment. In implementations in which the cooling means is either a pressurized gas or liquid, the inflatable cuff 162 can be inflated using the cooling means itself (and the pressure that is produced with it inside the cooling instrument 130 as well as the conduits 132, 136). In such cases, the inflatable portion of the inflatable cuff 162 can be in fluid communication with the inside of either the cooling instrument 130 or the conduits 132, 136, allowing the cooling means to also be delivered into the inflatable cuff 162. Once the delivery of the cooling effect has been completed, the pressure inside the cooling instrument 130 and the conduits 132, 136 can be released, and as a result, the inflatable cuff 162 can be deflated.

It will be appreciated that the inflatable cuff 162 can also have a separate dedicated conduit 166 which delivers a fluid to the cuff 162 to inflate it and keep it inflated. In any of the above implementations, the inflatable cuff 162 can be attached to the conduits 132, 136, can be an element of the cooling instrument 130, or can be a separable component of its own.

As also shown in FIG. 3C, the delivery conduit 132 can extend well into the chamber 152, terminating at a location adjacent to the distal end 150 of the cooling instrument 130. The exhaust conduit 136, on the other hand, can terminate only a small distance into the chamber 152, adjacent to the proximal end 148 of the cooling instrument 130. With this relative positioning of the conduit outlets, fluid introduced through the delivery conduit 132 must flow through substantially the entire length of the chamber 152 before being removed through the exhaust conduit 136. In this manner, the thermal transfer between the fluid and the cooling instrument 130 can be maximized and more evenly distributed along the length of the cooling instrument 130.

Figure 3D:
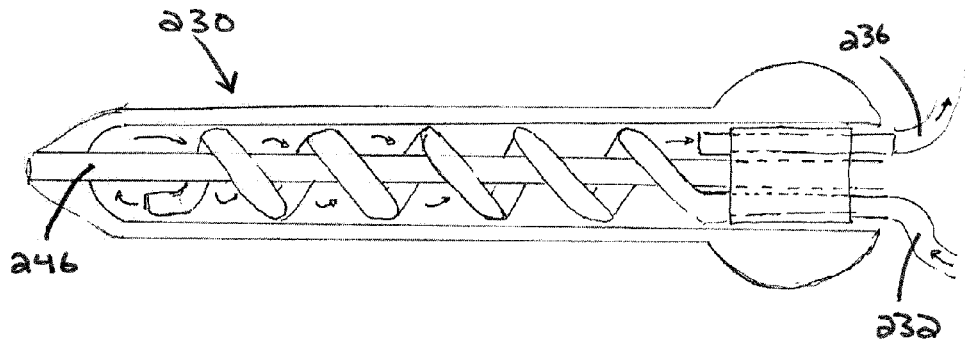
FIG. 3D is a longitudinal cross-sectional view of another embodiment of a spinal screw cooling instrument.

FIG. 3D illustrates another embodiment of a cooling instrument 230 in which the delivery conduit 232 is helically wound around the cannulation tunnel 246. This can advantageously improve thermal transfer between the delivery conduit 232 and the cooling instrument 230. In addition, the delivery conduit 232 can act as an internal baffle, routing fluid released from the distal end of the delivery conduit 232 along a helical path back towards the exhaust conduit 236, as shown with the illustrated arrows. Thus, thermal transfer can also be improved between fluid released from the delivery conduit 232 and the cooling instrument 230.

Figure 3E:
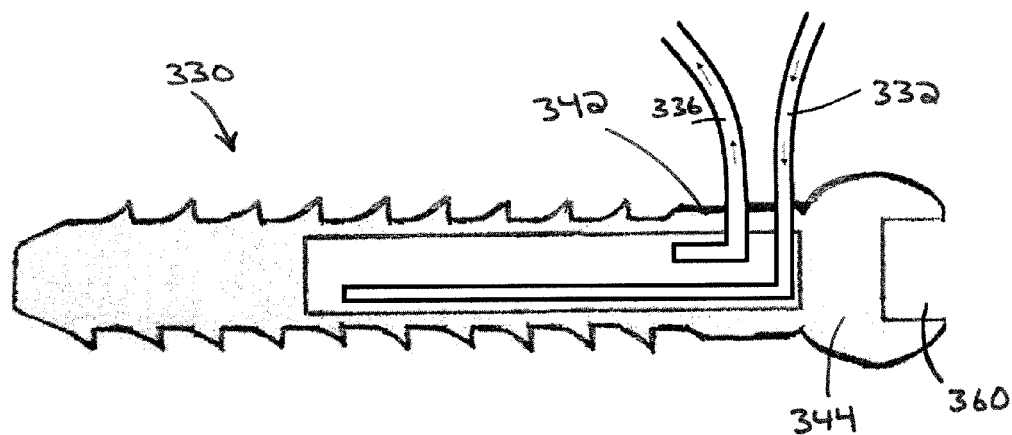
FIG. 3E is a longitudinal cross-sectional view of another embodiment of a spinal screw cooling instrument.

FIG. 3E illustrates another embodiment of a cooling instrument 330 in which the delivery and exhaust conduits 332, 336 are coupled to the neck portion 342 of the cooling instrument 330. In this configuration, the head portion 344 of the cooling instrument 330 can be coupled to various stabilization hardware and/or driving tools without interference from the conduits 332, 336.

Figure 3F:
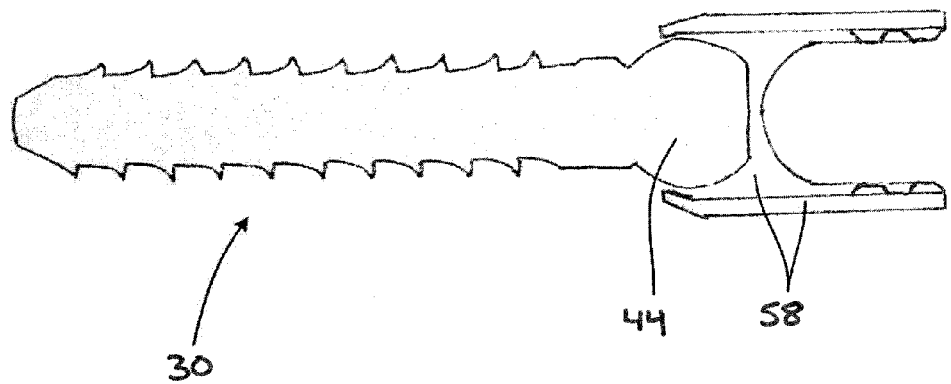
FIG. 3F is a side view of a spinal screw cooling instrument coupled to a rod-receiving member.

As shown in FIG. 3F, the head portion 44 of a cooling instrument (e.g., cooling instruments 30, 130, 230) can be used with other implants in spinal stabilization. Typical spinal stabilization hardware is made up of anchors (e.g., bone screws) that are implanted in vertebrae and interconnected by rods or other linkages. In one implementation, the head portion 44 is a poly-axial head, typical of spine stabilization hardware, meant to be coupled with a rod seat 58 to which a spinal rod can be mounted and used to connect multiple vertebrae for stabilization. Alternatively, the head portion 44 can be integrally formed with a rod receiving portion. The rod seat 58 can also be referred to as a "tulip." It will be appreciated that a variety of techniques can be used for coupling the cooling instrument 30 and, in particular, the head portion 44 to stabilization structures. The head portion 44 is an optional feature of the cooling instrument 30, and may not be necessary for applying a cooling effect.

In some implementations, the head portion 44 can be removable after the cooling instrument 30 has been inserted into the hole 22. Alternatively, the cooling instrument 30 may not include the head portion 44 when it is inserted into the hole 22, and the head portion 44 can be added to the cooling instrument 30 at a later point when it has been inserted into the hole 22. In implementations where the head portion 44 is removable, it can be added or removed from the cooling instrument 30 by securing it or removing it from the cooling instrument 30 through any number of securing means, such as a threaded connection between the two, or through using a fastening bolt.

The cooling instrument 30 can include a driving interface 60 (e.g., a socket or protrusion formed in or on a proximal end of the head portion 44) that accepts tools for driving the cooling instrument 30 into the hole 22. For example, the driving interface 60 can be configured to receive the tip of an Allen wrench, which can then be used for turning the cooling instrument 30 into the hole 22. The driving interface 60 can also be adapted to receive a screw-driver or torx wrench. Alternatively, the cooling instrument 30 can be driven into hole 22 by use of a socket wrench, in which case the driving interface 60 can include a hexagonal convex head which mates with the socket wrench. In one embodiment, the delivery conduit 32 and/or the exhaust conduit 36 can extend through the driving interface 60 and can be selectively coupled thereto. For example, the conduits 32, 36 can be coupled to a collar configured to form a friction or snap fit with a recess of the driving interface. In such implementations, the cooling instrument 30 can be driven into the hole 22 with the conduits 32, 36 removed using a tool mated to the driving interface 60. Once the cooling instrument 30 is positioned within the hole, the tool can be removed from the driving interface 60 and the conduits 32, 36 and/or a collar coupled thereto can be pressed into the driving interface 60, thereby placing the conduits 32, 36 in fluid communication with the chamber 52. The conduits 32, 36 can also be coupled to the driving interface 60 using an inflatable cuff as described above.

Figure 3G:
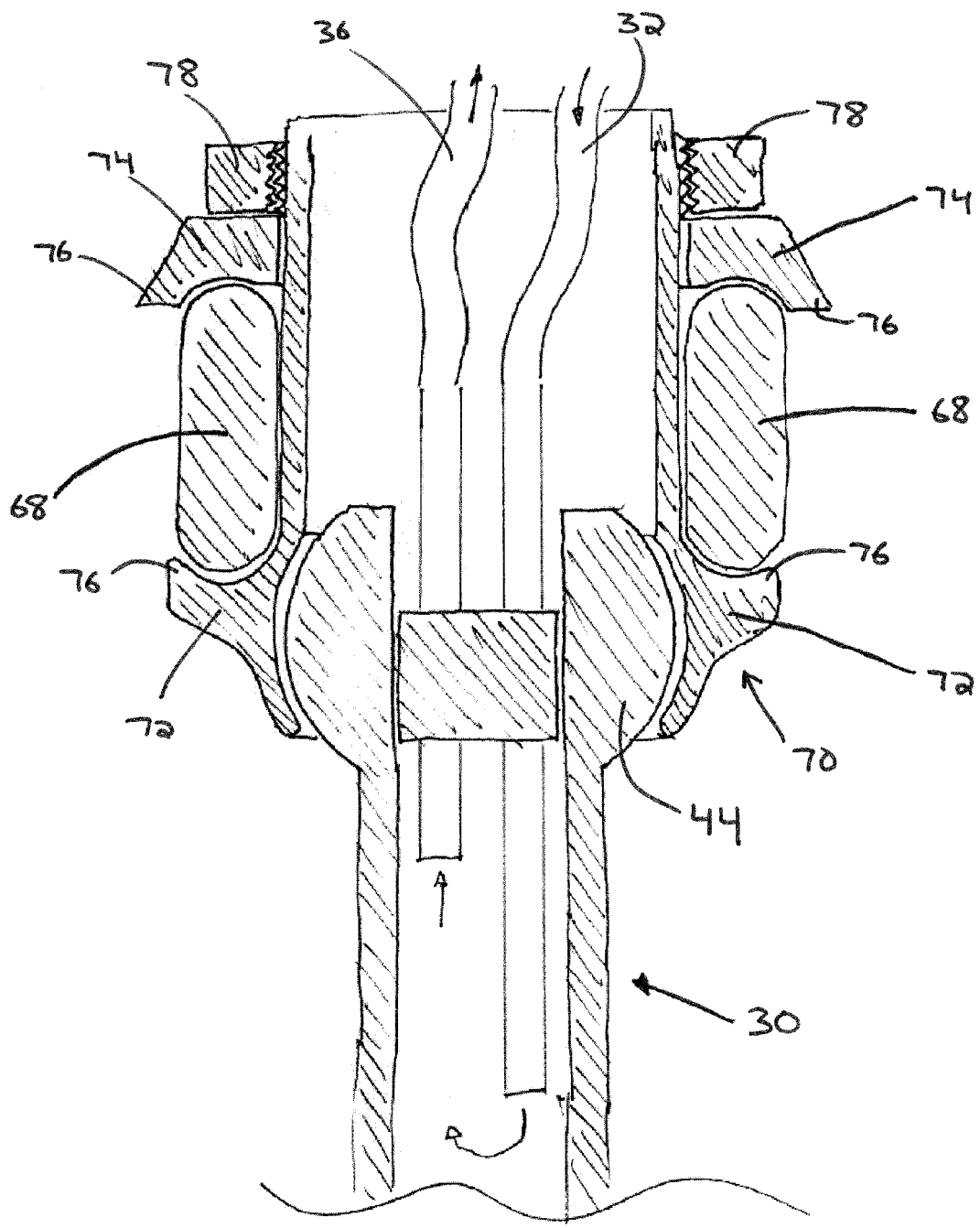
FIG. 3G is a cross-sectional view of a spinal screw cooling instrument coupled to a rod-receiving member, the rod receiving member having a split spinal rod secured thereto.

As shown in FIG. 3G, the cooling instrument 30 can be coupled to a split rod 68 to allow simultaneous stabilization/fixation and cooling without the rod 68 and the cooling conduits 32, 36 interfering with each other. For example, the head portion 44 of the cooling instrument 30 can be coupled to or formed integrally with a tulip 70 that is specifically designed to hold a split rod 68 for stabilization. In the illustrated embodiment, the tulip 70 includes first and second shelves 72 extending from an exterior sidewall thereof that are configured to receive and seat the longitudinal rails of the split rod 68. In one embodiment, the shelves 72 can be a single annular ridge that extends continuously around an outer circumference of the tulip 70. The split rod 68 can slide across the shelves 72 so that a position of the tulip 70 along the length of the split rod 68 can be adjusted.

Once the split rod 68 is positioned as desired, it can be locked to the tulip 70 via a locking cap 74 and nut 78, either or both of which can be threaded onto or otherwise secured to the tulip 70. As shown, the locking cap 74 and the shelves 72 can include protrusions 76 at their outer extremities that serve to capture and secure the split rod 68 when the construct is locked together. It will be appreciated that a split rod configuration can be accomplished in a number of different ways such that the rod 68 the tulip 70 do not interfere with the conduits 32, 36 and wires related to the cooling aspects of the apparatus.

Figure 4A:
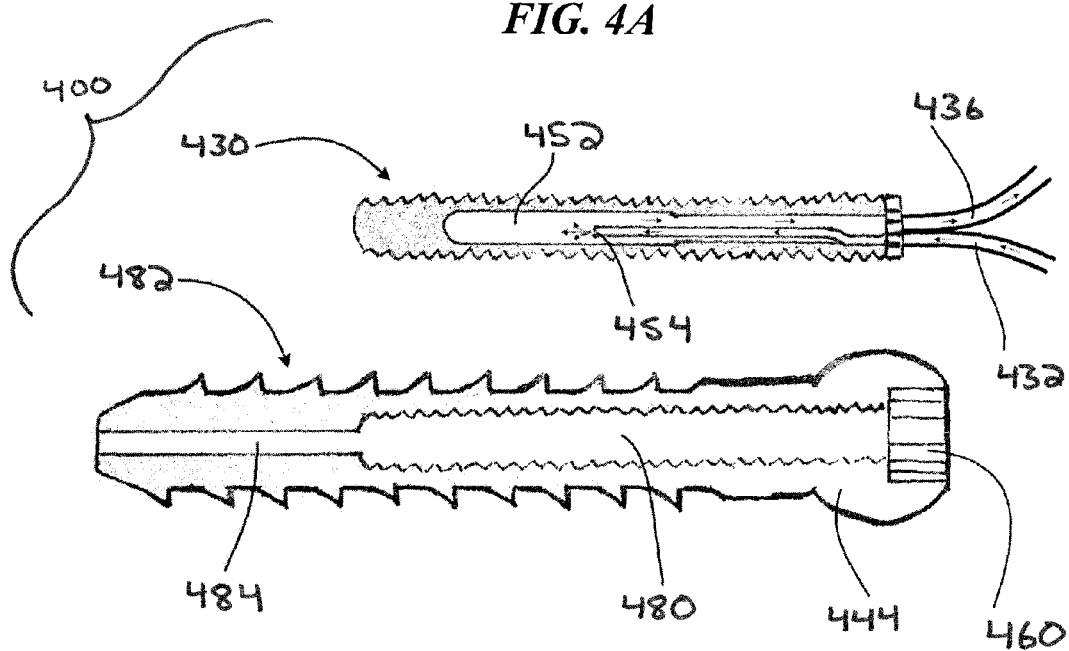
FIG. 4A is a longitudinal cross-sectional view of another embodiment of a cooling instrument in the form of a bone screw having an insert disposed therein.

FIG. 4A depicts a cross-section of an alternative embodiment of a cooling instrument 400 in the form of a bone screw 482 having a removable insert 430 disposed therein and configured to receive the coolant means. The bone screw 482 can be anchorable within the hole 22 via a threaded exterior surface. It will be appreciated that the bone screw 482 can be anchored in other ways besides threads, including friction, suction, barbs, expansion of rigid elements, bonding etc. The bone screw 482 can also have a smooth surface, a ribbed surface, a dimpled surface, or any other type of surface. Once the bone screw 482 is inserted into the hole 22, the insert 430 can be delivered into the cavity 480 of the bone screw 482. Preferably, the cavity 480 is threaded to receive a threaded outer surface of the insert 430 and securely hold the insert 430. It will be appreciated that other techniques and designs can be used to securely hold the insert 430 in the cavity 480, such as friction, latches, spring-loaded stops, etc. The insert 430 can also be in the form of a balloon or other inflatable object that can be secured within the bone screw 482 by inflation. Once the insert 430 is inserted into cavity 480, the insert 430 can provide the cooling effect. It will be appreciated that the insert 430 can already reside in the cavity 480 prior to the insertion of the bone screw 482 in the hole 22.

The bone screw 482 can include a cannulation channel 484 which can aide insertion of the bone screw 482 into the hole 22, by allowing the bone screw 482 to be guided down a thin wire or rod that is inserted into the hole 22. The wire can be subsequently removed by pulling it through the cannulation channel 484 and out of the patient. The cavity 480 and the cannulation channel 484 can be positioned axially on the bone screw 482, in which case the cannulation channel 484 can be an extension of the void of the cavity 480. The cannulation channel 484 can also be co-located and/or the same as the cavity 480.

Similar to the insertion of the cooling instrument 30 described above, the bone screw 482 can be inserted into the hole 22 through a variety of means. Preferably, the bone screw 482 has a driving interface 460 coupled thereto or formed therein or thereon that accepts tools for driving the bone screw 482 into the hole 22. In implementations in which the bone screw 482 has a threaded cylindrical surface, the driving interface 460 can include of a small void for receiving the tip of an Allen wrench, which can be used for turning the bone screw 482 into the hole 22. Alternatively, the driving interface 460 can be adapted to receive a screw-driver or torx wrench, or the bone screw 482 can be driven into the hole 22 by use of a socket wrench, in which case the bone screw 482 can have a hexagonal convex head which mates with the socket wrench.

Having the bone screw 482, which is installed into the hole 22, separable from the insert 430 which, when in use, resides in the cavity 480 of the bone screw 482, allows the bone screw 482 to be used for alternative purposes. In particular, the bone screw 482 can be used as one part of a multi-part stabilization structure implanted across multiple vertebrae. As such, the bone screw 482 can include a stabilization head 444, similar to the head portion 44 of the cooling instrument 30 described above. The stabilization head 444 of the bone screw 482 can be coupled to additional stabilization hardware typical of spine stabilization procedures. Once the insert 430 is no longer needed to deliver its cooling effect, it can be removed from the bone screw 482, and, if needed, additional stabilization hardware, such as a rod seat and one or more spinal rods can be coupled to the stabilization head 444. Alternatively, some of this additional hardware can already be coupled to the bone screw 482 and the stabilization head 444 prior to the bone screw 482 being inserted into the hole 22. It will be appreciated that the stabilization head 444 is an optional feature of the bone screw 482. Just the same, a variety of stabilization hardware can come coupled to the bone screw 482 when in use with the insert 430.

In some embodiments, the stabilization head 444 may not be part of the bone screw 482, but rather part of a stabilization-insert that is inserted into the cavity 480 when the insert 430 has been removed. The stabilization-insert can be used to attach the apparatus to a rod for stabilizing it relative to other vertebrae typical of known spine stabilization and fixation techniques. The stabilization-insert can have a threaded surface to match a threaded inside surface of the cavity 480.

Figure 4B:
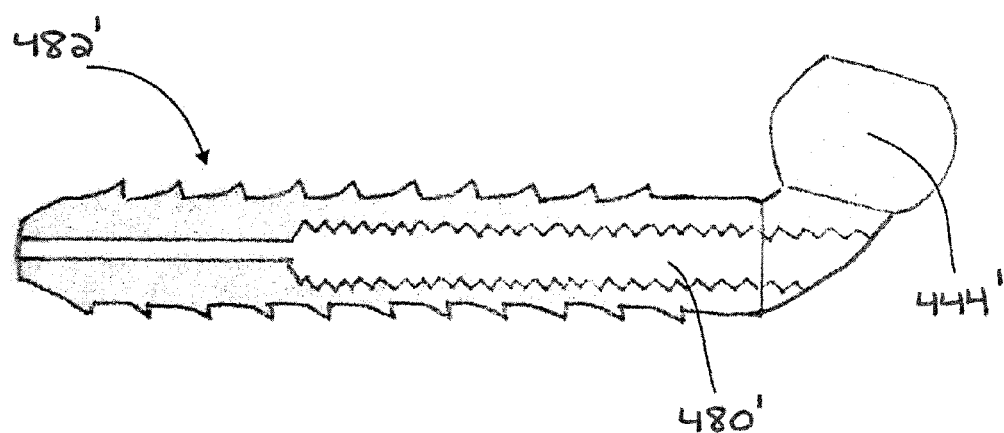
FIG. 4B a longitudinal cross-sectional view of a spinal screw cooling instrument having an offset head orientation.

FIG. 4B depicts a bone screw 482' with a stabilization head 444' that is offset from the center axis of the bone screw 482'. Such a configuration can be advantageous when it is intended to both stabilize the spine as well as cool the spinal cord simultaneously. Having the stabilization head 444' off-axis allows for the stabilization hardware and the cooling hardware, such as the coolant delivery and exhaust conduits, to not interfere. This same stabilization head configuration of FIG. 4B, as it applies to the bone screw 482', can equally apply to any of the cooling instruments described herein.

It will be appreciated that in implementations in which the hole 22 is in a pedicle 12, the hole 22 can extend into the vertebral body 10. As such, the bone screw, insert, and/or stabilization-head insert can each extend into the vertebral body 10.

It will be appreciated that the instruments and hardware described are able to be produced using common practices known to those skilled in the art of hardware manufacturing and specifically surgical device manufacturing.

The cooling instruments, inserts, and related hardware disclosed herein can be formed from any of a variety of thermally-conductive, medical-grade, and/or implantable materials such as metals, plastics, ceramics, and the like. Metals typically have high thermal conductivity which is advantageous for the implementation of the cooling instrument, as it provides for rapid conduction of the cooling effect. Secondly, metal typically has high physical strengths (e.g. tensile, shear, compressive) which is advantageous as it reduces risks of fracture or deformation, and in addition, allows the cooling instrument to be used as part of a spinal column stabilization structure. Metal also is able to be readily sterilized, a critical attribute of human implants. In one embodiment, the cooling instrument can be formed from biocompatible titanium or stainless steel.

The size (e.g., length, diameter, thread pitch, thread depth, etc.) of the cooling instrument can be selected based on a variety of factors, including the dimensions of the bone structure to which the cooling effect is to be applied, the age, sex, or species of the patient, and/or the degree of cooling required.

Transosseous Process and Operation

Figure 5:
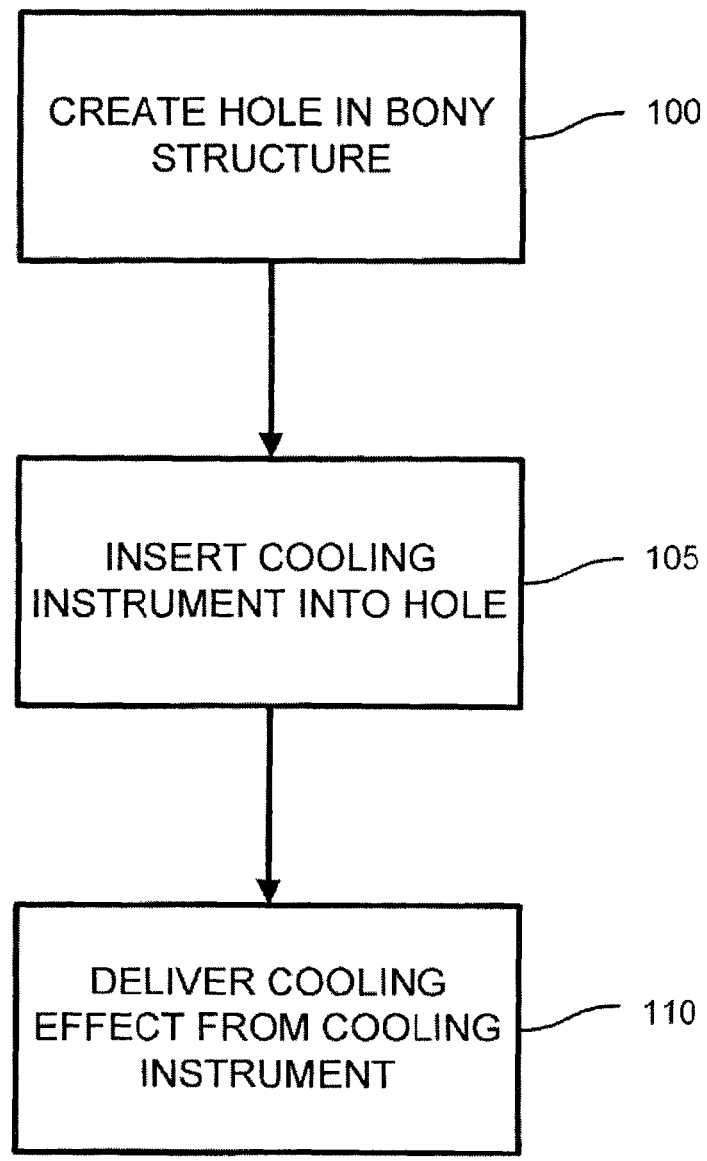
FIG. 5 is a flow chart of a process for cooling tissue using a cooling instrument.

FIG. 5 is a flow chart of one exemplary method of cooling tissue. While various methods disclosed herein are shown in relation to a flow chart or flow charts, it should be noted that any ordering of method steps implied by such flow charts or the description thereof is not to be construed as limiting the method to performing the steps in that order. Rather, the various steps of each of the methods disclosed herein can be performed in any of a variety of sequences. In addition, as the illustrated flow charts are merely exemplary embodiments, various other methods that include additional steps or include fewer steps than illustrated are also within the scope of the present invention. Furthermore, two or more of the illustrated steps can be performed simultaneously. Before executing the process of FIG. 5, access to a vertebra is obtained, for example using an open or minimally-invasive surgical technique to form a tissue opening through which the vertebra can be accessed. In step 100, a hole is created in a bony structure of the vertebra. In one aspect, the hole is created using a drill and a drill bit, but it should be recognized that this hole can be created in a variety of ways, including by a self-drilling screw or cooling instrument, or by the insertion of a sharp wire.

It can be desirable to create the hole of step 100 in a bony structure such that the hole, in its length, sits tangentially to and in close proximity to the spinal canal. Such proximity to the spinal canal allows for the conduction of the cooling effect to the contents of the spinal canal in a later step. The hole created in step 100 preferably stays within the bone wall confines of the bone in which it is created. In some implementations, where the hole is created in bony structures adjacent to the spinal canal, breaching the wall boundary of the bone adjacent to the spinal canal can potentially disrupt the contents of the spinal canal and cause injury. It will be appreciated, however, that there may be cases where it is desirable to just barely breach the surface of the boney walls adjacent to the spinal canal so long as doing so does not injure the adjacent soft tissue, so that the inserted cooling instrument (per step 105) can be very close to the contents of the spinal canal as well as to make contact with the cortical bone of the bony structure so as to utilize its structural properties. Furthermore, there can be specific interests in creating a hole that extends beyond a bone structure's wall boundary on its distal end.

In one embodiment, the bony structure for step 100 refers to a pedicle of the posterior arch of a vertebra. In alternative implementations, alternative bony structures surrounding the posterior arch of the vertebra, including the vertebral lamina and the spinous process, can have the hole of step 100 created therein. In still alternative implementations, as described below, the hole can be created more laterally than the pedicle, such as in the approach taken in a lateral mass screw placement procedure.

The step 100 of creating a hole in a bony structure takes advantage of the fact that the bony structure is rigid, allowing the hole to be formed easily and consistently. If the bone was not rigid, it would be difficult to form a hole in it by drilling as it can deform due to the pressures exhibited by the drilling process. If the bone was not rigid, it would be difficult to accurately form a hole in it of a certain depth as a lack of rigidity would allow it to deform and compress. As such, the rigidity of the bone allows the hole to be accurately and precisely created allowing a cooling instrument to be located near a targeted tissue consistently and accurately in step 105.

In step 105, a cooling instrument is advanced through the tissue opening and inserted into the hole created in step 100. As noted above, the cooling instrument can be a single piece of hardware, or can include a removable insert that is selectively positionable within a bone screw, allowing the bone screw to later remain in the hole while the insert is separated and removed from the bone screw and the hole the bone screw is in. The insertion of the cooling instrument into the hole can include insertion of the insert into the cavity of a bone screw which is inserted into the hole.

The cooling instrument can be threaded into the hole. In such a case, the instrument can have a driving interface to allow insertion to be facilitated by a driving tool such as an Allen wrench, a screw driver, or a torx wrench. Alternatively, the instrument can be driven into the hole through direct continuous pressure or through a pounding of the instrument.

The cooling instrument is inserted into the hole preferably a distance such that the cooling instrument's cooling delivery to the spinal canal is maximized. In particular, the distance of insertion can be selected such that the cavity of the cooling instrument, or a portion thereof, is positioned adjacent or in close proximity to the portion of the hole nearest to the spinal canal. Such a position can maximize the efficiency of delivering the cooling effect across the bone wall to the spinal canal contents.

In step 110, the cooling effect is delivered from the cooling instrument, for example by expanding gas through the cooling instrument causing it to rapidly cool itself and the tissues adjacent to it. Alternatively, other coolant means can be used besides gas expansion, including circulating chilled fluid through the cooling instrument, as well as powering a Peltier device in the cooling instrument. The delivery of the cooling effect, in some implementations, includes delivering the coolant means from a coolant source, such as a tank of compressed gas. In this step, the tank of compressed gas can be opened such that the compressed gas flows through a tube (e.g., a coolant delivery conduit) to the cooling instrument. Preferably, the tank includes a regulation or control unit that controls how much and how fast compressed gas is delivered to the cooling instrument. The control unit can simply be a manually operated valve, in which case the delivering of the cooling effect is initiated by manually opening the valve. The control unit can also include a computer-controlled valve that uses either pre-programmed data or perioperatively-measured data to determine how much of a cooling effect should be delivered.

For instance, the control unit can read data from a temperature sensor placed intrathecally, and when the intrathecal temperature is reduced below a threshold value, the control unit can begin to limit or turn off the delivery of the cooling effect. When the intrathecal temperature rises above the temperature threshold, the control unit can begin delivering the cooling effect again. It will be appreciated that any number of physiological characteristics (as previously mentioned), both quantitative and qualitative, can be used as input to the control unit for the purposes of controlling the delivery of the cooling effect.

The cooling instrument can remain implanted in the patient for only the duration of the delivery of the cooling effect, or can remain implanted in the patient after the surgical wound has been closed up, and even can remain in the patient for the remainder of the patient's life. In an implementation where the cooling instrument is also used as part of spine stabilization structure, it can be advantageous to leave the cooling instrument implanted in the patient for at least a year.

It will be appreciated that the steps described above can be repeated for a plurality of cooling instruments, each of which can be positioned in different positions within a patient's vertebrae. In one exemplary embodiment, a first cooling instrument is implanted in a first pedicle of a first vertebra and a second cooling instrument is implanted in a second, contralateral pedicle of the first vertebra. Cooling instruments can also be implanted in multiple vertebral levels of the patient's spine, and any number of cooling instruments can be implanted in a single vertebra. In one embodiment, a location of spinal injury is determined and cooling instruments are implanted into one, two, or three vertebrae superior to the location of spinal injury. In another embodiment, cooling instruments are implanted into the vertebrae that are immediately superior and inferior to the site of the spinal injury.

As described above, after completion of the process of FIG. 5, additional stabilization hardware can be coupled to the cooling instrument to stabilize the patient's spine. For example, a spinal rod or other fixation device can be coupled to the cooling instrument.

Alternative Approaches

Figure 6:
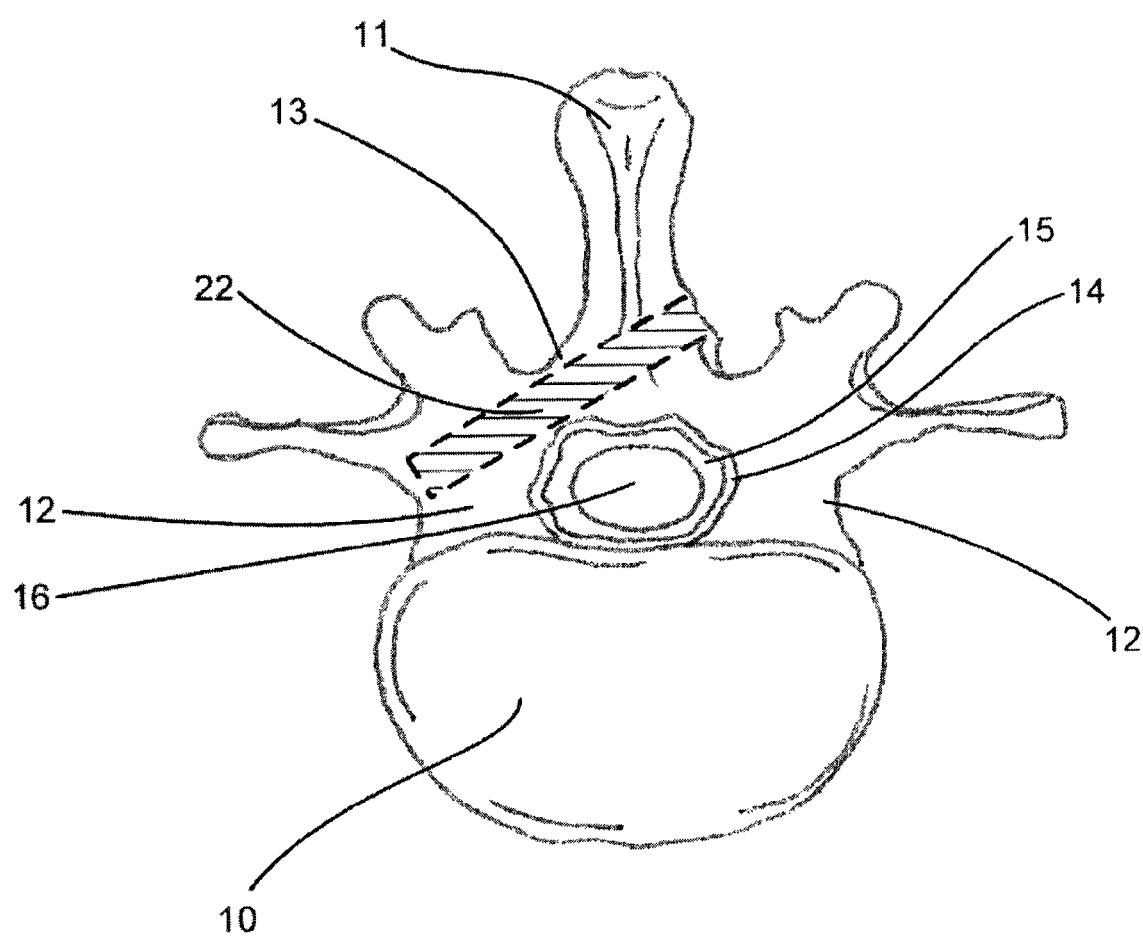
FIG. 6 is a transverse sectional view of a vertebra, the vertebra including a trans-laminar hole for implanting a cooling instrument.

In an alternative approach, as depicted in FIG. 6, the hole 22 can be created with a trans-laminar approach where the hole 22 is created through the lamina 13 of a vertebra. It should be recognized that by referring to the lamina 13, either lamina of a vertebra can be used. Such a configuration of the hole 22 can allow for a cooling instrument to be inserted into the hole 22 and to be positioned adjacent to the spinal canal 14. The bony structures of the spinous process 11 and the lamina 13 can be used as landmarks for placing a cooling instrument near the spinal canal 14 and its contents 15. Creating the hole 22 in such a location and having a trajectory similar to what is depicted in FIG. 6 provides a means for placing a cooling instrument near soft tissue reliably without disturbing the soft tissue itself. In this embodiment, the soft tissue is the spinal canal contents 15, including the spinal cord 16.

Figure 7:
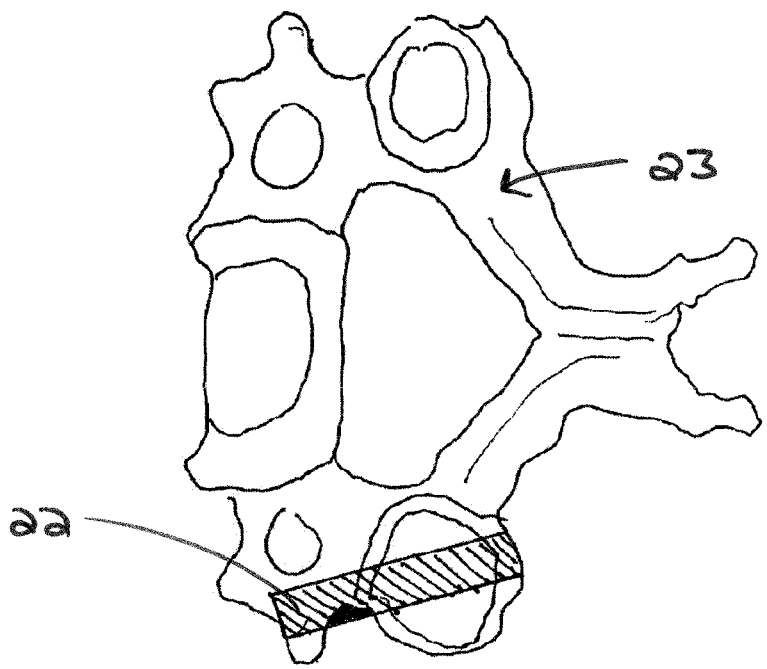
FIG. 7 is a transverse sectional view of a vertebra, the vertebra including a laterally-positioned hole for implanting a cooling instrument.

As shown in FIG. 7, in creating the hole 22 in the vertebra 23, a more lateral approach than a pedicular approach can be used, such as an approach typically used in implanting lateral mass screws. Such an approach can be advantageous for particular patient injuries and/or anatomical geometries, yet provides many of the benefits of the pedicular approach as described herein. In particular, this approach can be advantageous in the cervical levels of the spine and where there is concern of disrupting the vertebral artery as it passes through the foramen transversarium.

A cooling effect can alternatively be delivered through a laminar hook approach, where the hook surfaces and hook body act as the conductive platform for cooling the tissues of the spinal canal, including the spinal cord. In such an implementation, the coolant means can be introduced into a laminar hook via a conduit. If the coolant means is a chilled liquid, the chilled liquid can be delivered by the conduit, and circulated through a lumen or lumens on the inside of the hook. Alternatively, if the coolant means is an expanding gas, the expanding gas can be delivered by the conduit, and expanded across a nozzle into an expansion chamber inside the laminar hook.

Figure 8:
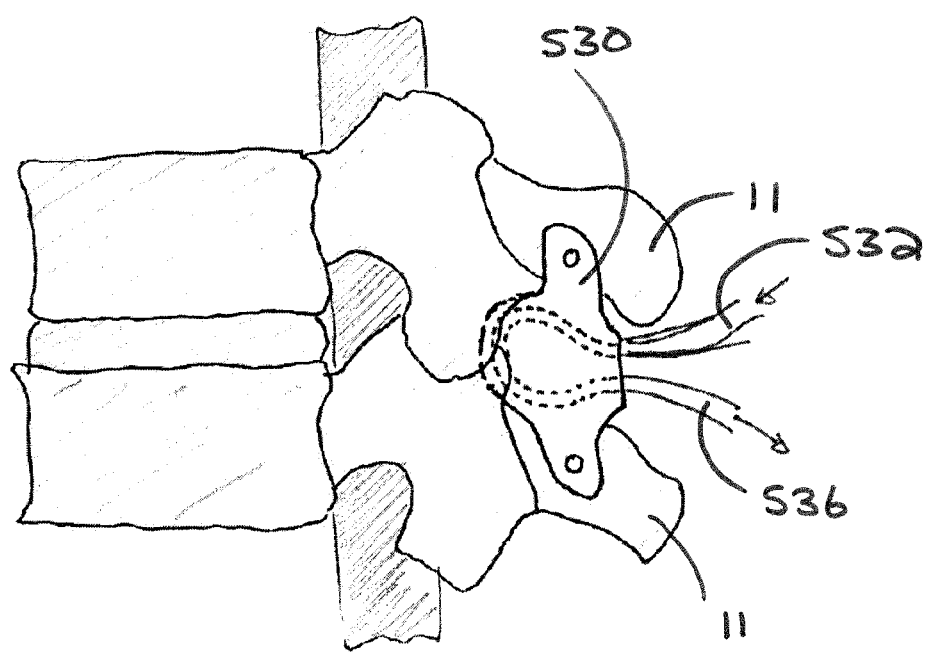
FIG. 8 is a lateral view of two vertebrae having a spinous process spacer cooling instrument positioned between the spinous processes thereof.

Similarly, as shown in FIG. 8, a cooling effect can be delivered through an instrument 530 that can be attached to and fitted between two adjacent spinous processes 11. The instrument 530 can serve as an interspinous process spacer or interspinous process fixation device. Such a placement of the cooling instrument allows the instrument to be placed in close proximity to the tissues of the spinal canal, including the spinal cord. The instrument 530 can include a delivery conduit 532 and an exhaust conduit 536, and can include any of the features or characteristics described herein with respect to other embodiments of cooling instruments.

A cooling effect can also be delivered through a facet screw approach.

Many of the implementations described herein can advantageously be coupled with a stabilization and fixation structure, such as rods or other similar structures. These rods too can be used to deliver a cooling effect to their surrounding tissues, including the tissues of the spinal canal and the spinal cord. Because of the variety of locations the rods can be placed, they can also be used to cool muscular tissues that are more lateral or posterior from the spine.

Figure 9:
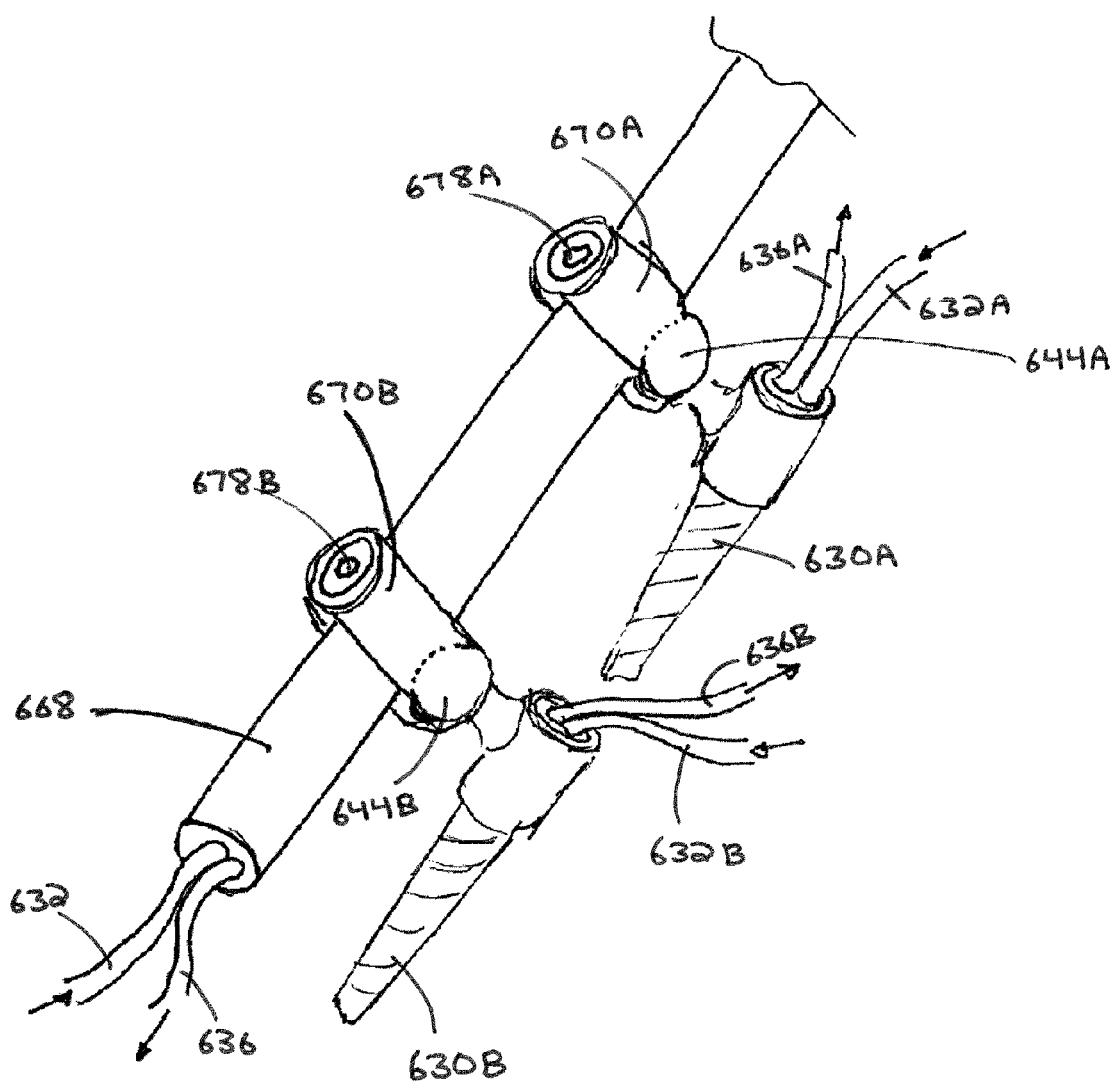
FIG. 9 is a schematic view of a spinal rod cooling instrument coupled to two bone screw cooling instruments.

FIG. 9 illustrates one exemplary embodiment of a rod 668 that is configured to deliver a cooling effect. The rod 668 can include a delivery conduit 632 through which a chilled fluid or compressed gas can be supplied to a chamber formed within the rod 668. The rod 668 can also include an exhaust conduit 636 through which expanded gas or circulated fluid can be evacuated from the chamber. In the illustrated embodiment, the rod 668 is anchored to the spine using first and second cooling instruments 630A, 630B, each of which include a polyaxial head portion 644A, 644B seated within a tulip 670A, 670B in which the rod 668 is received and locked by a set screw 678A, 678B. Each of the cooling instruments 630A, 630B also have their own delivery conduits 632A, 632B and exhaust conduits 636A, 636B. The delivery conduits 632, 632A, 632B can be bridged, bussed, or coupled together such that a common supply source can be used. The same is true for the exhaust conduits 636, 636A, 636B. It will be appreciated that the cooling rod 668 can also be used with traditional bone screws or anchors that do not have their own cooling capabilities, in which case the rod 668 can be the sole source of cooling.

It will be appreciated that more than one of the cooling instruments, as described herein, can be used at one time, and further, multiple different types of cooling instruments can be used at the same time. For example, a pedicular cooling instrument can be used in conjunction with an intervertebral cooling instrument along with cooling rods. In some cases, and in particular where rods are being used, the multiple instruments can share conduits and sensor wires, and can have interconnecting chambers or lumens so that a potentially singular delivery of the coolant means addresses multiple instruments. In addition, any of a variety of existing implants, bone screws, etc. can be retrofitted to include a cooling device. For example, a cooling instrument can be provided in accordance with the principles disclosed herein that can fit within the cannulation of an existing bone screw. By way of further example, a cap having delivery and exhaust conduits coupled thereto can be attached and sealed to existing cannulated bone screws, in which case the existing cannulation of the bone screw can be used as the cooling chamber.

Exemplary Transosseous Implementation

As an illustrative example of a transosseous implementation, a pedicle of a vertebra is accessed percutaneously through a tissue opening. A hole is drilled into that pedicle in an axial trajectory towards, and possibly into, the vertebral body. Ideally, the hole is drilled in a parallel trajectory of the pedicle axis, but offset or off-center from the axis such that the wall that bounds the hole is very thin on the side of the spinal canal. Into that hole, a bone screw is threaded. The bone screw has a conical tip, a threaded cylindrical surface, and a socket to facilitate the driving of the bone screw into the hole. The bone screw also is cannulated with an axial hole to facilitate the insertion of the bone screw down a guide wire. A driver, such as a screw driver or Allen wrench, either powered, or manual, is coupled to the socket of the bone screw and used in combination to drive the bone screw and thread it into the hole.

Once the bone screw is implanted into the hole, an insert is then inserted into a cavity of the bone screw. This cavity, like the cannulation, is axial, and as such is connected with the cannulation, or is a part of the cannulation. The insert is secured into the cavity of the bone screw by the friction of a press fit.

The insert is connected to a regulated tank of compressed gas via a conduit that delivers the compressed gas to the insert. A second conduit exhausts the gas from the insert to a collection system or to the atmosphere. The insert has an expansion chamber inside of it, where the compressed gas it receives is expanded through an expansion nozzle. When it expands, it cools, and cools the surrounding insert. Once expanded, it is exhausted out the exhaust conduit.

The insert is inserted into the bone screw to a depth such that at least part of the expansion chamber is located at the depth in the cavity closest to the spinal canal and spinal cord.

The insert also has embedded in it a temperature sensor that measures the temperature of the metal of the insert near the expansion chamber. This embedded temperature sensor, via wires, provides temperature data that can be used to regulate the delivery of the compressed gas to the insert, and thus used to control the delivery of the cooling effect of the insert.

Additionally, a temperature probe is inserted near the spinal cord to measure the temperature of tissue proximate to the spinal cord. This temperature information is relayed via wires to a control unit and used to either display for manual control and regulation of the delivery of the gas, or used to automatically control the delivery of the gas. These two temperature measurements can be used in conjunction with each other for this control.

At the start of the cooling procedure, gas is delivered at a predetermined rate to the insert, and its temperature is monitored. The delivery of the gas is regulated, and the rate of gas delivered to the insert is either increased or decreased until the temperature of the insert is reduced to a predetermined temperature. The delivery of the gas is continually regulated to maintain that predetermined temperature at the insert.

As the insert begins to cool the bone screw and the surrounding tissue, including the spinal cord, the temperature of the tissue proximate to the spinal cord is monitored. When the temperature of the tissue proximate to the spinal cord is reduced to a predetermined level, the regulation of the cooling is continually adjusted to decrease (or increase) the delivery of gas to the insert in order to maintain the predetermined temperature at the tissue proximate to the spinal cord.

After a predetermined period of time, the delivery of gas to the insert is slowly reduced, and the temperature of the tissue proximate to the spinal cord is allowed to slowly return to its normothermic level.

Once the cooling procedure has completed, and the delivery of gas to the insert has been reduced fully to deliver no gas, the insert is removed from the bone screw.

The bone screw, in addition to being able to house the insert, can also have a poly-axial head for spinal stabilization purposes. The rod seat is fixated on the poly-axial head in an orientation desirable for the particular stabilization needed. Onto this poly-axial head, a rod seat, or "tulip", is attached into which a rod is placed and secured. This rod connects the bone screw to other bone screws or unrelated pedicle screws that are used in the stabilization structure, and thus puts a load on the bone screw as it is secured in the pedicle.

Alternative Exemplary Transosseous Implementation

As an alternative illustrative example of a method of cooling tissue, a pedicle of a vertebra is accessed percutaneously. A hole is created via a drill, awl, or other method, into the pedicle in an axial trajectory towards, and possibly into, the vertebral body. Ideally, the hole is created in a parallel trajectory of the pedicle axis, but offset or off-center from the axis such that the wall that bounds the hole is very thin on the side of the spinal canal. Into that hole, a cooling instrument is threaded. The cooling instrument, resembling a screw, has a conical tip, a threaded cylindrical surface, and a socket to facilitate the driving of the instrument into the hole. The instrument also is cannulated with an axial hole to facilitate the insertion of the instrument down a guide wire. A driver, such as a screw driver or Allen wrench, either powered, or manual, is coupled to the socket of the instrument and used in combination to drive the instrument and thread it into the hole. The cooling instrument is driven into the hole a distance where at least a portion of the cooling instrument that is cooled more effectively is proximal to the portion of the pedicle closest to the spinal canal (e.g. the section of the screw where the circulating lumen is located is positioned in the hole such that it is proximal to where the spinal canal is).

The cooling instrument is connected to a variable flow-rate pump via a conduit that delivers a chilled saline solution to the cooling instrument. The pump pumps the chilled saline solution from a refrigerated basin having a controllable temperature. In some cases, it is desirable to keep the saline solution in the basin near 0 degrees C., while in other cases it is desirable to keep the chilled saline solution in the basin cooler or warmer. The cooling instrument has a circulation lumen inside of it, where the chilled saline solution it receives is circulated through the lumen, effectively cooling the cooling instrument down. The pressure created by the pump in the delivery of the chilled saline solution to the cooling instrument forces the chilled saline solution through the cooling instrument. In some cases the cooling instrument will have multiple lumens for circulation of the chilled saline solution. In some cases, the lumen(s) will be arranged such that internal surface area is maximized as to improve thermal conduction between the cooling instrument and the chilled saline solution—for example the lumen can be spiral in nature so as to extend the effective length of the lumen. Once circulated, the chilled saline solution is exhausted via a second conduit back to the basin.

The cooling instrument also has embedded in it a temperature sensor that measures the temperature of the metal of the cooling instrument, and in particular, this temperature sensor is located in a portion of the cooling instrument that is proximate to the spinal canal (or at least at a proximate height along the cooling instrument's axis). This embedded temperature sensor, via wires, provides temperature data that can be used to regulate the delivery of the chilled saline solution to the cooling instrument by using it to adjust pump rate and temperature of the chilled saline in the basin, and thus used to control the delivery of the cooling effect of the instrument.

Additionally, a temperature probe is inserted near the spinal cord to measure the temperature of tissue proximate to the spinal cord. This temperature information is relayed via wires to a control unit and used to either display for manual control and regulation of the delivery of the chilled saline solution, or used to automatically control the delivery of the chilled saline solution. These two temperature measurements can be used in conjunction with each other for this control.

The cooling instrument also has a poly-axial head for spinal stabilization purposes. The rod seat is fixated on the poly-axial head in an orientation desirable for the particular stabilization needed. Onto this poly-axial head, a rod seat, or "tulip", is attached into which a rod is placed and secured. This rod connects the cooling instrument to other cooling instruments or unrelated pedicle screws (or other fixation instruments) that are used in the stabilization structure, and thus puts a load on the cooling instrument as it is secured in the pedicle. After the stabilization structure has been secured, the surgical wound can be partially closed up, leaving it just open enough for the conduits and wires related to the cooling procedure to remain passing through the wound opening.

At the start of the cooling procedure, chilled saline solution is delivered at a predetermined rate to the cooling instrument, and its temperature is monitored. The delivery of the chilled saline solution is regulated, and the rate and/or temperature of chilled saline solution delivered to the cooling instrument is either increased or decreased until the temperature of the cooling instrument is reduced to a predetermined temperature. The delivery of the chilled saline solution is continually regulated to maintain that predetermined temperature at the cooling instrument.

As the cooling instrument begins to cool the surrounding tissue, including the spinal cord, the temperature of the tissue proximate to the spinal cord is monitored. When the temperature of the tissue proximate to the spinal cord is reduced to a predetermined level, the regulation of the cooling is continually adjusted to decrease (or increase) the delivery of chilled saline solution to the cooling instrument in order to maintain the predetermined temperature at the tissue proximate to the spinal cord.

After a predetermined period of time, the delivery of chilled saline solution to the cooling instrument is slowly reduced, and the temperature of the tissue proximate to the spinal cord is allowed to slowly return to its normothermic level.

Once the cooling procedure has completed, and the delivery of chilled saline solution to the cooling instrument has been reduced fully to deliver no chilled saline solution, the conduits are evacuated of their remaining saline solution and the conduits and the sensors wires are detached from the cooling instrument and removed from the patient. The remainder of the surgical wound can then be closed up, leaving the cooling instrument along with any stabilization structure coupled thereto in the patient's spine area.

Intervertebral Approach

Cooling of the spinal canal, spinal cord, nerve roots, and other tissue can also be achieved with intervertebral cooling devices. Such devices can be used in spinal stabilization and intervertebral body fusion and for providing a cooling effect to the nervous tissues of the spine. Such devices can include intervertebral spacers, which are also known as interbody devices, interbody cages, disc replacement members, or disc replacement implants. The devices described herein have the ability to cool regions of the spine, as well as provide structural stability to the spine during cooling and the duration of the fusion of vertebral bodies.

The use of intervertebral spacers is common in the field for structural support of adjacent vertebral bodies after intervertebral disc removal and for promoting the fusion of the adjacent vertebral bodies. The subject matter described herein describes an approach for cooling tissues in and around the spine, including the spinal cord, using an intervertebral spacer as a platform for delivering the cooling effect, including aspects of the intervertebral spacer that allow it to advantageously be installed and act as a cooling platform or provide the cooling effect.

Surgical placement of an intervertebral spacer in a patient with spinal cord injury is a common procedure to help reconstruct an unstable spine. Using the devices and methods described herein has the advantages of still providing the functions and benefits of an intervertebral spacer while allowing for the delivery of a therapeutic cooling effect to the surrounding tissues, including the spinal cord. An advantage here is that the intervertebral spacer is already being installed in the patient, and the use of the therapeutic cooling aspects of the devices are at the discretion of the surgical team. In other words, the use of the devices to deliver a therapeutic cooling effect to the spinal cord does not require the surgical team to perform any additional major surgical procedures beyond what they were going to perform anyway in the context of an installation procedure of an intervertebral spacer. In effect, devices and methods described herein make feasible in trauma patients requiring spine stabilization the option of spinal cord cooling without the need for additional/separate instrumentation. In any event, fusion is not explicitly necessary in order to perform the methods described herein, though it would be unlikely to use said methods and not subsequently perform fusion. It will be appreciated that the above-mentioned benefits apply also to the alternative approaches and device embodiments described herein, including pedicular approaches.

The devices and methods described herein can provide an advantageous approach for delivering a cooling effect to tissues of the spine, and in particular to the spinal cord, for a number of reasons. Foremost, providing a cooling effect from the intervertebral space allows for the installation of the cooling apparatus into an area that is bounded longitudinally by rigid boney structures (the adjacent vertebral bodies), and with edges of the rigid boney structures being easily locatable. This intervertebral space is anatomically readily identifiable and an ideal compartment for implanted devices. The cranial and caudal boundaries of said compartment are vertebral body bone allowing for solid impaction of such devices. Furthermore, this defined space is located adjacent to the tissues of the spinal canal, including the spinal cord and nerve roots extending therefrom. These attributes allow for a cooling apparatus, as described herein, to be installed safely and reliably to a location that is adjacent to the tissues that are desired to be cooled. The fact that the space for installation of the cooling apparatus is bounded by the vertebral bodies, which are rigid or semi-rigid, allows for the apparatus, once installed, to remain fixed in its position by friction against the vertebral bodies, or by other more deliberate fixation means, preventing it from moving prior to or during the administering of a cooling effect—this can be important so that the cooling effect can be administered reliably and controllably. The fact that the intervertebral space is easily locatable, and is a space that is often accessed in surgical procedures, allows for standardized secure placement of the cooling apparatus into that space safely and reliably.

The devices described herein, when implanted in the spine, can be used in fusion procedures because of their ability to function as a supporting element in the spine. The ability for the devices described herein to bear loads including, but not limited to, the compressive loads, axial torsion, and shear forces of the spine, in addition to locally cooling the tissues of the spinal canal, including the spinal cord, allow for the accomplishment of multiple tasks with a single apparatus, saving one from having to implant (and remove) multiple different devices, thus reducing risk and complexity in the treatment of the patient. This same risk and complexity which is avoided with the devices described herein can potentially prevent one from otherwise providing a therapeutic hypothermia treatment to their patient, and thus depriving the patient the opportunity for an improved outcome. That is, in one aspect, this dual purpose of the devices described herein gives an opportunity to provide a therapeutic hypothermia treatment in situations where one might otherwise not provide such treatment with a standalone cooling apparatus due to the destructiveness and risk of accessing the intervertebral space.

A cooling effect can be applied to the spinal cord and the spinal canal from within the intervertebral space, or the space between two vertebral bodies occupied typically by the endplates and the disc. In particular, tissues can be cooled by implanting a cooling instrument into the intervertebral space. The intervertebral space is a readily locatable anatomical feature which is surgically approachable a number of different ways. Furthermore, the geometries of the intervertebral spaces are readily mapped either radiographically or through direct measurement, and are relatively consistent between patients. Accordingly, particular surrounding soft tissues are relatively consistently located in a known proximity to the intervertebral space. In particular, the intervertebral space abuts the anterior side of the spinal canal including the spinal cord. These attributes allow specific soft tissue to be reliably targeted by using adjacently located intervertebral spaces as a platform and avenue for implanting instruments near the soft tissue. Using the intervertebral space as an avenue for targeting nearby or adjacent tissues for cooling helps prevent a need to disturb the tissue which is wished to be treated. For the purposes of this description, disturb should be taken to mean incise, penetrate, displace in an adverse manner, compress, or any other physical insult that can adversely affect the tissues of the spinal column. It will be appreciated that touching of the tissue by instruments may not necessarily disturb said tissues and changing the temperature of said tissues should not be considered disturbing the tissue, as used herein.

An advantageous aspect of an intervertebral approach for providing a cooling effect to nearby soft tissue, and in particular the spinal canal including the spinal cord, is the fact that the intervertebral space is bounded by the vertebral bodies which are rigid or semi-rigid, allowing for a secure installation and fixation of a cooling instrument. A cooling instrument can be mechanically secured in the intervertebral space by spanning the intervertebral space and creating a friction-fit in the space. A cooling instrument can be secured via other means as well, such as anterior plating. It can be important that a cooling instrument is able to be secured when implanted so that it does not shift or move and so that the cooling effect it provides can be provided in a prescribed and controllable manner to a designated location. Any movement of the cooling instrument can not only change its cooling characteristics but can also impact the nearby soft tissues including the spinal cord.

An additional aspect of an intervertebral approach for implanting a cooling instrument to cool the tissues of the spinal canal is that the instrument can also be load bearing, and thus can have an integral role in stabilization of the spine (e.g., spinal fusion). In many cases where a patient has a spinal cord injury, and where the patient would benefit from an application of therapeutic hypothermia, the patient can also require stabilization of the injured spine and subsequent fusion of vertebral bodies together. In such a situation, the cooling instruments described herein can act as an intervertebral spacer restoring the natural distance between vertebral bodies, maintaining that span, and allowing for bone growth between the bodies over time. This dual functionality prevents the need to first install a cooling instrument, remove it, and then install an instrument for maintaining proper height between adjacent vertebral bodies—a multi-step procedure as this can prevent or discourage one from providing or recommending a cooling effect from a cooling instrument altogether due to the added risk and complexity of doing so in a clinical environment.

An intervertebral space approach for providing a cooling effect to soft tissues in and around the spinal canal allows for the implantation of cooling instrumentation without disturbing the soft tissue itself, and in particular, the spinal cord. That is, by cooling the tissues of the spinal canal from the intervertebral space, the targeted tissue is not physically disturbed, displaced, or incised by the cooling instrument itself or by the surgical steps needed to implant the cooling instrument. Certain tissues, such as the spinal cord tissue, are delicate and sensitive to disturbances, and such disturbances can cause injury to the tissues. As such, it can be dangerous to implant cooling instruments in these tissues or in nearby soft tissues due to risks of causing injury to the tissues. It can therefore be desirable to implant a cooling instrument into the intervertebral space which is bounded (above and below) by rigid bony structures, and cooling the nearby soft tissue, thus allowing for reliable cooling access to soft tissue without physically disturbing the soft tissue itself.

In certain embodiments, the soft tissue that is targeted to be cooled is the spinal cord, other spinal canal tissue, and/or nerve root tissue. The intervertebral space which acts as the cooling platform includes the space bounded longitudinally by the superior and inferior vertebral bodies (be they in their full natural form or having been excavated and reduced in size by surgical procedure or injury) and loosely bounded on the transverse plane by the imaginary column defined by the outer circumferences of the vertebral bodies. In other words, the intervertebral space is defined by the space that is typically occupied by the intervertebral disc (including or not including the endplates), but can extend into space once occupied by the adjacent vertebral bodies, such that the space abuts the present axial surfaces of the adjacent vertebral bodies. An intervertebral-space approach for providing cooling to the adjacent spinal canal contents targets the spinal cord without disturbing, displacing, or penetrating the spinal cord. This can be an important consideration since the spinal cord's tolerance for such intrusions is typically minimal.

The delivery of a cooling effect to the intervertebral space can result in localized cooling of areas of the spinal cord, the spinal canal, and surrounding tissue. In some cases, the cooling effect can progress to yield resultant cooling of other tissues as well. Due to inherent conductivity of bodily tissues as well as blood perfusion, which can translate the cooling effect to other parts of the body, a cooling effect can be detectable in parts of the body not local to both the cooling instruments, as described herein, and the tissues of the spinal canal, but it will be appreciated that a significantly stronger cooling effect will be felt locally. This is in contrast to methods known for cooling the entire body, also known as systemic cooling, which can yield destructive results to many of the body's organs.

Intervertebral Apparatus & Approach

Figure 10:
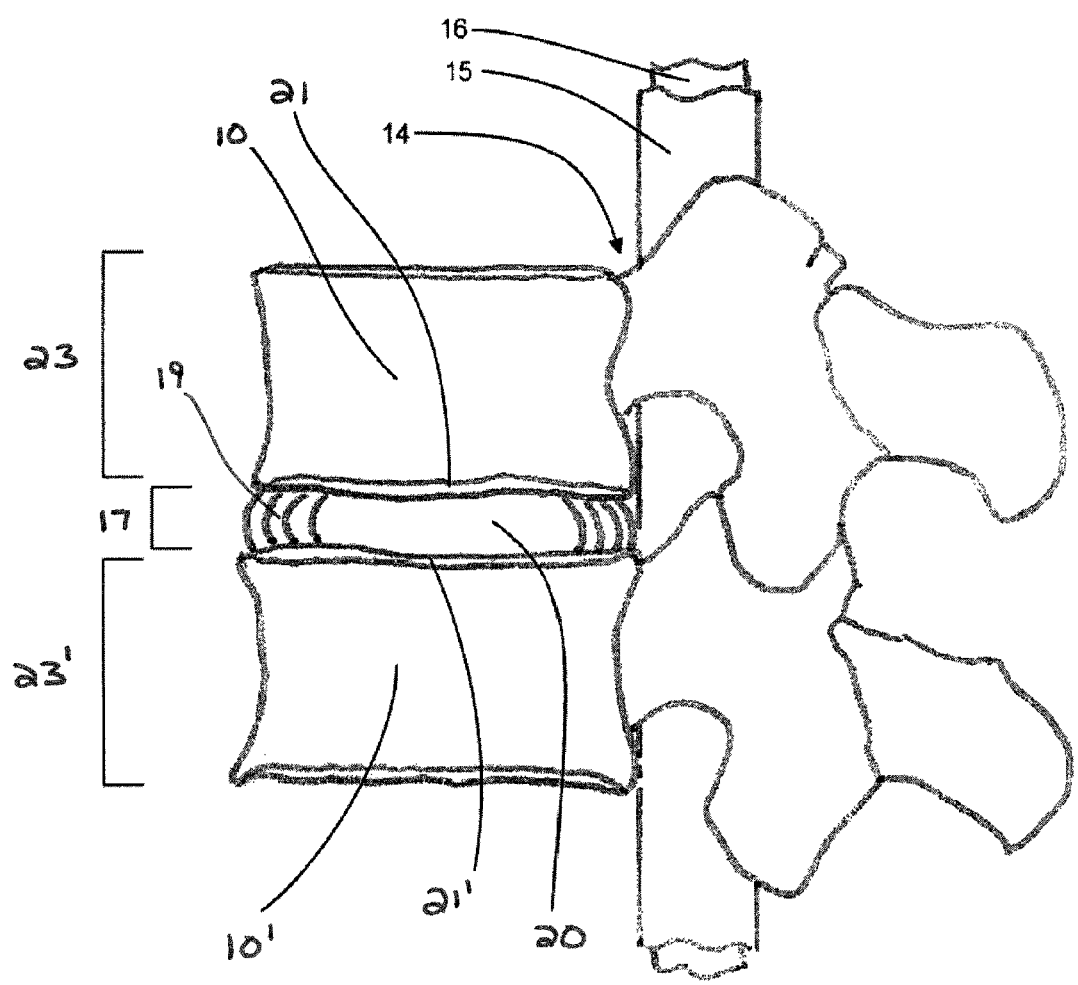
FIG. 10 is a lateral view of two vertebrae and an intervertebral disc space formed therebetween.

FIG. 10 depicts an intervertebral space 17, in the context of its surrounding vertebrae. The intervertebral space 17 is bounded longitudinally by superior and inferior vertebral bodies 10, 10' of adjacent vertebrae 23, 23'. The intervertebral space 17 is the space that is normally occupied by an intervertebral disc comprising an annulus 19 and a pulposus 20. The opposing surfaces of the vertebral bodies 10, 10' are referred to herein as axial surfaces 21, 21' (superior and inferior to the intervertebral space 17, respectively), and can include the endplates or can be the exposed bony surfaces of the vertebral bodies 10, 10'. The intervertebral space 17 is typically bounded in the transverse plane by an imaginary column created by the circumference of the vertebral bodies 10, 10' or the outer bounds of the disc annulus, but in some cases, the devices described herein can extend beyond those bounds a modest distance. The intervertebral space 17 is also bounded by the spinal canal 14 and the tissues 15 thereof, including the spinal cord 16.

As can be seen in FIG. 10, the intervertebral space 17 abuts the spinal canal 14, the tissues 15 thereof, and the spinal cord 16, making this space an advantageous platform for providing a cooling effect to these tissues without physically disturbing them. It will be appreciated that the tissues 15 and the spinal cord 16 will extend superiorly and inferiorly beyond what is shown in this figure, and that this figure represents any two adjacent vertebrae of the spine and their corresponding disc space.

Figure 11:
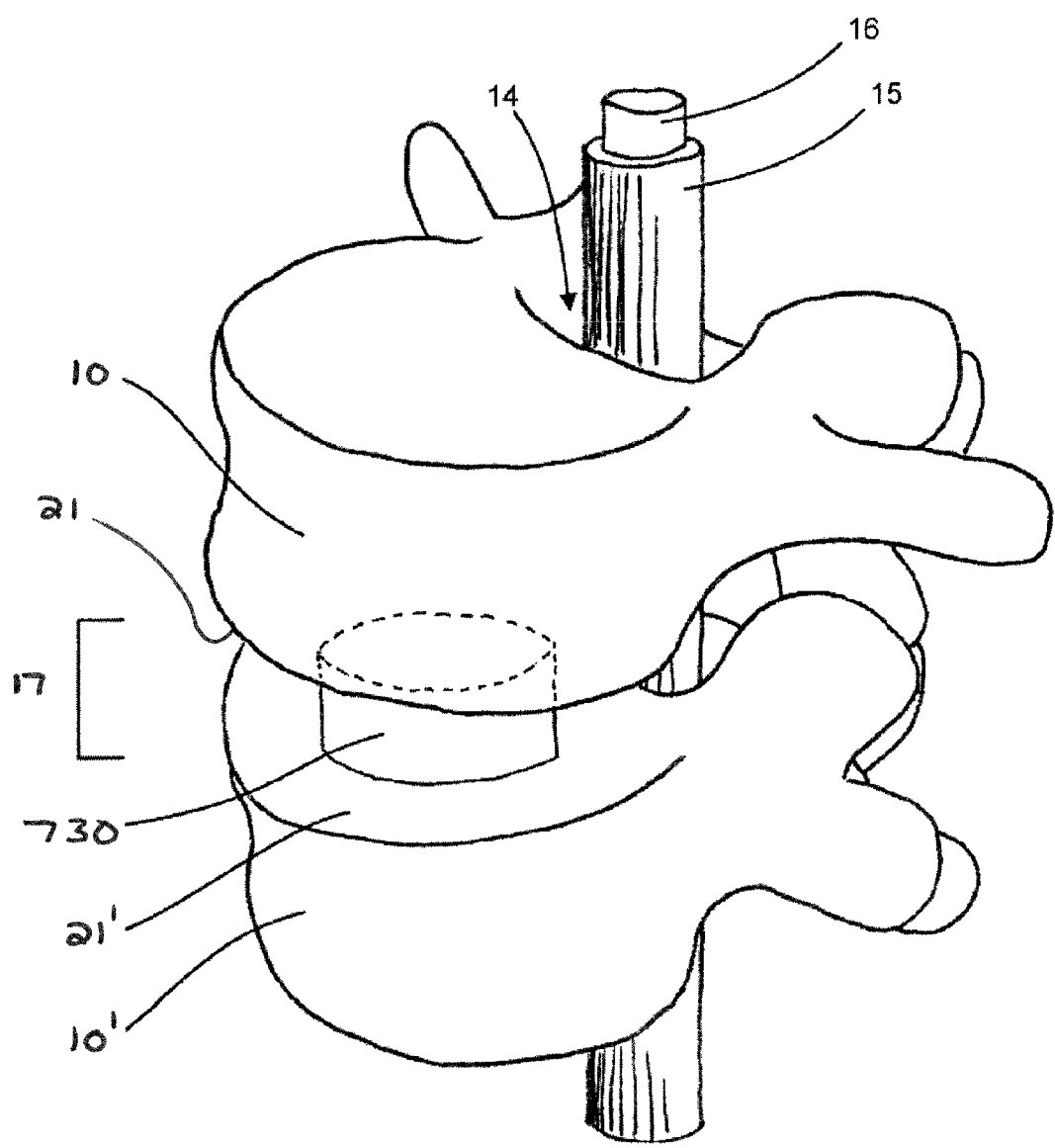
FIG. 11 is an orthogonal view of two vertebrae and an intervertebral cooling instrument installed into an intervertebral space.

FIG. 11 depicts an exemplary cooling instrument 730 of the subject matter described herein implanted in the intervertebral space 17, between the vertebral bodies 10, 10'. The cooling instrument 730 is placed between the axial surfaces 21, 21' of the vertebral bodies 10, 10' —to be clear, the axial surface 21 is the inferior surface of the vertebral body 10 and the axial surface 21' is the superior surface of the vertebral body 10', where the vertebral body 10 is superior to the intervertebral space 17 and the vertebral body 10' is inferior to the intervertebral space 17. The axial surfaces 21, 21' can be the endplates of the vertebral bodies 10, 10', or can be boney material of the vertebral bodies 10, 10' exposed either by surgical procedure or injury to the vertebral bodies 10, 10'. Endplates, which naturally exist between intervertebral disc and the vertebral bodies 10, 10' can be partially or fully removed, or augmented in some way, prior to, or during, the installation and implantation of the cooling instrument 730. It should be appreciated that when the axial surfaces 21, 21' are referred to herein, that it is intended to include any surfaces of the vertebral bodies 10, 10' that are revealed, either surgically or by injury, by the removal of any portions of the endplates or by excavating into vertebral bodies 10, 10'. As such, reference to the axial surfaces 21, 21' shall be taken to mean the endplates, the surfaces of the vertebral bodies 10, 10' abutting the intervertebral space 17, or any other related surfaces. It should be noted that the cooling instrument 730 can take on a variety of shapes as well as a variety of placements within the intervertebral space 17, and that the shape and placement as shown in this figure is only exemplary.

The intervertebral disc is not shown in this figure since, in many cases, when the cooling instrument 730 is implanted, disc material is removed. In some cases, all of the disc is removed, and in other cases, only a portion of the disc is removed. Still in other cases, though unlikely, none of disc is removed, and the cooling instrument 730 can be placed into, on top of, or below the disc, yet still in the intervertebral space 17. It should also be apparent from this figure the close proximity of the cooling instrument 730 to the spinal canal 14 and the tissues 15 of the spinal canal, including the spinal cord 16. As the cooling instrument 730 can take a variety of shapes as well as a variety of placements inside the intervertebral space 17, there may or may not be intermediary material between the cooling instrument 730 and the tissues 15 of the spinal canal 14, including spinal cord 16. Such material can be portions of the intervertebral disc, bone graft, bodily fluid, or other bodily tissue. Further, though this figure does not depict it, the cooling instrument 730 can be positioned such that it is immediately abutting the tissue 15 of the spinal canal 14.

Figure 12A:
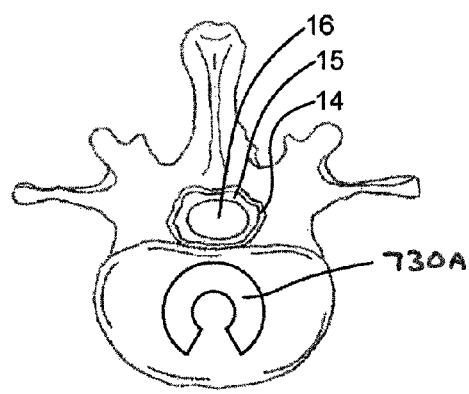
FIG. 12A is a top view of a vertebra and one embodiment of an intervertebral cooling instrument positioned within a disc space adjacent to the vertebra.
Figure 12B:
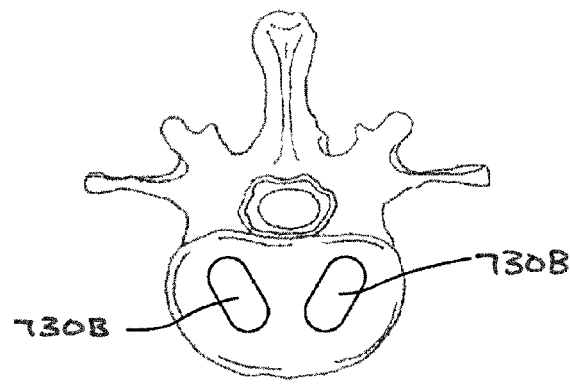
FIG. 12B is a top view of a vertebra and another embodiment of an intervertebral cooling instrument positioned within a disc space adjacent to the vertebra.
Figure 12C:
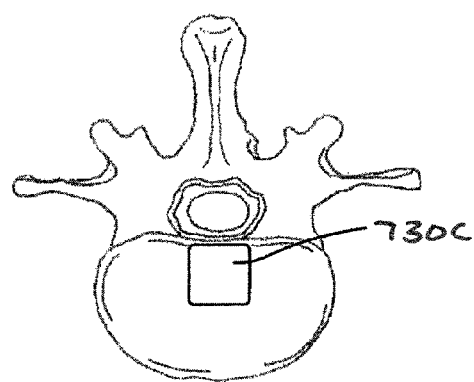
FIG. 12C is a top view of a vertebra and another embodiment of an intervertebral cooling instrument positioned within a disc space adjacent to the vertebra.
Figure 12D:
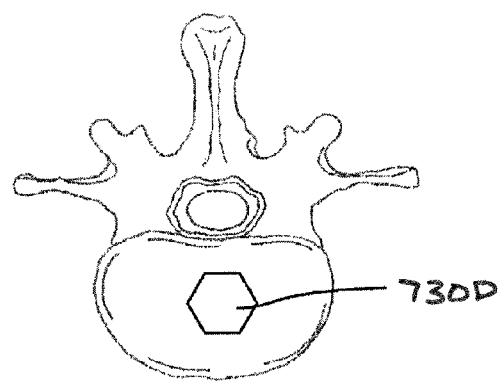
FIG. 12D is a top view of a vertebra and another embodiment of an intervertebral cooling instrument positioned within a disc space adjacent to the vertebra.
Figure 12E:
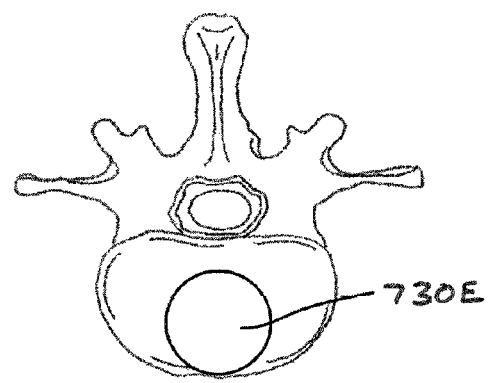
FIG. 12E is a top view of a vertebra and another embodiment of an intervertebral cooling instrument positioned within a disc space adjacent to the vertebra.
Figure 12F:
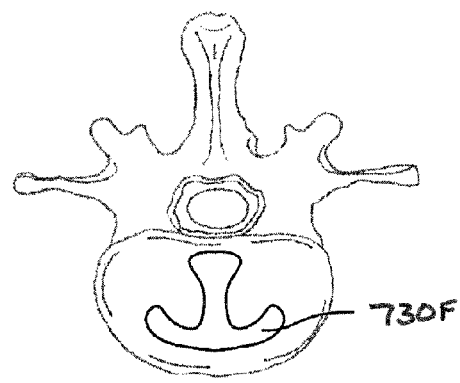
FIG. 12F is a top view of a vertebra and another embodiment of an intervertebral cooling instrument positioned within a disc space adjacent to the vertebra.

The cooling instrument, as shown in FIGS. 12A-12F, can take a variety of shapes and sizes and can be positioned anywhere within the intervertebral space. This includes placing it in the very middle of the space, on the posterior side, on the anterior side, or on one or both of the lateral sides. The shape of the cooling instrument can be simple or complex. FIG. 12A illustrates an embodiment of a cooling instrument 730A having a cross-section in the shape of a partial annulus. FIG. 12B illustrates an embodiment of a cooling instrument 730B having an elliptical cross-section. FIG. 12C illustrates an embodiment of a cooling instrument 730C having a rectangular cross-section. FIG. 12D illustrates an embodiment of a cooling instrument 730D having a hexagonal cross-section. FIG. 12E illustrates an embodiment of a cooling instrument 730E having a circular cross-section. FIG. 12F illustrates an embodiment of a cooling instrument 730F having a substantially T-shaped cross-section.

As shown in FIG. 12B, multiple cooling instruments 730B can be placed in a single intervertebral space, such as placing two instruments, one on each lateral side. It will be appreciated that although cooling instruments can be placed anywhere, it can be advantageous to place one or multiple on the posterior side of the intervertebral space so as to more directly provide a cooling effect to the tissues 15 of the spinal canal 14, and in particular, to the spinal cord 16. In addition, it will be appreciated that it can be desirable to place one or multiple cooling instruments such that it will act as a balanced, stable, and rigidly placed spacer able to support the variable weight and forces of the superior portion of the patient. That is, it can be advantageous to place the cooling instrument in one position versus another based on various factors, such as a particular placement's ability to directly hold and support the patient's upper body, an ability of the cooling instrument to be better seated in a particular placement, etc. Additionally, the placement of the cooling instrument can also be determined by requirements and needs for bone growth in the intervertebral space in a subsequent fusion process.

Approaching and accessing the intervertebral space for the implanting, adjusting, operating, and partial or full removal of the devices described herein can proceed in a number of different ways. These ways include the approaches and the access techniques that are commonly used when surgically addressing spondylolisthesis, removing loose spinal bone fragments, treating and removing herniated discs, decompressing the disc space, and implanting typical intervertebral spacers. These approaches include, but are not limited to, anterior lumbar (as used in an ALIF procedure), lateral lumbar, posterior lumbar (as used in a PLIF procedure), lateral thoracic, and anterior cervical approaches. These approaches can occur singularly, or multiple approaches can occur simultaneously, near simultaneously, or serially, such as in a bilateral posterior lumbar approach procedure. It will be appreciated that lateral, anterior, and posterior approaches can be used in all levels of the spine, though some approaches are more advantageous than others at different levels due to the tissues and/or organs at a level that can make a certain approach difficult (e.g., the presence and location of the heart makes an anterior approach difficult in the thoracic level).

The following exemplary approach can be used to implant the devices as described herein:

First, the level or levels of the spine can be located by palpation, marking, and/or fluoroscopy. The vertebral bodies can then be exposed using dissection and retraction techniques. The disc can then be completely or partially removed, for example by cutting a window in the annulus using scalpel and removing some or all of the nuclear pulposis using a pituitary rongeur or ring curettes. The implant bed can then be prepared by removing all or some of the cartilaginous endplates using rasps, paddle shavers, and/or curettes. The apparatus can then be placed. Such placement can include distraction of the intervertebral space (optional based on whether the apparatus is intended to be impacted into position or whether using a self distracting inserter). The apparatus size can be selected by implanting trial spacers. Once a size is selected, fenestrations of the apparatus can be packed with graft (optional depending on whether apparatus is also being used for fusion) and the apparatus can be placed within the intervertebral space. Proper apparatus positioning can be confirmed with AP & Lateral radiographs. The conduits of the apparatus can be tunneled so as to exit the skin through the skin incision and then the surgical wound can be closed.

It will be appreciated that any number of procedures, in addition to the above, and in addition to those that are common in medical practice, can be used for installing and implanting the apparatus as described herein.

Intervertebral Coolant Means and Source

The cooling instrument 730 can provide a cooling effect by a number of different coolant means. For example, the coolant means can be the expansion of gas or circulation of a chilled fluid through the cooling instrument 730. In one embodiment, the cooling instrument 730 can receive a compressed gas which by expansion acts as a coolant in cooling instrument 730. The expansion of the gas causes the gas and cooling instrument 730 around it to experience a rapid decrease in temperature. Typical gases for such an application include Nitrous Oxide and Carbon Dioxide, but it will be appreciated that there are a wide variety of gases which can be used in this application. It will be appreciated that in compressed form, some of these gases will be liquid.

In other embodiments, the cooling instrument 730 can receive a chilled coolant or a chilled fluid as the coolant means which flows through cavities or channels of the cooling instrument, effectively decreasing the temperature of the cooling instrument. Typical coolants include saline solutions, liquid nitrogen, and ethyl alcohol. It will be appreciated that any number of fluids can be used in this application, but there are advantages to using biologically safe fluids.

In still other embodiments, the cooling instrument 730 can contain a thermoelectric device, such as a Peltier device, which when a voltage or current is applied, at least a portion of the device experiences a reduction in temperature. In still other aspects, the cooling instrument 730 can house an endothermic chemical reaction which results in the reduction of temperature of the contents of the cooling instrument 730 and the cooling instrument 730 itself. It will be appreciated by those skilled in the art that there are a variety of means by which the cooling instrument 730 can be cooled.

Figure 13:
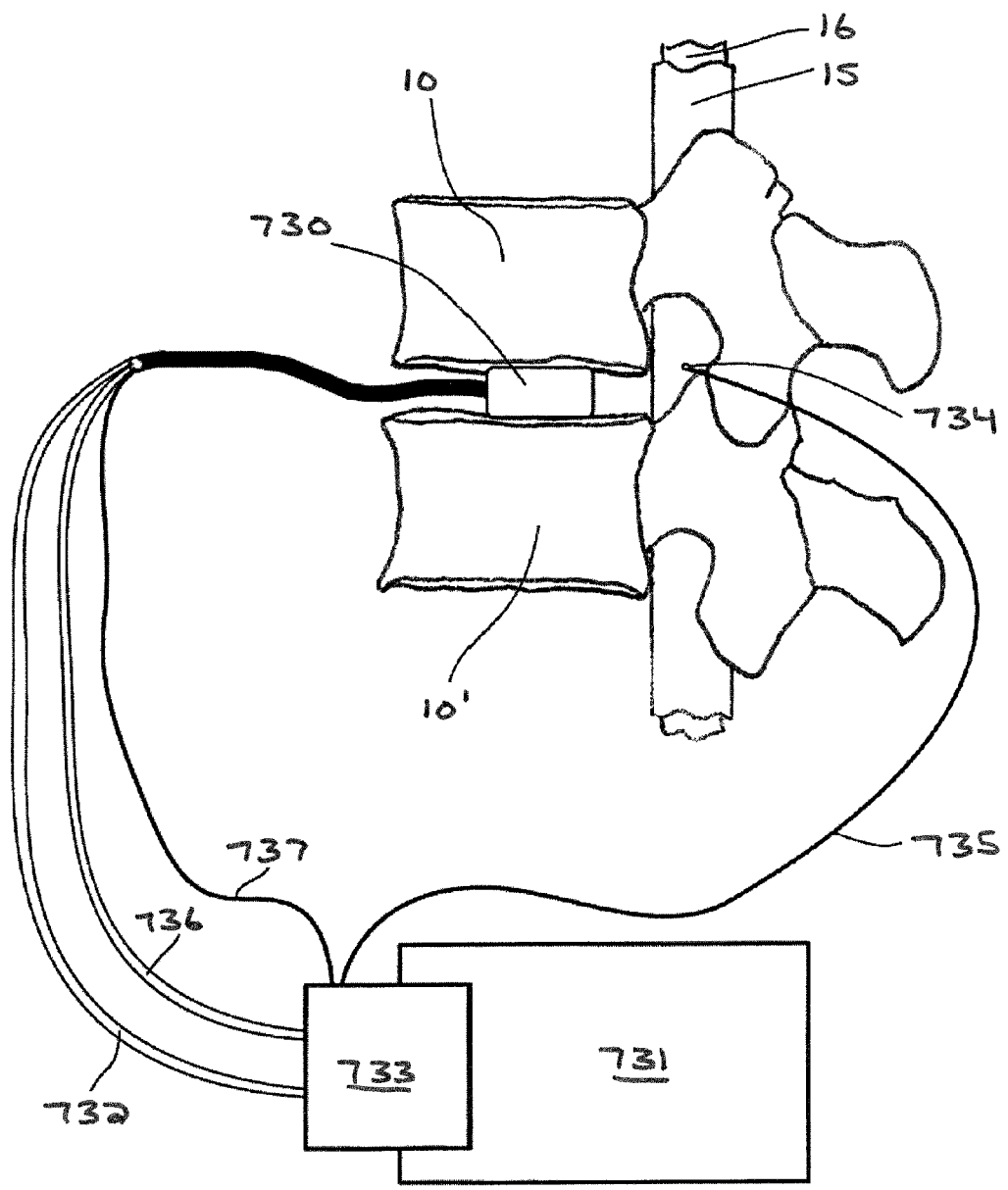
FIG. 13 is a schematic diagram of an intervertebral cooling instrument implanted into a disc space between two vertebrae and an associated coolant source and controller.

FIG. 13 depicts an exemplary arrangement of a cooling instrument 730 installed in an intervertebral space 17 and connected to additional devices aiding in delivery of a cooling effect from the cooling instrument 730. The coolant means can be provided from an external (e.g., extracorporeal) coolant source 731. In implementations in which the coolant means is an expanding gas, the coolant source 731 can be a tank of compressed gas which is released into the cooling instrument 730 through a coolant delivery conduit 732. Once the compressed gas is in the cooling instrument 730, it can be expanded through an expansion nozzle into an expansion chamber (not shown) formed within the cooling instrument 730, causing a rapid decrease in temperature. Alternatively, or in addition, the coolant source can include a compressor that compresses gas. In some implementations, this delivery of the coolant means from the tank of compressed gas is regulated with a control unit 733 to limit the amount of gas and the pressure of the gas entering the cooling instrument 730 via the coolant delivery conduit 732. The control unit 733 can be an adjustable valve on the tank, which can be manually controlled, mechanically controlled, or automatically controlled by a computing device. In implementations in which the coolant source 731 is a compressor, the control unit 733 can control the degree to which the compressor compresses the gas or the pressure at which the gas is presented down the conduit 732. The regulation of the release of the gas can be managed manually or automatically, in either case, based on established protocols, conditions of the patient, and/or detectable physiological characteristics of the patient. There can be an additional conduit, exhaust conduit 736, leaving the cooling instrument 730 from the expansion chamber to exhaust the expanded gas. This conduit can either exhaust the gas into the atmosphere, to a collection tank, and/or to a compressor, which in turn re-compresses the gas for reuse.

The control unit 733 can take a variety of forms and can control various aspects of the delivery of a coolant means from the coolant source 731 to the cooling instrument 730, such as an amount of coolant means that is delivered or a temperature, pressure, flow, voltage (in the case of a thermoelectric device), or other attribute of the coolant means that will affect the cooling effect realized. In its simplest form, the control unit 733 simply provides a mechanism for turning the delivery of coolant means on or off. Examples of such functionality for allowing the flow of a fluid coolant means to the cooling instrument 730 from the coolant source 731 include, but are not limited to, a stop-cock, a valve, a tube clamp (or other tools for pinching tubing to block its flow), other removable physical impeding structures, and back pressure. In more complex forms, the control unit 733 can be a PID controller in connection with a fluid pump which takes input data, such as temperatures measured by one or more temperature sensors 734 and/or other sensors, delivered by one or more sensor wires 735, and determines and pumps a volumetric flow rate of a fluid coolant means. Besides controlling the flow of coolant means, the control unit 733 can also control the temperature and pressure of coolant means in the cases where the coolant means is a fluid.

In implementations in which the coolant means is a chilled fluid, the coolant source 731 can include a chiller and/or a basin of chilled fluid with a pump or other apparatus for cooling and pumping fluid, and the coolant delivery conduit 732 can be a tube for delivering the chilled fluid to the cooling instrument 730. In this case, there can be an exhaust conduit 736 to return or exhaust the chilled fluid from the cooling instrument 730 back to the coolant source 731 or to a collection tank or to a waste drain.

The delivery and exhaust conduits 732, 736 can be typical tubing made of plastic, silicones, or metal, or can be any means for communicating fluid. The conduits 732, 736 can be flexible or rigid in nature.

In implementations in which the coolant means is a Peltier device embedded in the cooling instrument 730, the coolant source 731 can include a power supply that powers the Peltier device, the control unit 733 can control the amount of power delivered from the power supply, and the coolant delivery conduit 732 can be one or more electrical lines that deliver current from the power supply to the Peltier device. In such an implementation, conduits can be provided to and from the cooling instrument 730 to remove exhaust/separated heat from the Peltier device to outside the body.

It will be appreciated that the cooling instrument 730 can create a cooling effect in a variety of ways, including other ways not mentioned here. Further, it will be appreciated that not all cooling means will necessarily utilize or have both delivery and exhaust conduits as shown in FIG. 13. Further, it will be appreciated that more conduits than a single coolant delivery conduit 732 and a single exhaust conduit 736 can be utilized in the cooling instrument's delivery of a cooling effect to surrounding tissue.

The cooling source 731, control unit 733, and conduits 732, 736, either individually or together, can supply more than one cooling instrument 730.

The coolant source 731 and the control unit 733 can be aspects of a single component or can be co-located in a single housing. The coolant source 731 and the control unit 733 can also exist as separate and distinguishable components.

The coolant source 731 and the control unit 733 can advantageously reside outside of the patient's body, in which case the coolant delivery conduit 732, the exhaust conduit 736, and any other conduits, and any wires or other means for communicating substance or signals between the coolant source 731 and/or the control unit 733 to and from the cooling instrument 730, can be routed through a tissue opening in the patient's skin. Alternatively, there can be cases where either or both the coolant source 731 and the control unit 733 are installed inside the patient's body. Further, the control unit 733, if small enough, can reside inside the cooling instrument 730.

The coolant means can be regulated by the control unit 733 to deliver a predetermined cooling effect, such as a specific temperature at a specific location. The coolant means can also be regulated such that a specific volume of coolant of the coolant means is delivered, in the cases where the coolant is a chilled liquid or expandable gas. The coolant means can also be regulated based on changes or lack of changes in physiological characteristics. For example, the regulation of the coolant means, and thus the intensity of cooling, can be determined by quantitative and qualitative sensory or motor-evoked potential (SEP, MEP) observations. In this example, the coolant means is provided at a certain level until the patient's SEP/MEP results begin to degrade, improve, or change, at which point the regulation of the coolant means can increase or decrease the cooling effect, for example by adjusting the rate of delivery or temperature of the coolant means. It will be appreciated that any number of physiological characteristics can be used to regulate the intensity of coolant means, including but not limited to: blood pressure, target-tissue temperature, specific tissue temperature (proximate to target tissue), rectal body temperature, venous blood temperature near or exiting target tissue, neurologic findings, pulmonary conditions, cardiac conditions, intrathecal pressure, perfusion pressure, levels of blood oxygen & glucose, ATP concentrations, and markers of excitotoxicity, vasogenic edema, apoptosis, inflammation, and enzymatic responses. A qualitative or quantitative determination can be made based on any of the listed physiological characteristics as to how the coolant means should be regulated.

A sensor 734 can be implanted in or around the patient. The sensor 734 can be a temperature sensor to sense the temperature of particular tissues, anatomy, or instruments, where this sensed temperature can be used to control the delivery of the coolant means to the cooling instrument 730. The sensor 734 can be connected via sensor wires 735 to the control unit 733, thereby providing a feedback loop of information to help determine how much coolant means to deliver or at what temperature to deliver the coolant means to the cooling instrument 730. The sensor 734 can also be connected via the sensor wires 735 to a display, meter, dial, or other indicator providing some form of output data from the sensor 734 that can allow one to manually regulate or control the delivery of the coolant means. The sensor 734 can also be connectable wirelessly and a wireless link can be used instead of the sensor wires 735, or optically, in which case the sensor wires 735 can be fiber optics.

In one implementation, the sensor 734 is a temperature measuring sensor, such as a thermistor or thermocouple, embedded into tissue near the spinal cord, providing temperature data of the tissue, which is used to either manually or automatically regulate the delivery of the coolant means. The sensor 734 can also be a temperature sensor embedded in the intrathecal space of the spinal canal contents 15 to measure temperature of cerebral spinal fluid. The sensor 734 can also be a pressure sensor measuring the pressure of the cerebral spinal fluid. It will be appreciated that more than one sensor 734, more than one sensor type, and more than one sensor placement location can be used simultaneously and that the data gathered from the multiple sensors 734, connected via one or more multiple sensor wires 735, can be used independently or in combination to determine how the delivery of the coolant means is regulated or controlled. Other types of relevant sensors that can be used include, without limitation, pressure sensors, chemical sensors, electrical sensors, magnetic sensors, and optical sensors. Other types of sensing, such as remote sensing, can be used that do not require the sensor itself to be placed within the patient—ultrasound, including Doppler measurements, and functional MRI, all can be used to sense physiological characteristics that may be used to control or regulate the delivery of the coolant means. In one aspect, the information measured by a sensor or sensors can be used to continually adjust the regulation of the delivery of the coolant means in real time or almost real time. Alternatively, or in addition, the sensed information can be used for safety monitoring. The advantages of using a sensor or sensors, along with sensor wires or other communication means, will be appreciated though their use may not be necessary.

The cooling instrument 730 can have a sensor or sensors of a variety of types embedded in or on it. In one implementation, the sensor or sensors can measure internal or surface temperatures of the cooling instrument 730. The sensor or sensors can also measure other attributes of the cooling instrument 730, such as internal pressures or strain on the cooling instrument 730. The sensor or sensors can connect via sensor wires 737 to the control unit 733, thereby providing a feedback loop of information to help determine how much coolant means to deliver to the cooling instrument 730. The sensor or sensors can also be connected via sensor wires 737 to a display, meter, dial, or other indicator providing some form of output data from the sensor or sensors that can allow one to manually regulate the delivery of the coolant means. The sensor or sensors can also be connectable wirelessly and a wireless link can be used instead of the sensor wires 737, or optically, in which case the sensor wires 737 can be fiber optics. Other types of relevant sensors that can be used include, without limitation, pressure sensors, chemical sensors, electrical sensors, magnetic sensors, and optical sensors. In one aspect, the information measured by a sensor or sensors can be used to continually adjust the regulation of the delivery of the coolant means in real time or almost real time. Alternatively, or in addition, the sensed information can be used for safety monitoring. The advantages of using a sensor or sensors, along with sensor wires or other communication means, will be appreciated though their use may not be necessary.

Figure 14A:
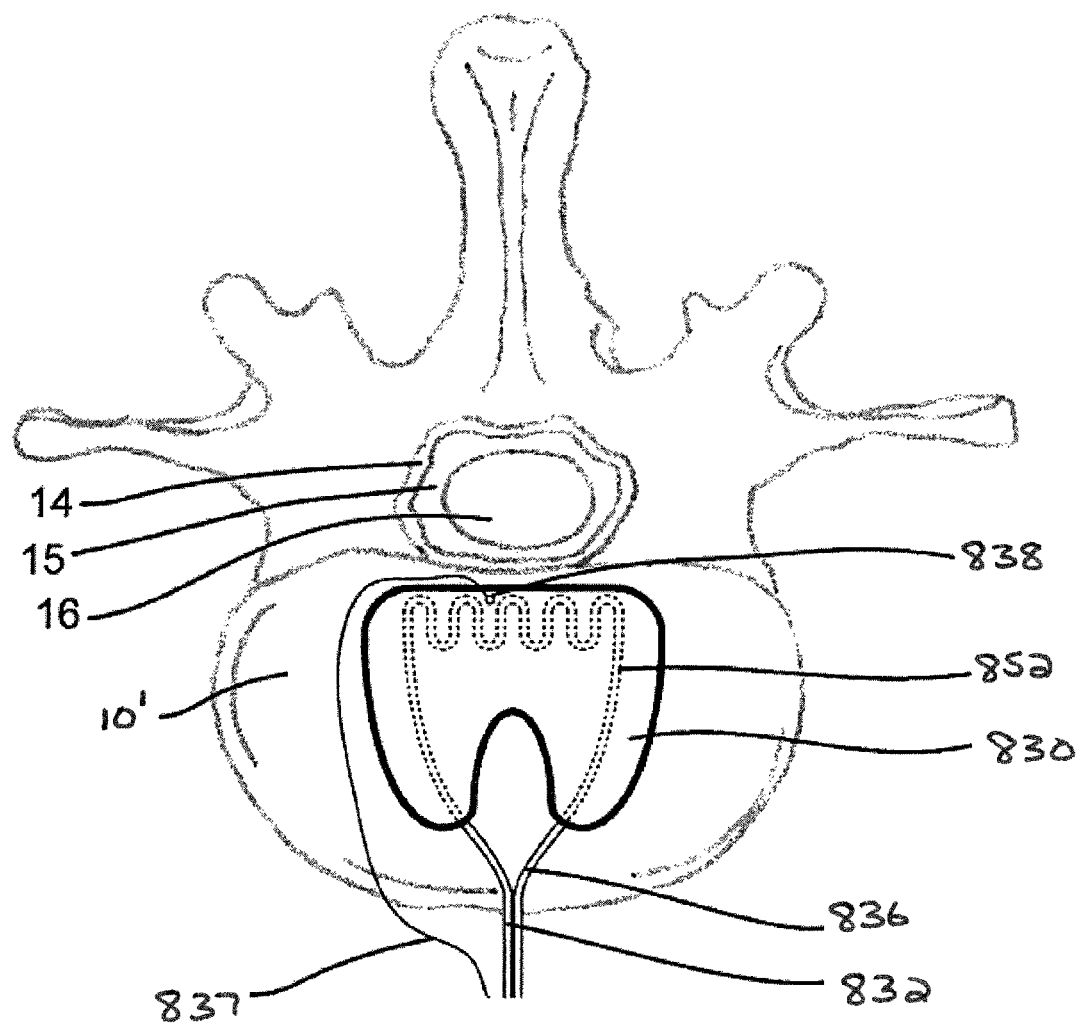
FIG. 14A is a top view of a vertebra and one embodiment of an intervertebral cooling instrument positioned within a disc space adjacent to the vertebra.

FIG. 14A depicts an exemplary cooling instrument 830 configured to be cooled using a chilled fluid as the coolant means. As shown, the cooling instrument 830 can have an inner chamber 852 in the form of a coolant channel which connects between the coolant delivery conduit 832 and the exhaust conduit 836, channeling the chilled fluid through the cooling instrument 830 and thus cooling at least one thermally conductive wall of the cooling instrument 830. This channel can be coiled, spiraled, snaked, or have any other complex shape to it to increase the inner surface area of the channel, and thus increase the heat transfer between the cooling instrument 830 and the circulating coolant fluid. The pathway of the coolant channel 852 can advantageously be located within the cooling instrument 830 such that it more effectively delivers a cooling effect to the tissues 15 of the spinal canal 14, including the spinal cord 16. For example, the pathway of the coolant channel 852 can extend through the posterior portion of the cooling instrument 830.

As shown in FIG. 14A, the channel 852 can be a winding pathway connecting the coolant delivery conduit 832 to the exhaust conduit 836. Alternatively, the channel 852 may not have a winding pathway, but can instead form a straighter or more direct pathway, such as a larger 'U' shape. Furthermore, the shape or path of the channel 852 can depend on where the coolant delivery conduit 832 and the exhaust conduit 836 enter and exit the body of the cooling instrument 830. If the two conduits are laterally opposed, then the channel 852 can form a straight pathway between them. Further, the coolant channel 852 can consist of multiple channels or multiple pathways that diverge and then later converge into one.

Figure 14B:
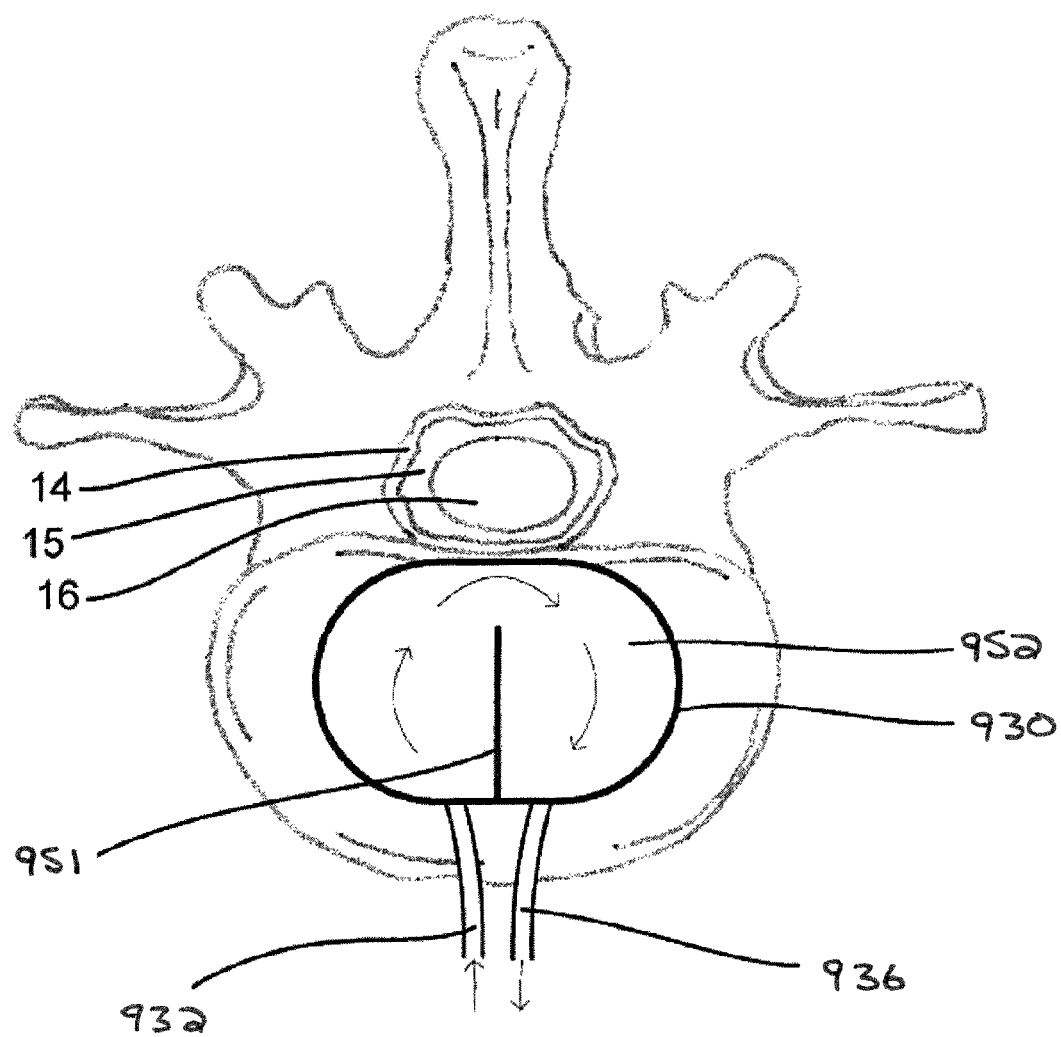
FIG. 14B is a top view of a vertebra and another embodiment of an intervertebral cooling instrument positioned within a disc space adjacent to the vertebra.

FIG. 14B illustrates an alternative embodiment of a cooling instrument 930 in which a single large coolant chamber 952 is provided through which a coolant fluid can be circulated. The coolant chamber 952 connects the coolant delivery conduit 932 to the exhaust conduit 936, optionally utilizing some distance of more defined coolant channels to connect the conduits 932, 936 to the chamber 952. For example, discrete coolant channels can be provided having a diameter that is substantially the same as the diameter of the conduits 932, 936. These channels can extend postiorly from said conduits, eventually opening into a larger chamber 952 formed in a posterior portion of the cooling instrument 930.

The inner surface of the coolant chamber 952 can have various surface area increasing features to improve the conduction of heat between the cooling chamber 952 and the cooling instrument 930, which in turn cools the relevant tissues. For example, the inner surface can be scalloped, can have thermal fins, or can have a network of conductive elements that act as a sieve for the coolant to flow through. Alternatively, the inner surface of coolant chamber 952 can be smooth.

The coolant chamber 952 can have a dividing wall 951 formed therein to separate the entry of the coolant from the coolant delivery conduit 932 and the exhaust of the coolant into the exhaust conduit 936, making the coolant fluid travel further between the two.

It will be appreciated by those skilled in the art that the coolant channels, chambers, etc. formed within the cooling instrument can have a variety of shapes, sizes, orientations, and positions and are not limited to those described here. Such features can provide a means for the cooling instrument to deliver a cooling effect to the tissues of the spinal canal, including the spinal cord and nerve roots extending therefrom. Further, the coolant delivery conduit 932 and the exhaust conduit 936 can interface with such channels and chambers in a variety of ways, from a variety of directions, and are not limited to those described here.

In some cases, conduits connecting to the cooling instrument, channels or chambers disposed within or in proximity to the cooling instrument, as well as any sensors or sensor wires embedded in or attached to or near the cooling instrument, can be detachable. This can be advantageous when the cooling instrument will remain in the patient beyond surgery to act as a load bearing structural support and to facilitate fusion. In such cases, prior to detaching any components, the chilled fluid can be evacuated from the conduits, channels, and/or chambers, etc. such that no fluid remains in the patient. This evacuation can be accomplished by applying a vacuum to the conduits, channels, and/or chambers, or alternatively by applying a positive pressure.

Figure 15A:
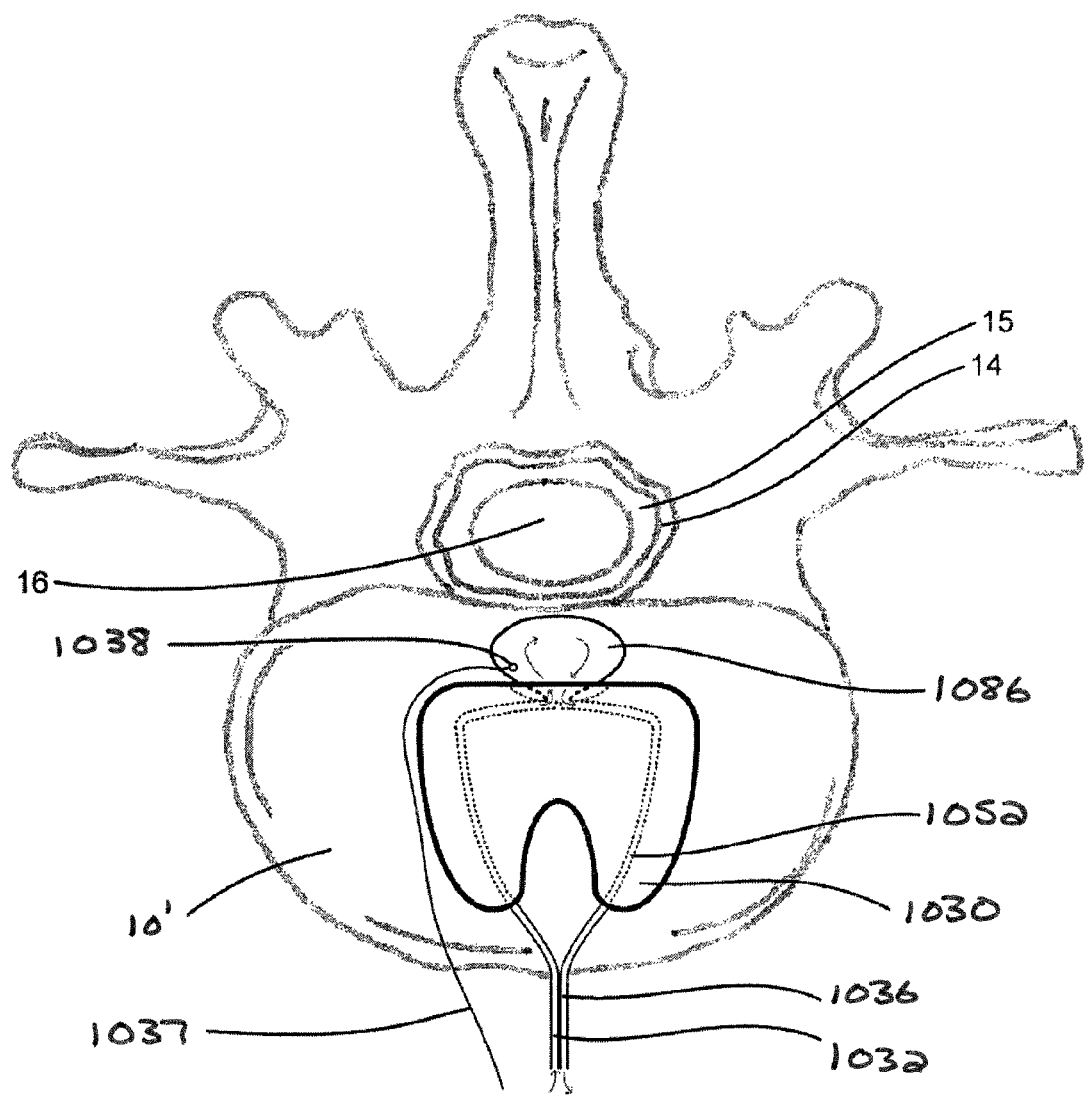
FIG. 15A is a top view of a vertebra and another embodiment of an intervertebral cooling instrument positioned within a disc space adjacent to the vertebra.

FIG. 15A illustrates an embodiment of a cooling instrument 1030 that includes an expandable element 1086 (e.g., a balloon). As shown, the expandable balloon 1086 can be positioned within the cooling instrument 1030 and can be connected to a coolant delivery conduit 1032 and an exhaust conduit 1036, optionally through a chamber 1052 (e.g., a coolant channel having a substantially circular cross section). When chilled fluid is circulated into the cooling instrument 1030, the expandable balloon 1086 can become inflated with the cooling fluid and the cooling fluid can circulate within the balloon. In one embodiment, the balloon 1086 is positioned on a side of the cooling instrument 1030 that is most proximate to the spinal canal 14. The balloon 1086, when expanded, can extend through an aperture formed, e.g., in a posterior surface of the cooling instrument 1030 and into close proximity to or in direct contact with the spinal canal 14, thereby positioning the source of the cooling effect more closely to spinal canal 14. The balloon 1086 can also have a thinner and more thermally conductive wall than the other portions of the cooling instrument 1030, thus improving the efficiency of the delivery of the cooling effect. In an alternative embodiment, the chamber 1052 can be omitted and the conduits 1032, 1036 can be directly coupled to the balloon 1086. The balloon 1086 can be formed from any of a variety of different materials, including PET, silicone, latex, and combinations thereof. When the balloon 1086 is not inflated, it can be partially or entirely contained within the cooling instrument 1030, and it can form a shape similar in size/diameter to the rest of the chamber 1052 and/or the conduits 1032, 1036. When expanded, the balloon 1086 can grow to a size many times its non-inflated size.

Figure 15B:
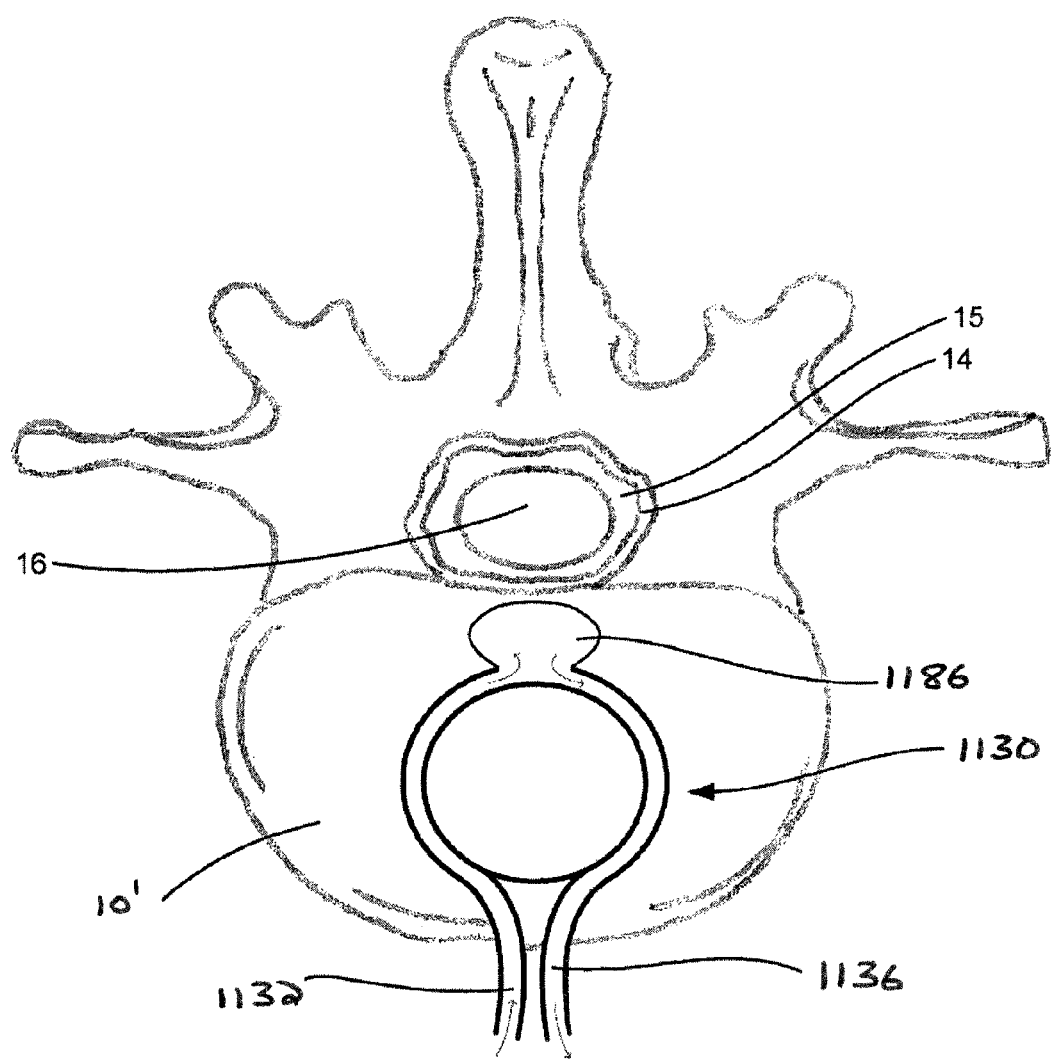
FIG. 15B is a top view of a vertebra and another embodiment of an intervertebral cooling instrument positioned within a disc space adjacent to the vertebra.

FIG. 15B illustrates an embodiment of a cooling instrument 1130 that includes an expandable element 1186 (e.g., a balloon) that is directly coupled to the delivery and exhaust conduits 1032, 1036, which are wrapped along an exterior perimeter surface of the cooling instrument 1130, rather than extending through an interior of the cooling instrument 1130. The balloon portion 1186 can be positioned on a side of cooling instrument 1130 most proximate to the spinal canal 14 (e.g., on a posterior side of the cooling instrument 1130) to provide the most efficient cooling to that area. When it is desired to detach the balloon 1186 and the conduits 1132 and 1136 from the rest of cooling instrument 1130, the conduits 1132 and 1136 with the balloon 1186 connecting them can be pulled from one side, causing the other side to follow it around the body of the cooling instrument 1130 and out the other side. In other words, after deflating the balloon 1186 and evacuating the conduits 1132, 1136 of cooling fluid, one of the conduits can be released while tension is applied to the other to pull the assembly of the balloon 1186 and conduits 1132, 1136 out of the patient.

Figure 15C:
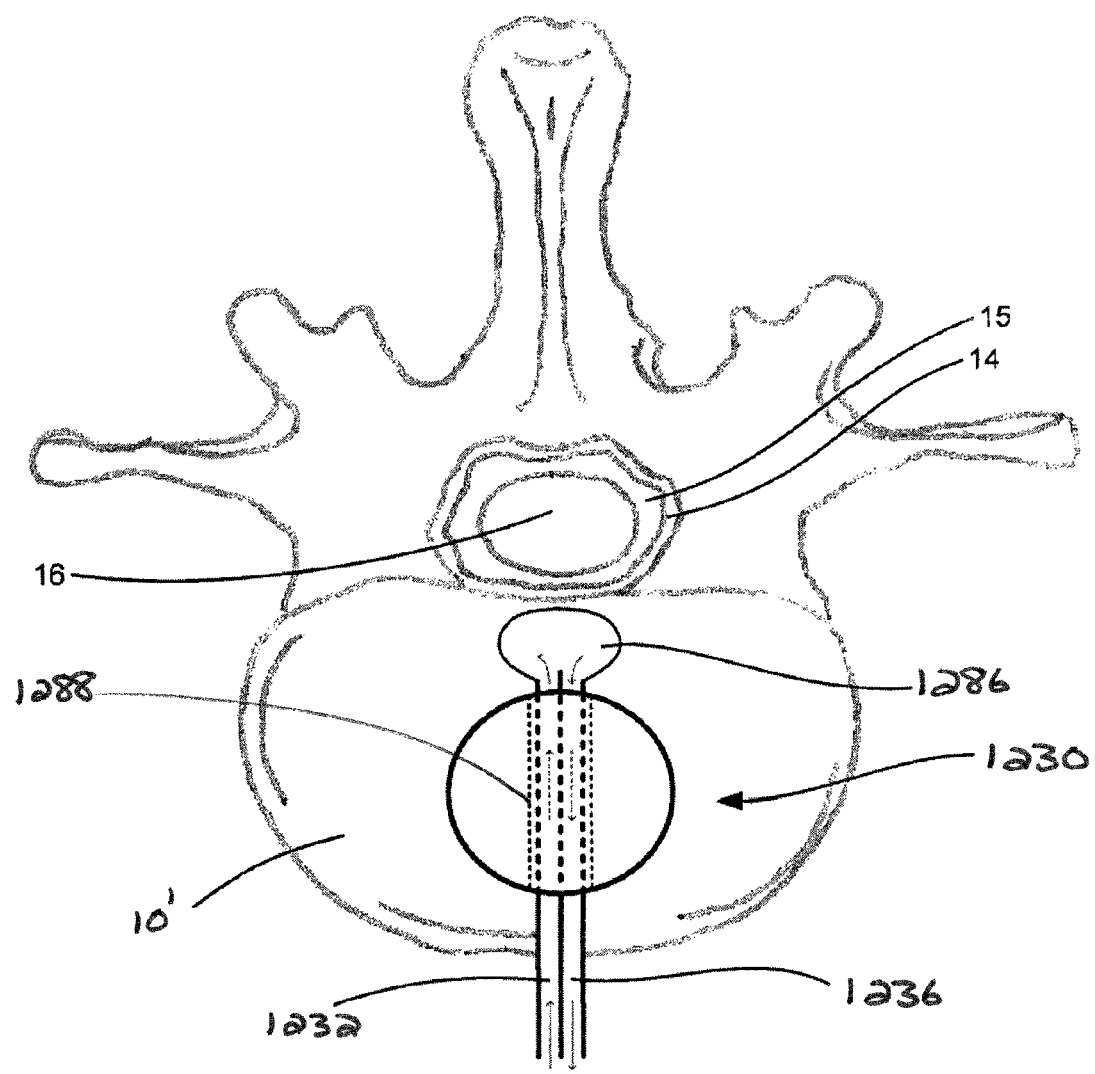
FIG. 15C is a top view of a vertebra and another embodiment of an intervertebral cooling instrument positioned within a disc space adjacent to the vertebra.

FIG. 15C illustrates an embodiment of a cooling instrument 1230 that includes an expandable element 1286 (e.g., a balloon) that is directly connected to the delivery and exhaust conduits 1232, 1236 and in which the expandable element 1286 and the conduits 1232, 1236 are removable from the cooling instrument 1230. As shown, the conduits 1232, 1236 are routed through a tunnel 1288 formed in the cooling instrument 1230. The tunnel 1288 and the conduits extending therethrough run all the way through the cooling instrument 1230 such that the balloon 1286 can be positioned external to the cooling instrument 1230 on a posterior surface thereof. In use, the balloon 1286 can be inflated by supplying a cooling fluid thereto under pressure. When inflated, the balloon 1286 has a dimension larger than a corresponding dimension of the tunnel 1288, thereby preventing the balloon 1286 from passing anteriorly through the tunnel 1288. When the cooling procedure is completed, or at any other desired time, the balloon 1286 can be partially or completely deflated, for example by evacuating cooling fluid therefrom or by reducing the pressure at which cooling fluid is supplied thereto. When deflated, the balloon 1286 has a dimension smaller than a corresponding dimension of the tunnel 1288 such that application of pulling force to the conduits 1232, 1236 in the anterior direction can cause the conduits 1232, 1236 and the balloon 1286 coupled thereto to be completely withdrawn through the tunnel 1288 and separated from the cooling instrument 1230.

Figure 16:
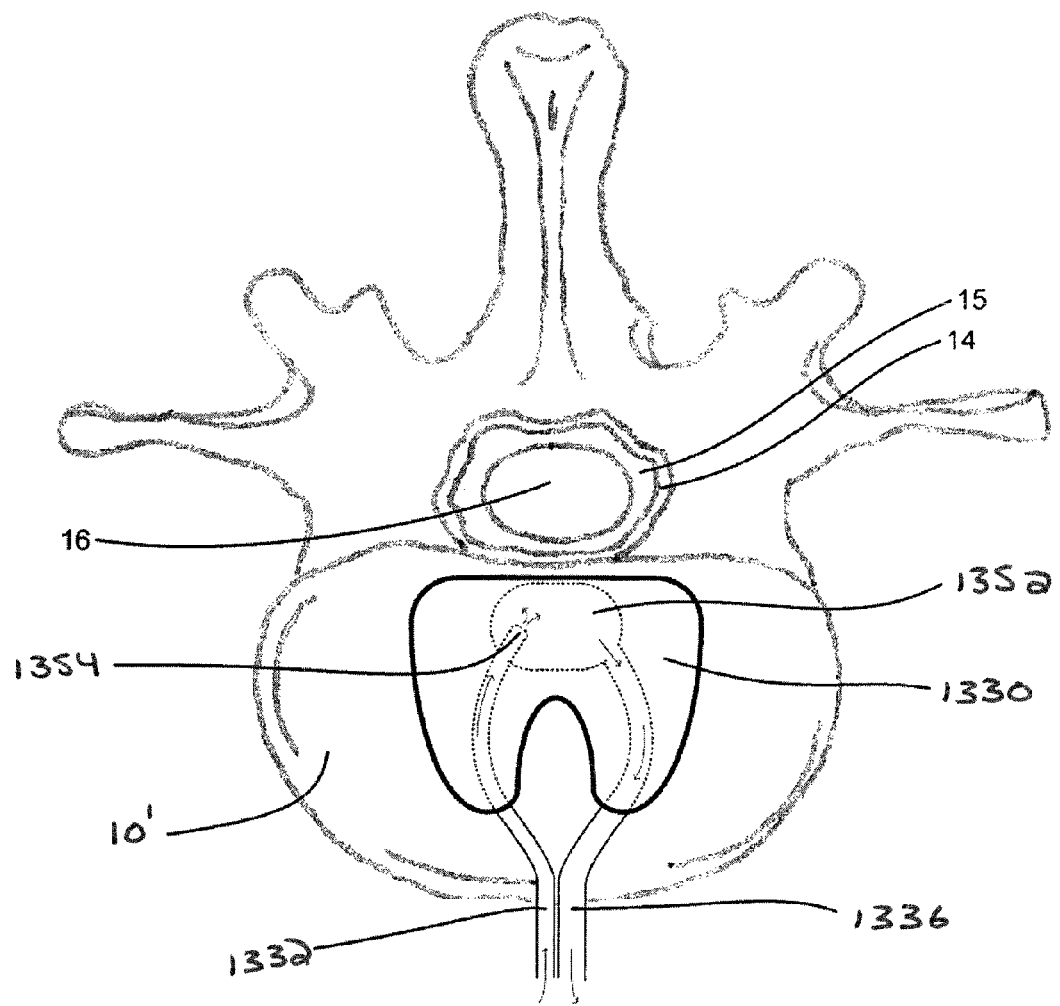
FIG. 16 is a top view of a vertebra and another embodiment of an intervertebral cooling instrument positioned within a disc space adjacent to the vertebra.

FIG. 16 illustrates an embodiment of a cooling instrument 1330 in which the coolant means is an expandable gas or a liquid refrigerant that expands into a gas. As shown, the cooling instrument 1330 includes an expansion nozzle 1354, connected downstream from the coolant delivery conduit 1332, which expands the gas or compressed liquid refrigerant into an expansion chamber 1352. The expanded gas can be exhausted out of the expansion chamber 1352 through the exhaust conduit 1336. As mentioned prior, the conduits 1332, 1336, as well as any sensor wires, can be detachable. In addition, the expansion chamber 1352 can optionally be formed within an expandable member such as a balloon in a similar fashion as the embodiments described above with respect to FIGS. 15A-15C.

It will be appreciated that the cooling means can also be or can include a thermoelectric device, such as a Peltier device that is integrated into cooling instrument. The conduits in such implementations can be, or can be replaced with, electrical wires, and can optionally include a fluid circulation loop to bleed off any heat from the thermoelectric device.

In any of the embodiments described herein, the cooling instrument, including any associated expandable members, chambers, conduits, etc., can have one or more sensors placed therein or thereon. The sensors can be positioned in a variety of locations, which can depend on what the sensor is measuring. In one embodiment, the sensor can measure temperature and be positioned in a manner such that it is on, in, or near the edge of cooling instrument or balloon that is most proximate to the spinal canal or other target tissue. Such sensor placement can allow data to be collected and used to control the delivery of the cooling effect, for example as an input to the control unit. It will appreciated that the sensor(s) can measure a variety of different conditions, including temperature, strain, etc.

The one or more sensors can be connected to equipment external to the patient, including but not limited to a control unit, by one or more sensor wires, which can be detachable from the sensor and/or removable from the cooling instrument. The sensor can also be removable with the sensor wires. The sensor wires may not constitute wires at all, and can instead be optical channels, a wireless connection, or any other means known in the art for communicating sensor data.

In some implementations, the cooling instrument can include a structural carrier component, and a cooling component that is removably/selectively positionable within the carrier. The cooling component can utilize one or more of the many details described above regarding providing a cooling effect to tissue. The cooling component can be positioned in, and can be removable from (as well as insertable into) the structural carrier component. Once the cooling component is removed from structural carrier component, the structural carrier component can remain in the intervertebral space to maintain a load bearing support and spacing between adjacent vertebral bodies.

Figure 17:
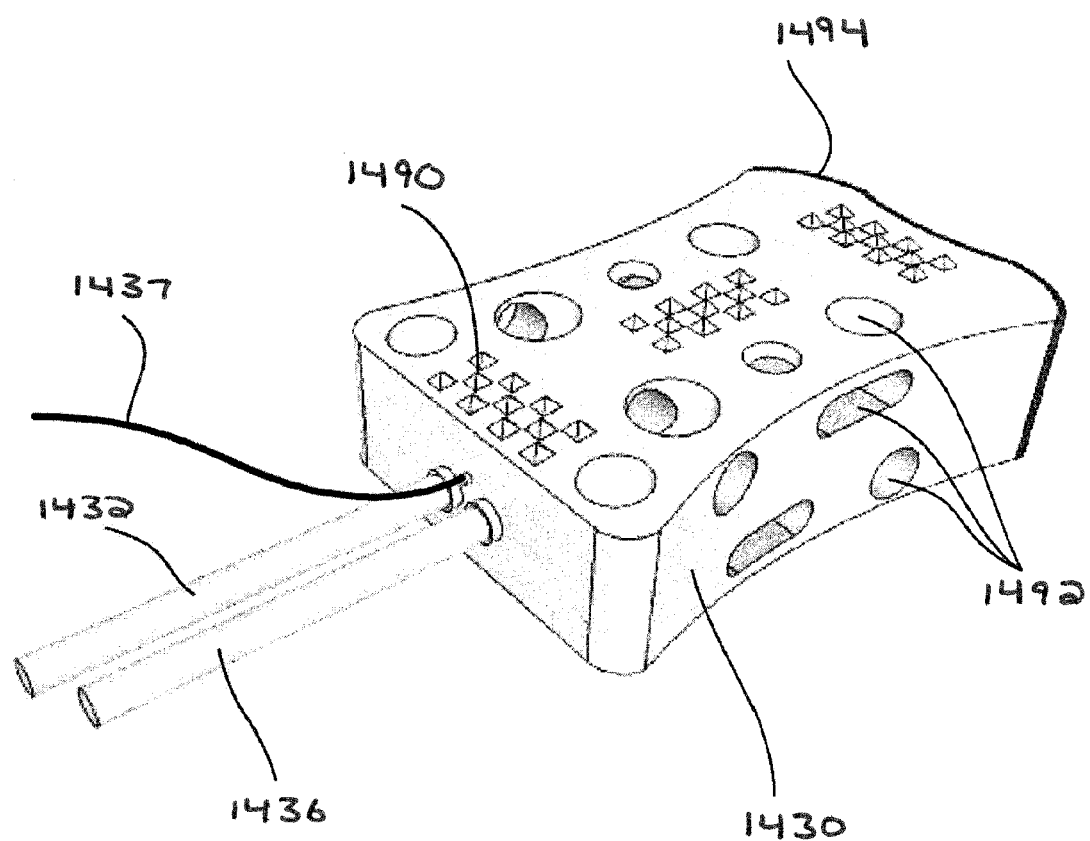
FIG. 17 is an orthogonal view of another embodiment of an intervertebral cooling instrument.

FIG. 17 depicts an exemplary embodiment of a cooling instrument 1430 that includes a rectangular body having a height equivalent to a desired distance between two adjacent vertebral bodies (after proper preparation of the area has been conducted, such as surface preparation of the adjoining axial surfaces, including clearing of endplates) that bound an intervertebral space. The cooling instrument 1430 can thus be made at different heights to accommodate varying intervertebral space heights found at the different levels of the spine and that differ between patients. Notably, this height can be defined by the distance between vertebral bodies bounding the intervertebral space by including the endplates or by recognizing that the endplates can be partially or fully removed. By matching the height of the cooling instrument 1430 to that of the desired distance between the ends of the vertebral bodies or endplates, the cooling instrument 1430 can more effectively establish and maintain the desired height between the vertebral bodies in a way that sagittal balance and proper biomechanics are maintained. In most cases, it is desirable that this height be such that it establishes and maintains the natural distance between the vertebral bodies that would have existed prior to any local injury or chronic deformation of the area. In other cases, it can be desired that the height be shorter or taller so as to establish and maintain a distance between adjacent vertebral bodies that is less or more than the natural distance. There may be cases where a portion of one or more vertebral bodies has been removed, in which case the height of the cooling instrument can be sufficient to span and maintain the distance between the axial surfaces of what is remaining of the vertebral bodies.

The superior and inferior surfaces of the cooling instrument 1430 can each have a convex shape so as to better interface with the often natural concavity of the axial surfaces of the vertebral bodies and/or the attached endplates (if applicable). In other cases, the superior and inferior surfaces of cooling instrument 1430 can be flat, such as to interface with the axial surfaces of the vertebral bodies and/or the endplates (if applicable) that have been excavated. Still in other cases, the superior and inferior surfaces of cooling instrument 1430 can be angled into each other or away from each other (antero-posteriorly) in order to establish and maintain a particularly prescribed angle between the adjacent vertebral bodies, such as to adjust or maintain the lordotic or kyphotic curves of the spine. It will be appreciated that there are other alternative superior and inferior surface shapes that can be applied to the cooling instrument 1430.

The cooling instrument 1430 can include teeth 1490 on the superior and inferior surfaces thereof so as to better engage and hold its position against the axial surfaces of the vertebral bodies once installed. In other cases, the cooling instrument 1430 can be secured against the vertebral bodies using other means, such as screws toed into the axial surfaces of the vertebral bodies. The surface(s) of the cooling instrument 1430 can also be textured in a manner which promotes bone growth and adhesion.

A longitudinal end of the cooling instrument 1430 can be "bulleted" or otherwise shaped for easier insertion into the intervertebral space during installation. Such a bulleted tip allows for the cooling instrument 1430 to more easily locate itself between the axial surfaces of adjacent vertebral bodies during the insertion process. In other cases, the cooling instrument 1430 can have a blunter tip.

The cooling instrument 1430 can also have windows or fenestrations 1492 in its surface that allow for bone graft material to be packed in, therefore promoting bone growth with adjacent vertebral bodies. The fenestrations 1492 are not necessary in all cases, and can be used in cases where the cooling instrument 1430 is also used for fusion purposes.

The cooling instrument 1430 can also have a thermally conductive surface 1494 (e.g., a surface having a thermal conductivity that is significantly higher than that of other surfaces or parts of the cooling instrument 1430). When the cooling instrument 1430 is installed in the intervertebral space, at least a portion of the thermally conductive surface 1494 can be oriented in the posterior direction such that it can more efficiently deliver its cooling effect to the tissues of the spinal canal. The thermally conductive surface 1494 can be made of a material that has a relatively high thermal conductivity (as compared to that of tissue) and can be situated such that it helps create a conductive path between the tissue of the spinal canal and the cooling features of the cooling instrument 1430, such as an expansion chamber, coolant channel, or coolant chamber.

The cooling instrument 1430 can be molded, milled, formed, and/or grown into its shape using a variety of different materials. These materials can include metals, such as titanium and stainless steel, plastics, such as PEEK, ceramics, and bone allograft. The cooling instrument 1430 can be produced from a single piece of such material, constructed from multiple pieces of the same material, or can be constructed from multiple pieces of differing material. The cooling instrument 1430 can also have moving or adjustable pieces to it. Moving or adjustable pieces can be desirable in cases where it is desired to preserve motion between the adjacent vertebral bodies or where it is desirable to have the cooling instrument 1430, or parts thereof, be expandable between adjacent vertebral bodies to restore a desired height (e.g. a natural disc height).

It will be appreciated that any of a variety of existing intervertebral implants can be retrofitted to include a cooling device. For example, a cooling instrument can be provided in accordance with the principles disclosed herein that can fit within a cavity or opening of an existing intervertebral implant or be coupled to such an implant.

Intervertebral Process and Operation

Figure 18:
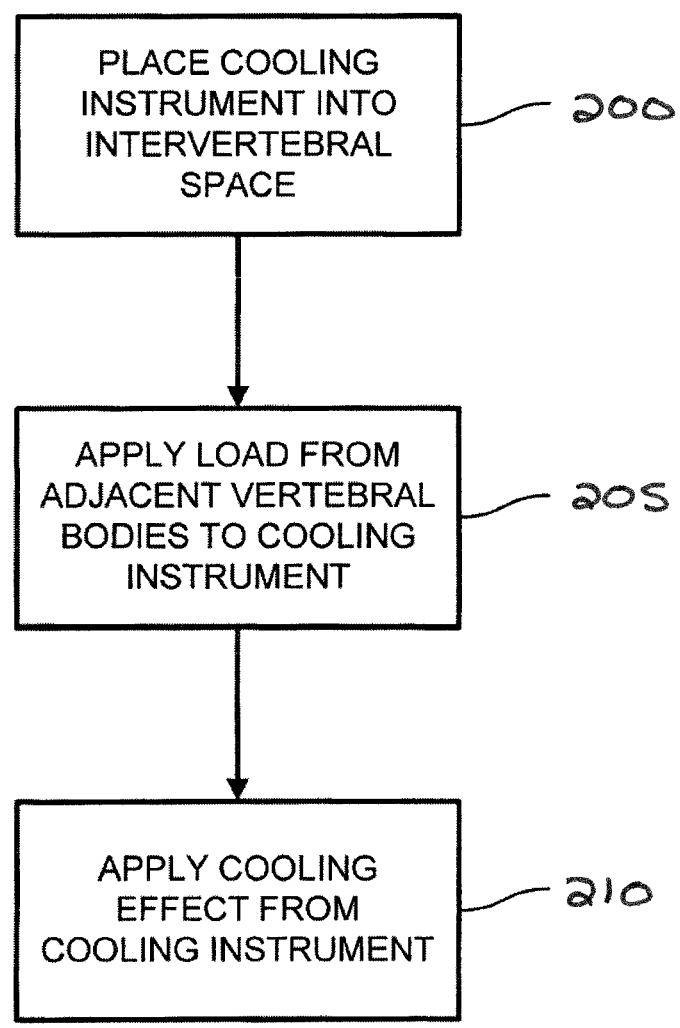
FIG. 18 is a flow chart of a process for cooling tissue using a cooling instrument.

FIG. 18 is a flow chart of an exemplary method of cooling tissue using an intervertebral approach. Before initiating the process of FIG. 18, an access to an intervertebral space is created. Creating such an access can entail a variety of different approaches and procedures. In an exemplary procedure, after having exposed the spinal segments of interest by forming a tissue opening, annulus fibrosis can be incised and the intervertebral disc can be removed in its near entirety along with the opposing endplates. Retractors can then be positioned such that cooling instrument positioning is feasible. In one embodiment, the posterior longitudinal ligament can be displaced or removed to allow placement of the cooling instrument right up against the dura of the spinal canal.

In step 200, the cooling instrument is inserted through the tissue opening and into the intervertebral space. The cooling instrument can consist of multiple components, including a structural carrier component and a removable cooling component. The insertion of the cooling instrument into the intervertebral space can include the insertion of the cooling component into a cavity of the carrier component which was previously installed in the intervertebral space.

The insertion of the cooling instrument can also include tapping the cooling instrument into the intervertebral space with tools, such as with a hammer/mallet and tamp. Alternatively, the cooling instrument can be positioned into the intervertebral space using interspace spreaders, or can be leveraged into place. Alternatively, the cooling instrument can be simply slid into the intervertebral space while applying traction. Insertion techniques can vary based on the condition of the patient and the intervertebral disc and adjacent vertebral bodies. In some cases, the compressive forces by the adjacent vertebral bodies can require a forceful insertion of the cooling instrument through use of tapping or leveraging. Other conditions can allow for the cooling instrument to simply be slid into place in the intervertebral space.

The cooling instrument can be inserted to a variety of locations within the intervertebral space. Preferably, the cooling instrument is placed in the intervertebral space such that a cooling portion of the cooling instrument is near the posterior side of the intervertebral space and proximate to or abutting the spinal canal. It will be appreciated though that the cooling instrument can be placed elsewhere within the intervertebral space and still provide an effective cooling effect to the spinal canal. It will be appreciated that the cooling instrument can be inserted into any one or more of the many intervertebral spaces of the spine.

Once inserted into the intervertebral space, the cooling instrument can remain fixed in place in the intervertebral space by the friction between the axial surfaces of adjacent vertebral bodies and the surface of the cooling instrument. Alternatively, the cooling instrument can be fixed to the adjacent vertebral bodies, by screwing, fastening, or other means.

In step 205, a load is applied to the cooling instrument. This load can include, but is not limited to, compressive forces, axial torsion, and shear forces, all delivered from adjacent vertebral bodies. This application of load can exist passively by the cooling instrument being forced into position between already compressively loaded vertebral bodies, or can be actively applied by removing traction from the patient's spine or by removing distracting instruments from the vertebrae. It will be appreciated that these loads can simply be realized upon the cooling instrument by the nature of the cooling instrument being placed in the intervertebral space and it restoring and maintaining a spanned distance between two adjacent vertebral bodies. The loads that the cooling instrument can bear, include, but are not limited to, the forces between the vertebral bodies that are created by the ligamentous tissue, created by the patients weight, created by the patient's movement, and forces created by other surgical instrumentation. The variety of forces or loads that the cooling instrument can bear can be applied before, during or after the cooling instrument delivers a cooling effect (step 210). It will be appreciated that some of these forces may not be applied or realized to the cooling instrument until the patient is out of the operating room and positioned upright.

In step 210, the cooling effect is delivered from the cooling instrument. In one aspect of the subject matter described, this delivery of the cooling effect includes circulating a chilled fluid through the cooling instrument, causing it to rapidly cool itself and the tissues adjacent to it. Alternatively, other coolant means can be used besides circulating a chilled fluid, including expanding gas through the cooling instrument, as well as powering a Peltier device in the cooling instrument. The delivery of the cooling effect, in some implementations, includes delivering the coolant means from a coolant source, such as a tank of compressed gas. In this step, the tank of compressed gas can be opened such that the compressed gas flows through a tube (e.g., a coolant delivery conduit) to the cooling instrument. Preferably, the tank can have a regulation or control unit that controls how much and how fast compressed gas is delivered to the cooling instrument. The control unit can simply be a manually operated valve, and the delivering of the cooling effect can be initiated by manually opening the valve. Alternatively, the control unit can include a computer controlled valve that uses either pre-programmed data or perioperatively-measured data to determine how much of a cooling effect should be delivered. For instance, the control unit can read data from a temperature sensor placed intrathecally, and when the intrathecal temperature is reduced below a threshold, the control unit can begin to limit or turn off the delivery of the cooling effect. When the intrathecal temperature rises above the temperature threshold, the control unit can begin delivering the cooling effect again. It will be appreciated that any number of physiological characteristics (as previously mentioned), both quantitative and qualitative, can be used as input to the control unit for the purposes of controlling the delivery of the cooling effect. In the case where the coolant means is a chilled liquid, the control unit can include a variable rate pump.

In some cases, after the cooling instrument has been installed into the intervertebral space, and all conduits and wires have been attached (if they were not previously attached), the surgical wound is mostly closed prior to delivering the cooling effect, leaving only enough opening for any conduits and wires to communicate between the cooling instrument and an extracorporeal coolant source and/or control unit. In such a case, once the cooling effect has been delivered and has since ceased, the conduits and wires can be remotely detached from the cooling instrument and pulled out through the mostly closed wound without needing to re-open the wound. In alternative cases, the wound can remain open until after the cooling effect has been delivered and the conduits and wires have been detached and removed from the patient's body.

Exemplary Intervertebral Implementation

As an illustrative example of an intervertebral implementation, the intervertebral space between two vertebral bodies is accessed via an anterior cervical approach to expose the C5-C6 intervertebral disc. Self retaining retraction is positioned and the annulus fibrosis is incised and excised. The disc in its near entirety is removed along with the opposing endplates. The height, width, and depth of the intervertebral space are measured. Into that excavated space, the cooling instrument is tapped into place, such that it has a thermally transmissive region near or abutting the tissues of the spinal canal and also so that it can bear the loads and pressures that a disc typically would in a balanced and secure manner. Care is taken to measure and position the cooling instrument such that it provides restoration of physiological lordosis, and provides a secure scaffold for bone grafts with or without an anterior plate. The compressive forces between the adjacent vertebral bodies create enough friction between the vertebral bodies and the cooling instrument that it is held in place.

The cooling instrument is connected to a fluid pump and chilled fluid basin via two conduits, one that delivers the chilled fluid to the cooling instrument, and one that carries the fluid back to the basin where it is re-chilled. The cooling instrument has a fluid channel inside of it, where the chilled fluid it receives is passed though and conducts heat away from the cooling instrument, and thus the surrounding tissue.

The cooling instrument also has embedded in it a temperature sensor that measures the temperature of the metal of the cooling instrument near the edge closest to the spinal canal. This embedded temperature sensor, via wires, provides temperature data that can be used to regulate the delivery of the chilled fluid to the cooling instrument, and thus used to control the delivery of the cooling effect of the instrument. In particular, this temperature data can be used to adjust both the volume-flow rate of the pump as well as the temperature of the chilled fluid basin.

Additionally, a temperature probe is inserted near the spinal cord to measure the temperature of tissue proximate to the spinal cord. This temperature information is relayed via wires to a control unit and used to either display for manual control and regulation of the delivery of the gas, or used to automatically control the delivery of the chilled fluid. These two temperature measurements can be used in conjunction with each other for this control.

At the start of the cooling procedure, chilled fluid is delivered at a predetermined volumetric flow rate to the cooling instrument, and its temperature is monitored. The delivery of the fluid is regulated, and the volumetric flow rate of fluid delivered to the cooling instrument is either increased or decreased until the temperature of the cooling instrument is reduced to a predetermined temperature. In addition, the temperature of the chilled fluid in the chilled fluid basin can be adjusted as well. The delivery of the fluid is continually regulated to maintain that predetermined temperature at the cooling instrument.

As the cooling instrument begins to cool the surrounding tissue, including the spinal cord, the temperature of the tissue proximate to the spinal cord is monitored. When the temperature of the tissue proximate to the spinal cord is reduced to a predetermined level, the regulation of the cooling is continually adjusted to decrease (or increase) the delivery of chilled fluid to the cooling instrument in order to maintain the predetermined temperature at the tissue proximate to the spinal cord.

After a predetermined period of time, the delivery of chilled fluid to the cooling instrument is slowly reduced, and the temperature of the tissue proximate to the spinal cord is allowed to slowly return to normothermia.

Once the cooling procedure has completed, and the delivery of chilled fluid to the cooling instrument has been reduced fully to deliver no fluid, a vacuum is applied to the conduits to evacuate any remaining fluid left in the conduits and the cooling instrument. Once evacuated, the conduits as well as any sensor wires are detached from the cooling instrument and removed from the patient's body. The cooling instrument remains in place in the intervertebral space, and bone graft material is packed in and around it to help facilitate future bone growth. The surgical incisions are closed.

CONCLUDING STATEMENTS

It will be understood that any of the methods, systems, and devices disclosed herein can be used on multiple vertebrae at once and/or multiple bony structures of each vertebra at once, by utilizing multiple cooling instruments at the same time. It will further be understood that the methods and devices disclosed herein can be used on multiple intervertebral spaces at once by utilizing multiple cooling instruments at the same time.

The above description assumes the intervertebral space to be between two adjacent vertebral bodies. There may be cases where an entire vertebral body is removed (e.g. full corpectomy), and in such a case, the cooling instrument of the subject matter described herein can span between the axial surfaces of two non-adjacent vertebral bodies (e.g. C5-C7) occupying the space once occupied by two discs and an entire vertebral body (e.g. C6).

It will be understood that the methods, systems, and devices disclosed herein can be used for conditions other than traumatic spinal cord injury, including for cooling other tissues. The methods, systems, and devices can be used for other types of spinal cord injury, as well as for treating nerve root damage. The methods, systems, and devices can be used prophylactically. The methods, systems, and devices can be used before, during, and/or after an injury occurs and can be used pre-operatively, peri-operatively, and/or post-operatively with regard to any particular procedure that can be conducted. Furthermore, the methods, systems, and devices can be used for non-injury related purposes.

In particular, the methods, systems, and devices described herein can be used as an adjunctive procedure to an aneurysm repair surgery, such as thoracoabdominal aortic aneurysm repair or abdominal aortic aneurysm repair. In these procedures, it is common for blood flow to the spinal cord to be compromised, thus introducing a risk of ischemic spinal cord injury. The methods, systems, and devices described herein can provide a protective therapy during such ischemic periods.

Further, the methods, systems, and devices described herein can also be used for spinal fusion procedures where cooling is not initially intended. The methods, systems, and devices described herein can be used for fusion with the understanding that an intraoperative complication can occur (example: iatrogenic injury caused during scoliosis correction surgery) where having the capability to deliver a cooling effect can be desired.

The methods, systems, and devices described herein can be used prophylactically to deliver a cooling effect to nerve roots. Though such delivery of a cooling effect can be achieved with one cooling instrument, it may be better achieved by having two or more cooling instruments placed above and below the particular root that is being targeted. The delivery of a cooling effect to a nerve root can also occur perio-operatively or post-operatively.

It will be appreciated that the methods, systems, and devices disclosed herein can be used in other parts of a mammalian body, and in particular, can be used with orthopedic procedures to deliver a cooling effect to surrounding tissues.

The described aspects above are given as illustrative examples of those that fall within the scope of the subject matter described, but are not intended to limit that scope. The described devices and methods can be the sole devices and methods used and performed in the spine at the time of the herein described therapy or can accompany other devices and procedures such as those related to spinal decompression, reduction, stabilization, and fusion.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

The foregoing description has been presented for purposes of illustration and description. Many modifications and variations of the subject matter described will be apparent to those skilled in the art. Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A method for cooling tissue, comprising:
delivering an implant through a tissue opening and into a bony structure of a vertebra, the implant being fixedly engaged with the vertebra; and
applying a cooling effect to the bony structure from the implant to cool tissue in a spinal canal adjacent to the vertebra;
wherein the implant comprises a bone screw.

2. The method of claim 1, wherein the implant is configured to be used as a fixation device.

3. The method of claim 1, wherein delivering the implant comprises implanting the bone screw into a pedicle of the vertebra.

4. The method of claim 1, further comprising coupling a spinal stabilization rod to the implant.

5. The method of claim 1, wherein delivering the implant comprises threading the implant into the bony structure of the vertebra.

6. The method of claim 1, further comprising closing the tissue opening with the implant remaining in the bony structure of the vertebra.

7. The method of claim 1, wherein applying the cooling effect comprises delivering a pressurized gas to a chamber formed within the implant.

8. The method of claim 1, wherein applying the cooling effect comprises delivering a cooled liquid to a chamber formed within the implant.

9. The method of claim 8, further comprising withdrawing the cooled liquid from the chamber through an exhaust conduit.

10. The method of claim 1, further comprising dynamically controlling the cooling effect to increase and decrease the cooling effect.

11. The method of claim 10, wherein said controlling comprises increasing or decreasing a rate of fluid flow through the implant based on one or more measured physiological characteristics.

12. The method of claim 11, further comprising, prior to or during said controlling, measuring the one or more measured physiological characteristics using a sensor.

13. The method of claim 10, wherein said controlling comprises increasing or decreasing a temperature of fluid supplied to the implant based on one or more measured physiological characteristics.

14. The method of claim 1, wherein the bone screw comprises an insert and delivering the implant comprises inserting the bone screw into a bone hole and then delivering the insert into an opening in the bone screw.

15. The method of claim 1, further comprising separating the at least one conduit from the implant.

16. The method of claim 15, wherein separating the at least one conduit comprises deflating a coupling balloon.

17. The method of claim 1, wherein the bony structure is a posterior arch of the vertebra.

18. The method of claim 1, wherein the bony structure is a lamina of the vertebra.

19. The method of claim 1, wherein the bony structure is a pedicle of the vertebra.

20. The method of claim 19, wherein the implant is positioned in proximity to a wall of the pedicle adjacent to a spinal canal such that applying the cooling effect cools the spinal canal.

21. The method of claim 1, further comprising delivering a second implant into a contralateral side of the vertebra.

22. The method of claim 1, wherein applying the cooling effect reduces a temperature of a portion of a spinal cord adjacent to the vertebra by at least about 2 degrees C.

23. An apparatus for cooling a spinal canal, comprising:
a biocompatible bone screw having proximal and distal ends and a chamber therein, the bone screw being configured for placement within a vertebra;
a delivery conduit coupled to the bone screw and in fluid communication with the chamber, the delivery conduit being configured to supply a cooling medium to the chamber;
an exhaust conduit coupled to the bone screw and in fluid communication with the chamber;
a coolant source having a cooling medium therein, the coolant source being configured to provide the cooling medium to the delivery conduit; and
a cannulated tunnel extending through an entire length of the bone screw, the cannulated tunnel being in fluid isolation relative to the chamber.

24. The apparatus of claim 23, wherein the bone screw comprises a body portion, a neck portion proximal to the body portion, and a head portion proximal to the neck portion.

25. The apparatus of claim 24, wherein the delivery conduit and the exhaust conduit are coupled to the neck portion of the bone screw.

26. The apparatus of claim 25, wherein the neck portion is curved or bent such that the head portion is offset from a longitudinal axis of the body portion.

27. The apparatus of claim 24, wherein the head portion includes a driving interface and the delivery conduit and exhaust conduit are configured to be selectively coupled to the driving interface.

28. The apparatus of claim 23, further comprising an expansion nozzle disposed at a distal end of the delivery conduit.

29. The apparatus of claim 28, wherein the expansion nozzle is disposed in a central portion of the bone screw.

30. The apparatus of claim 28, wherein the expansion nozzle is disposed in a portion of the bone screw configured to be positioned adjacent to a patient's spinal canal when the bone screw is implanted in a pedicle of the patient.

31. The apparatus of claim 23, wherein the chamber comprises a fluid lumen having a first end coupled to the delivery conduit and a second end coupled to the exhaust conduit.

32. The apparatus of claim 31, wherein the fluid lumen is coiled.

33. The apparatus of claim 23, wherein the delivery conduit terminates at a location adjacent to the distal end of the bone screw and the exhaust conduit terminates at a location adjacent to the proximal end of the bone screw.

34. An apparatus for cooling a spinal canal, comprising:
a biocompatible bone screw having proximal and distal ends and a chamber therein, the bone screw being configured for placement within a vertebra;
a delivery conduit coupled to the bone screw and in fluid communication with the chamber, the delivery conduit being configured to supply a cooling medium to the chamber;
an exhaust conduit coupled to the bone screw and in fluid communication with the chamber; and
a coolant source having a cooling medium therein, the coolant source being configured to provide the cooling medium to the delivery conduit;
wherein the bone screw has a rod receiving head and the apparatus further comprises a spinal rod configured to be selectively coupled to the rod receiving head;
wherein the spinal rod includes an aperture through which the delivery conduit and the exhaust conduit can be routed from the bone screw to a skin surface of a patient when the spinal rod and the bone screw are implanted in a spine of the patient.

35. An apparatus for cooling a spinal canal, comprising:
a biocompatible bone screw having proximal and distal ends and a chamber therein, the bone screw being configured for placement within a vertebra;
a delivery conduit coupled to the bone screw and in fluid communication with the chamber, the delivery conduit being configured to supply a cooling medium to the chamber;

an exhaust conduit coupled to the bone screw and in fluid communication with the chamber; and a coolant source having a cooling medium therein, the coolant source being configured to provide the cooling medium to the delivery conduit;

wherein the chamber is formed in a removable insert, the insert being selectively positionable within an interior of the bone screw.

36. An apparatus for cooling a spinal canal, comprising:
a biocompatible bone screw having proximal and distal ends and a chamber therein, the bone screw being configured for placement within a vertebra;
a delivery conduit coupled to the bone screw and in fluid communication with the chamber, the delivery conduit being configured to supply a cooling medium to the chamber;
an exhaust conduit coupled to the bone screw and in fluid communication with the chamber;
a coolant source having a cooling medium therein, the coolant source being configured to provide the cooling medium to the delivery conduit; and
a coupling balloon having at least an inflated configuration in which the balloon forms an interference fit to couple the delivery conduit and the exhaust conduit to the bone screw and a deflated configuration in which the delivery conduit and the exhaust conduit are separable from the bone screw.

37. The apparatus of claim 36, wherein application of a cooling medium to the delivery conduit is effective to maintain the balloon in the inflated configuration and evacuation of a cooling medium from the delivery conduit is effective to transition the balloon from the inflated configuration to the deflated configuration.

38. A method for cooling tissue, comprising:
inserting a cooling instrument into a cannulation of a bone screw implanted in a pedicle of a vertebra; and
applying a cooling effect to the vertebra from the cooling instrument to cool tissue in a spinal canal adjacent to the vertebra.

39. An apparatus for cooling a spinal canal, comprising:
a biocompatible bone screw having proximal and distal ends and a chamber therein, the bone screw being configured for placement within a vertebra;
a delivery conduit coupled to the bone screw and in fluid communication with the chamber, the delivery conduit being configured to supply a cooling medium to the chamber;
an exhaust conduit coupled to the bone screw and in fluid communication with the chamber;
a coolant source having a cooling medium therein, the coolant source being configured to provide the cooling medium to the delivery conduit; and
a Peltier device disposed within the chamber and a controller configured to adjust an amount of current supplied to the Peltier device.

40. The apparatus of claim 39, wherein the delivery conduit comprises an electrical lead for supplying current to the Peltier device and the exhaust conduit is configured to remove heat generated by the Peltier device from the chamber.

41. An apparatus for cooling a spinal canal, comprising:
a biocompatible bone screw having proximal and distal ends and a chamber therein, the bone screw being configured for placement within a vertebra;
a delivery conduit coupled to the bone screw and in fluid communication with the chamber, the delivery conduit being configured to supply a cooling medium to the chamber;
an exhaust conduit coupled to the bone screw and in fluid communication with the chamber;
a coolant source having a cooling medium therein, the coolant source being configured to provide the cooling medium to the delivery conduit; and
at least one sensor configured to generate an output indicative of at least one of a physiological condition and a temperature of the bone screw, and a controller configured to adjust at least one of a rate at which a cooling medium is provided to the delivery conduit and a temperature of the cooling medium based on the output of the sensor.

* * * * *